(12) United States Patent
Draelos

(10) Patent No.: US 12,086,563 B1
(45) Date of Patent: Sep. 10, 2024

(54) SYSTEMS AND METHODS FOR CONSTRUCTING A NARRATIVE OF AN INTERACTION WITH A SUBJECT

(71) Applicant: Rachel Lea Ballantyne Draelos, Durham, NC (US)

(72) Inventor: Rachel Lea Ballantyne Draelos, Durham, NC (US)

(*) Notice: Subject to any disclaimer, the term of this patent is extended or adjusted under 35 U.S.C. 154(b) by 354 days.

(21) Appl. No.: 17/394,360

(22) Filed: Aug. 4, 2021

Related U.S. Application Data

(60) Provisional application No. 63/061,220, filed on Aug. 5, 2020.

(51) Int. Cl.
| | |
|---|---|
| G06F 40/56 | (2020.01) |
| G06N 5/02 | (2023.01) |
| G16H 10/20 | (2018.01) |
| G16H 80/00 | (2018.01) |

(52) U.S. Cl.
CPC .............. *G06F 40/56* (2020.01); *G06N 5/02* (2013.01); *G16H 10/20* (2018.01); *G16H 80/00* (2018.01)

(58) Field of Classification Search
CPC ........ G06F 40/56; G16H 10/20; G16H 80/00; G06N 5/02
See application file for complete search history.

(56) References Cited

U.S. PATENT DOCUMENTS

| | | | |
|---|---|---|---|
| 10,622,101 B1 * | 4/2020 | Dunlap | G16H 10/20 |
| 11,355,239 B1 * | 6/2022 | Nelson | G09B 19/00 |
| 2012/0197657 A1 | 8/2012 | Predanovic | |
| 2017/0147751 A1 | 5/2017 | Schwartz et al. | |
| 2018/0068076 A1 | 3/2018 | Farri et al. | |
| 2018/0089382 A1 | 3/2018 | Allen et al. | |
| 2018/0308565 A1 | 10/2018 | Pinter et al. | |
| 2018/0365590 A1 | 12/2018 | Cucci et al. | |
| 2019/0019578 A1 * | 1/2019 | Vaccaro | G16H 40/63 |

(Continued)

FOREIGN PATENT DOCUMENTS

| | | | | |
|---|---|---|---|---|
| CA | 2398823 A1 * | 2/2001 | | G16H 10/20 |
| CA | 2311439 C * | 5/2007 | | G10L 17/26 |

(Continued)

OTHER PUBLICATIONS

Clinical Assistant webpage, http://mymedassist.com/#features (accessed Mar. 28, 2020).

*Primary Examiner* — Mohammad K Islam
(74) *Attorney, Agent, or Firm* — Olive Law Group, PLLC

(57) ABSTRACT

Systems and methods for constructing a narrative of an interaction with a subject are disclosed. According to an aspect, a method includes receiving response prompts for interacting with a subject. The method includes constructing a data structure including a set of nodes. Each of the nodes corresponds to one of the response prompts. Each link is traversable based on a response to a response prompt at the respective node. The method includes providing a narrative build manager configured to receive one or more responses to one or more response prompts of the set of nodes. The narrative build manager is configured use the one or more responses to traverse the links. The narrative build manager is configured to construct a narrative of an interaction with a subject based on the traversal of the links and the responses to the response prompts at one or more nodes.

30 Claims, 69 Drawing Sheets

(56) References Cited

U.S. PATENT DOCUMENTS

| | | |
|---|---|---|
| 2019/0228848 A1 | 7/2019 | Saliman |
| 2019/0311807 A1 | 10/2019 | Kannan et al. |
| 2019/0392926 A1 | 12/2019 | Koh et al. |
| 2020/0185088 A1* | 6/2020 | Kaliraman ............ G06N 5/048 |
| 2021/0319898 A1* | 10/2021 | Kapoor ................ A61B 5/0205 |
| 2023/0130914 A1* | 4/2023 | Kaliraman ............ G16H 10/60 |
| | | 705/2 |

FOREIGN PATENT DOCUMENTS

| | | | | |
|---|---|---|---|---|
| CA | 2836467 A1 * | 11/2012 | ........... | A61B 5/0002 |
| CA | 3110577 A1 * | 3/2020 | ........... | A61B 5/0022 |

* cited by examiner

"TS" stands for "Template Sentence"

"TS" stands for "Template Sentence"

| Body System | Question Category | Question ID | Question | Question Display Type | Response to More Questions | Child Questions | Template Sentence | YES: Template Sentence | NO: Template Sentence |
|---|---|---|---|---|---|---|---|---|---|
| CVRESP | CHEST_PAIN | CHP0001 | Do you have chest pain? | YES-NO | YES | PAIN001,SOB001,PEM0001,PTX0001,PMK0001,DIE0001,EXE0001,CHP0002,CHP0003,CHP0004,CHP0005,CHP0006,CHP0007,CHP0009 | | The patient has chest pain. | The patient does not have chest pain. |
| CVRESP | CHEST_PAIN | CHP0007 | Does the pain feel like any of the following: CLICK{squeezing, tightness, pressure, constriction, burning} | CLICK-BOXES | | | The pain feels like RESPONSE. It does not feel like NOTRESPONSE. | | |
| CVRESP | CHEST_PAIN | CHP0002 | Are any of the following symptoms associated with your chest pain: CLICK{weakness, fatigue, cold sweat, dizziness, nausea, vomiting, indigestion, clammy feeling, fainting, light-headedness} | CLICK-BOXES | | | The patient reports RESPONSE. They do not report NOTRESPONSE. | | |
| CVRESP | CHEST_PAIN | CHP0006 | Does the pain get better with sitting up and leaning forward? | YES-NO | | | | The pain improves with sitting up and leaning forward. | The pain does not improve with sitting up and leaning forward. |
| CVRESP | CHEST_PAIN | CHP0009 | Does the pain get worse with any of the following: {exercise, cold, emotional stress, sexual intercourse, smoking, swallowing, after meals} | CLICK-BOXES | | | The chest pain gets worse with RESPONSE. The pain does not get worse with NOTRESPONSE. | | |
| CVRESP | CHEST_PAIN | CHP0003 | Have you ever experienced any of the following conditions: CLICK{heart disease, heart attack, high blood pressure, high cholesterol, stroke, diabetes, smoking} | PMH-POP | | | The patient has a history of RESPONSE. The patient does not report a history of NOTRESPONSE. | | |
| CVRESP | CHEST_PAIN | CHP0004 | Do you have a family history of: CLICK{heart disease, heart attack, high blood pressure, high cholesterol, stroke, diabetes} | FH-POP | | | The patient has a family history of RESPONSE, and no family history of NOTRESPONSE. | | |
| CVRESP | CHEST_PAIN | CHP0005 | Are you taking any of the following substances: CLICK{blood pressure medicine, β blockers, calcium channel blockers, digoxin, diuretics, aspirin, anticoagulants, over-the-counter drugs, herbal supplements, recreational drugs} | MEDS-POP | | | The patient is taking RESPONSE. The patient does not report taking NOTRESPONSE. | | |
| MSK | JOINT_PAIN | JNT0001 | Do any of your joints hurt? | YES-NO | YES | JNT0002,JNT0003,PAIN001 | | | The patient reports no joint pain. |
| MSK | JOINT_PAIN | JNT0002 | Which joints? | LIST-TEXT | | | The patient has pain in the RESPONSE. | | |
| MSK | JOINT_PAIN | JNT0003 | Do you have any of the following symptoms with your joint pain? CLICK{rash, redness, swelling} | CLICK-BOXES | | | The patient has RESPONSE associated with their joint pain. The patient reports no NOTRESPONSE with their joint pain. | | |
| PAIN | PAIN | PAIN001 | Do you have any pain? | YES-NO | YES | GEN0001,GEN0002,GEN0003,GEN0004,GEN0005,GEN0006,PAIN002,PAIN003,PAIN004,PAIN005,PAIN006,PAIN007,PAIN008,PAIN010,PAIN011 | | | The patient reports no pain. |
| PAIN | PAIN | PAIN002 | Where do you feel the pain in your body? | LIST-TEXT | | | The patient has pain in their RESPONSE. | | |
| PAIN | PAIN | PAIN006 | On a scale of 1 to 10 (with 1 being no pain and 10 being the worst pain of your life) how would you rate your pain? | NUMBER | | | The patient rates their pain RESPONSE out of 10. | | |
| PAIN | PAIN | PAIN005 | The pain: CLICK{is constant, comes and goes} | CLICK-BOXES | | | The pain RESPONSE. | | |
| PAIN | PAIN | PAIN004 | Is the pain: CLICK{sharp, dull, burning, pulsating, cramping, pounding, pressure-like, crushing} | CLICK-BOXES | | | The pain is RESPONSE. The pain is not NOTRESPONSE. | | |
| PAIN | PAIN | PAIN003 | Does the pain travel anywhere ("radiate")? | YES-NO | YES | PAIN009 | | | The pain does not radiate anywhere. |
| PAIN | PAIN | PAIN009 | Where does the pain travel? | LIST-TEXT | | | The pain radiates to the patient's RESPONSE. | | |
| PAIN | PAIN | PAIN007 | What causes the pain to start? | LIST-TEXT | | | RESPONSE causes the pain to start. | | |
| PAIN | PAIN | PAIN010 | What causes the pain to stop? | LIST-TEXT | | | RESPONSE causes the pain to stop. | | |
| PAIN | PAIN | PAIN008 | Have you had pain like this before? | YES-NO | | | | The patient has had pain like this before. | The patient has never had pain like this before. |
| PAIN | PAIN | PAIN011 | Please describe when you have had pain like this before. | SHORT-TEXT | | | Previously, RESPONSE. | | |

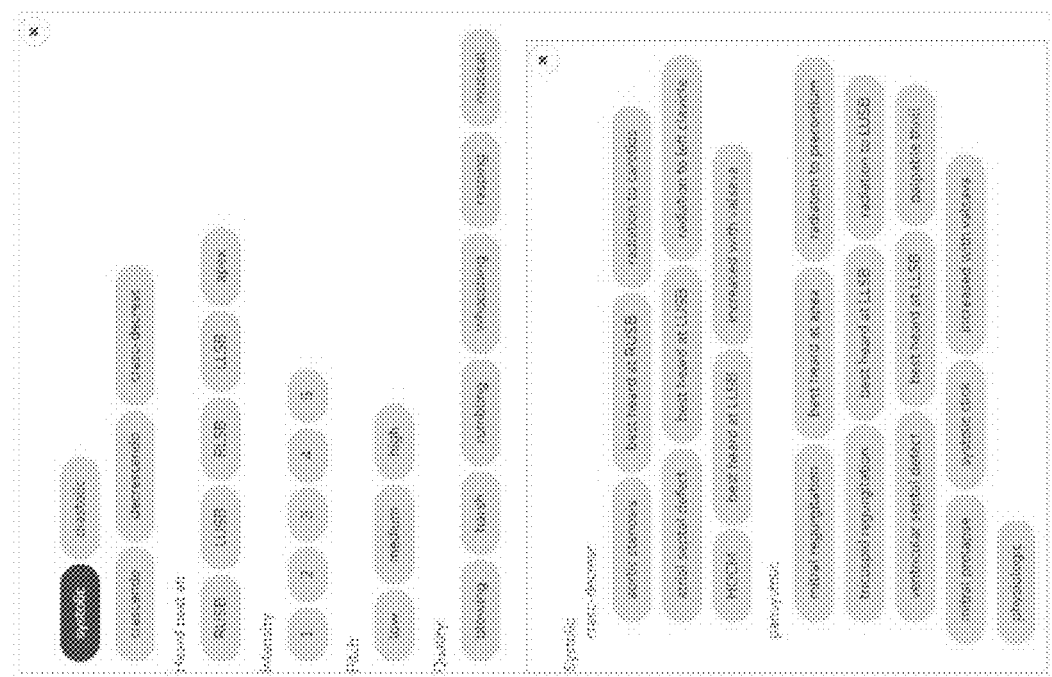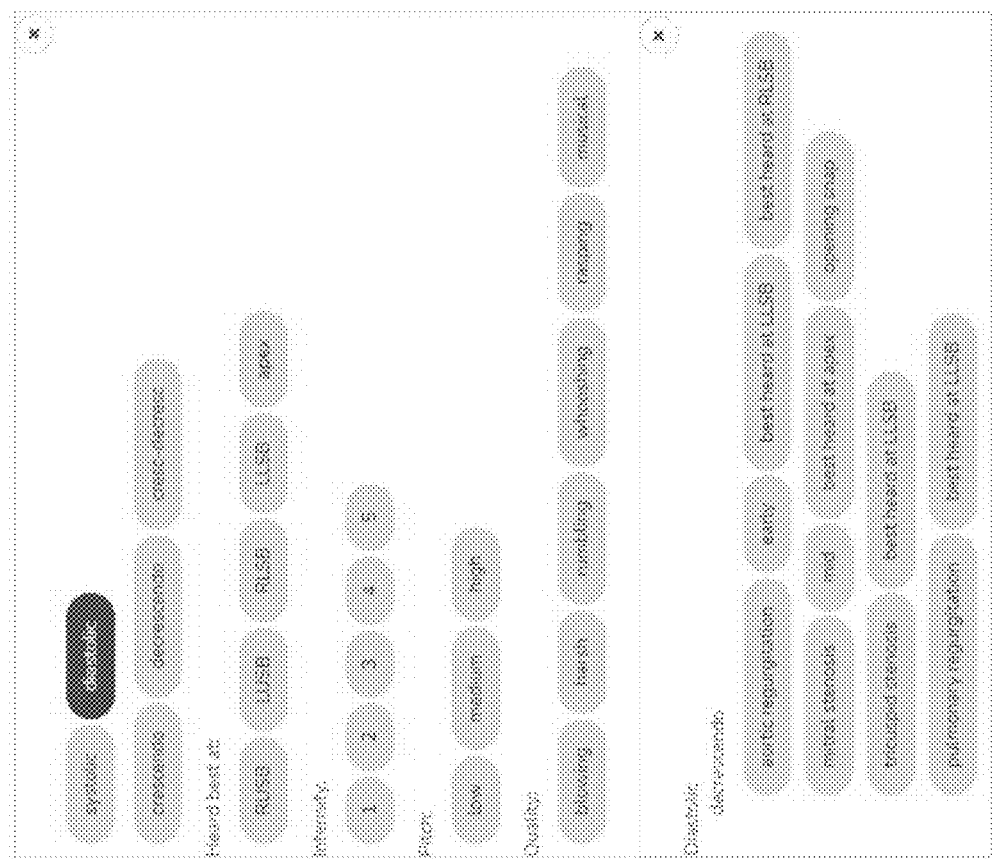
FIG. 44

SYSTEMS AND METHODS FOR CONSTRUCTING A NARRATIVE OF AN INTERACTION WITH A SUBJECT

CROSS REFERENCE TO RELATED APPLICATION

This application claims priority to U.S. Provisional Patent Application No. 63/061,220, filed Aug. 5, 2020, and titled SYSTEMS AND METHODS FOR CONSTRUCTING A NARRATIVE OF AN INTERACTION WITH A SUBJECT, the content of which is incorporated herein by reference in its entirety.

TECHNICAL FIELD

The presently disclosed subject matter generally relates to note writing and summarization. Particularly, the presently disclosed subject matter generally relates to systems and methods for constructing a narrative of an interaction with a subject.

BACKGROUND

Typically, a physician or other healthcare practitioner is provided with a medical record or access to previously written notes about a patient prior to meeting with the patient. The physician or healthcare practitioner may then review the medical record and/or notes prior to meeting with the patient so that he or she can be better informed about the patient's medical history. In this way, a scheduled appointment with the patient can be more efficiently conducted.

Often, shortly before a scheduled appointment, the patient may complete a questionnaire and/or may be interviewed by a nurse or other healthcare practitioner about the patient's current condition, medical history, and reason for the appointment. This information may be provided to the physician prior to meeting with the patient. There exist electronic-based techniques for acquiring such information. For example, a patient may complete an online questionnaire, the healthcare practitioner may enter the information into a computer while interviewing the patient, or the patient may be provided with a computing device (e.g., a tablet computer) to enter the information. Often this information is entered into a form and the completed form is provided to the healthcare practitioner to review prior to meeting with the patient. Such electronic-based techniques have improved the relay of information to the healthcare practitioner; however, there is a continuing need to provide improved systems and techniques for interviewing patients and facilitating the provision and documentation of this information in order to reduce the total time required to carry out and document a patient appointment.

BRIEF DESCRIPTION OF THE DRAWINGS

Figure 1A:
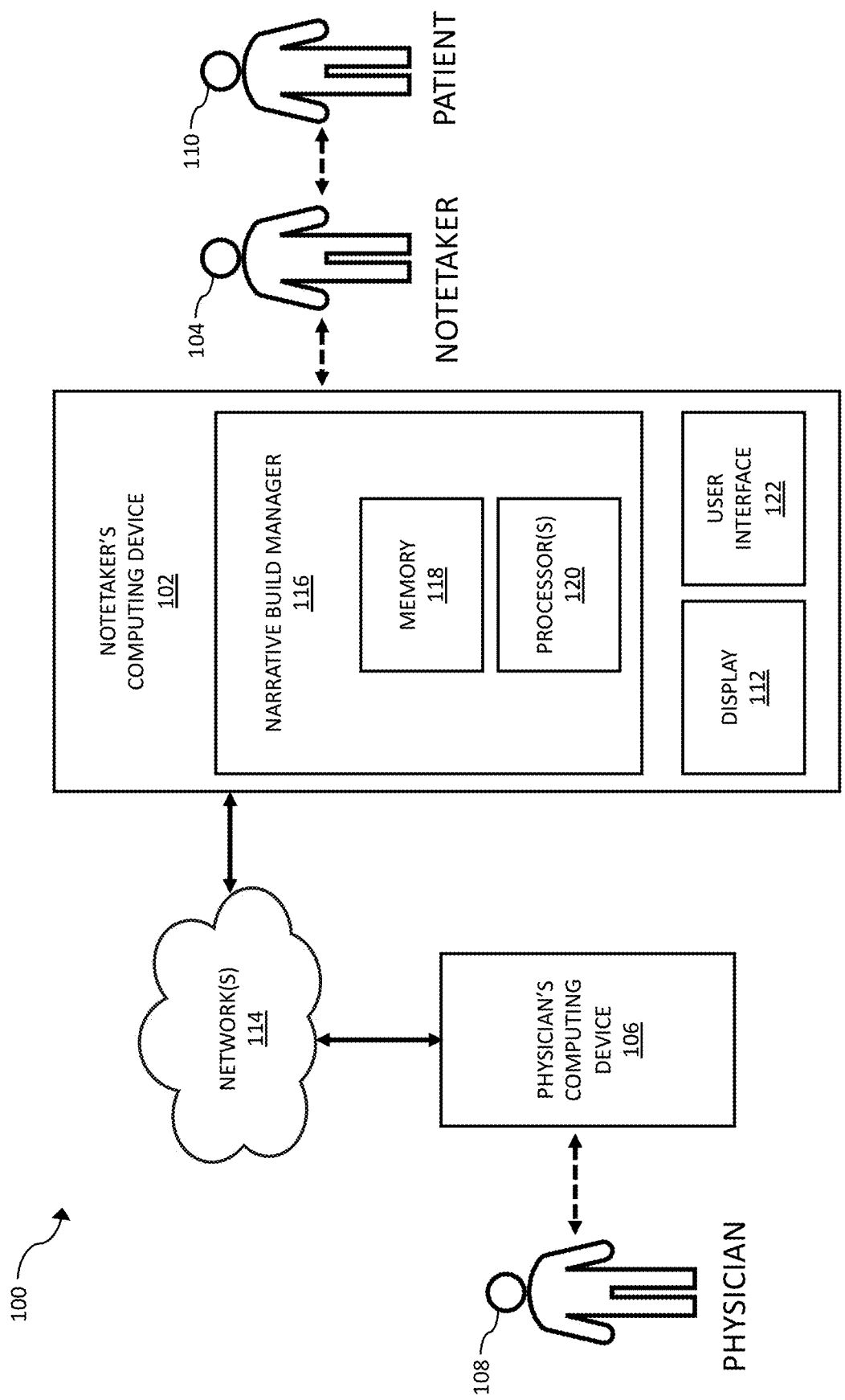
Figure 1B:
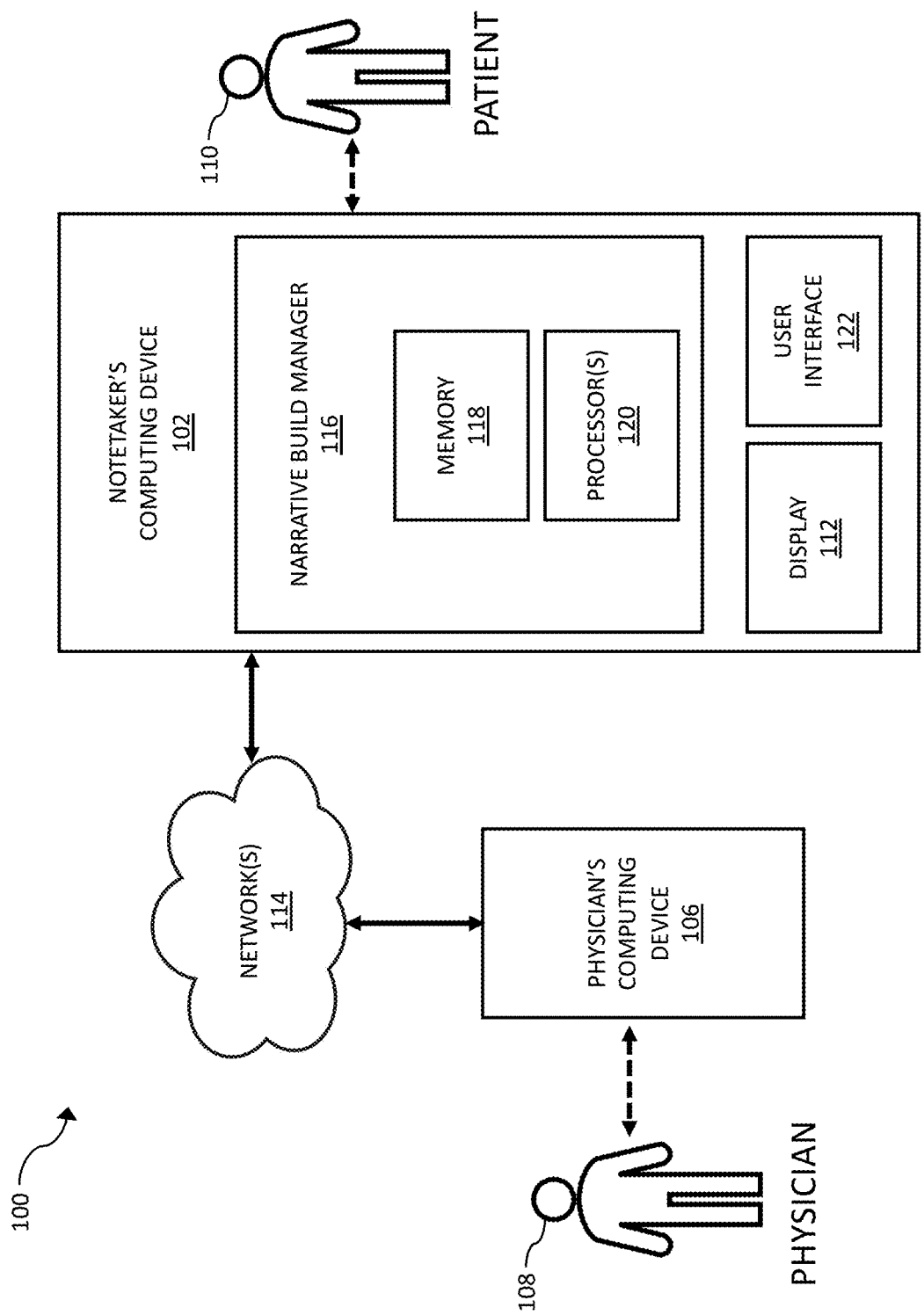
Figure 1C:
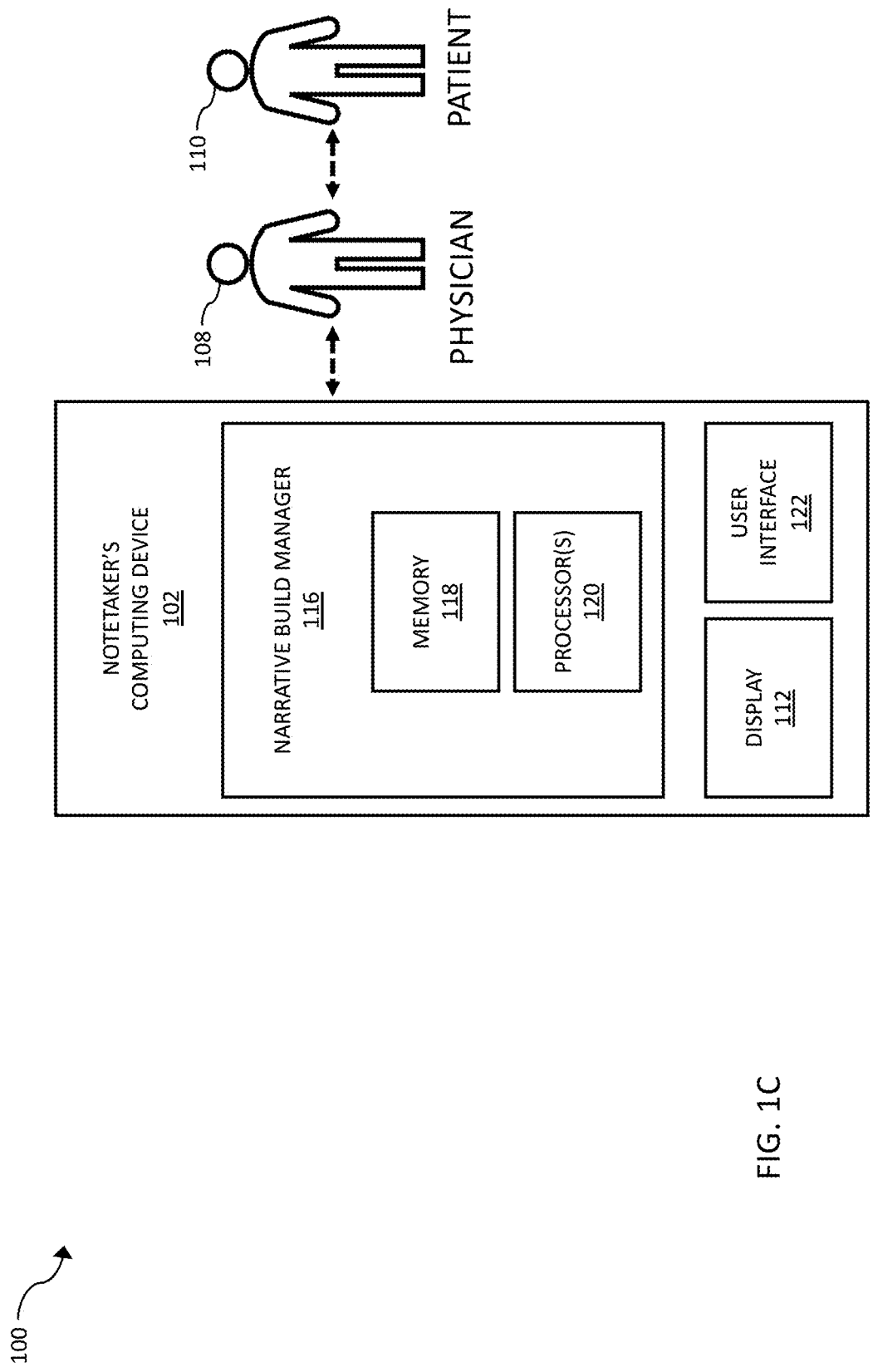
Figure 2:
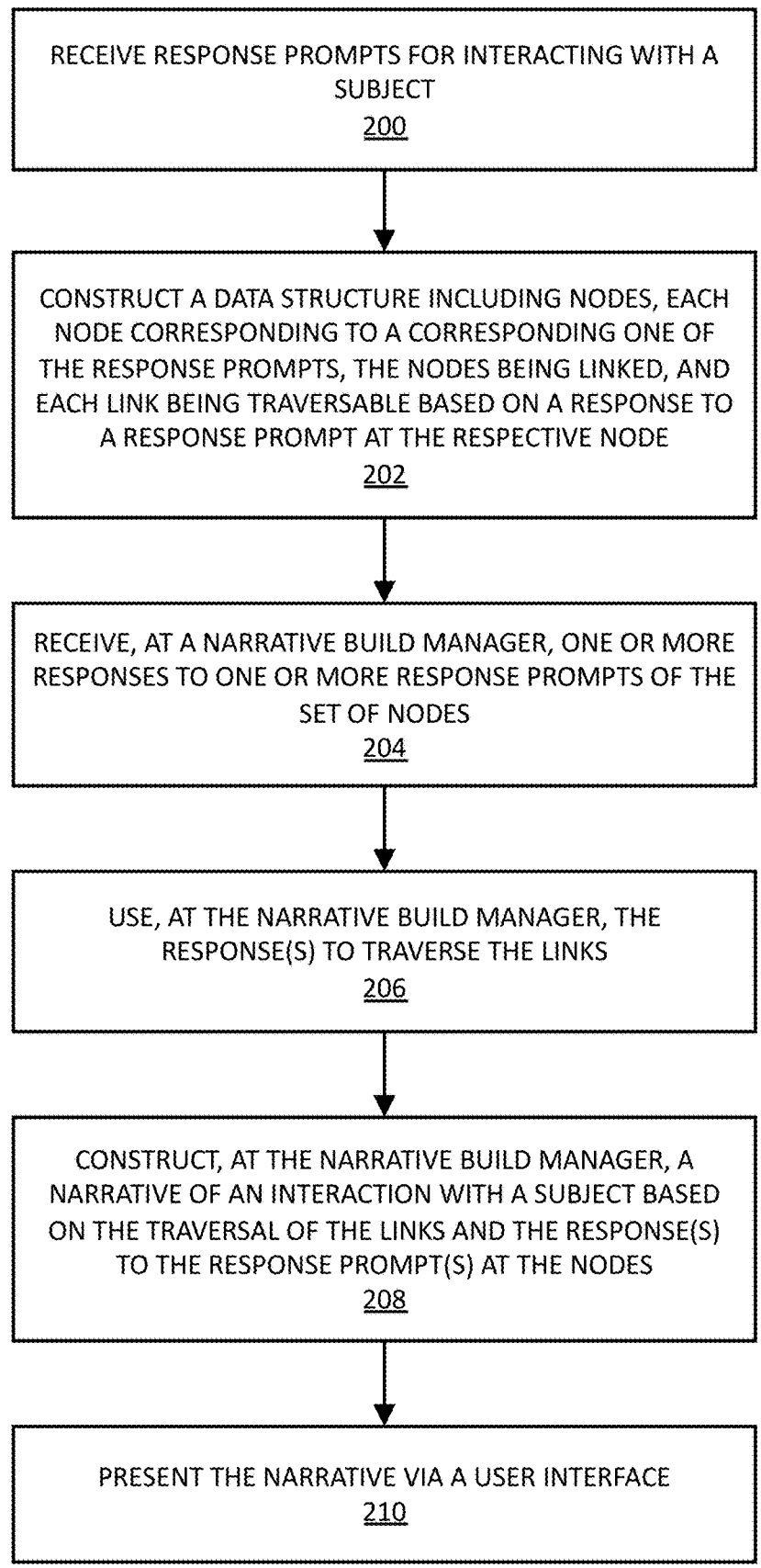
Figure 3:
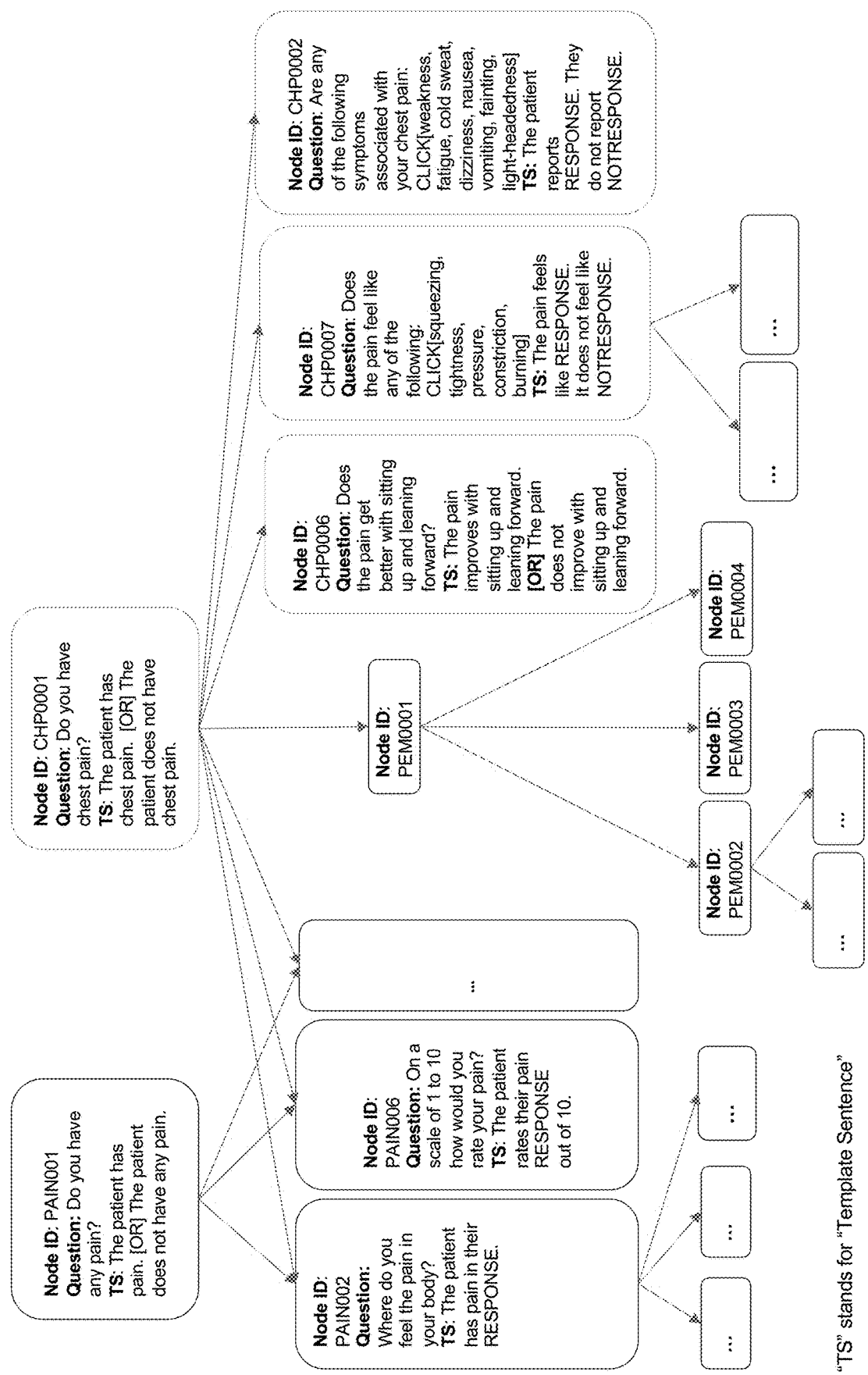
Figure 4:
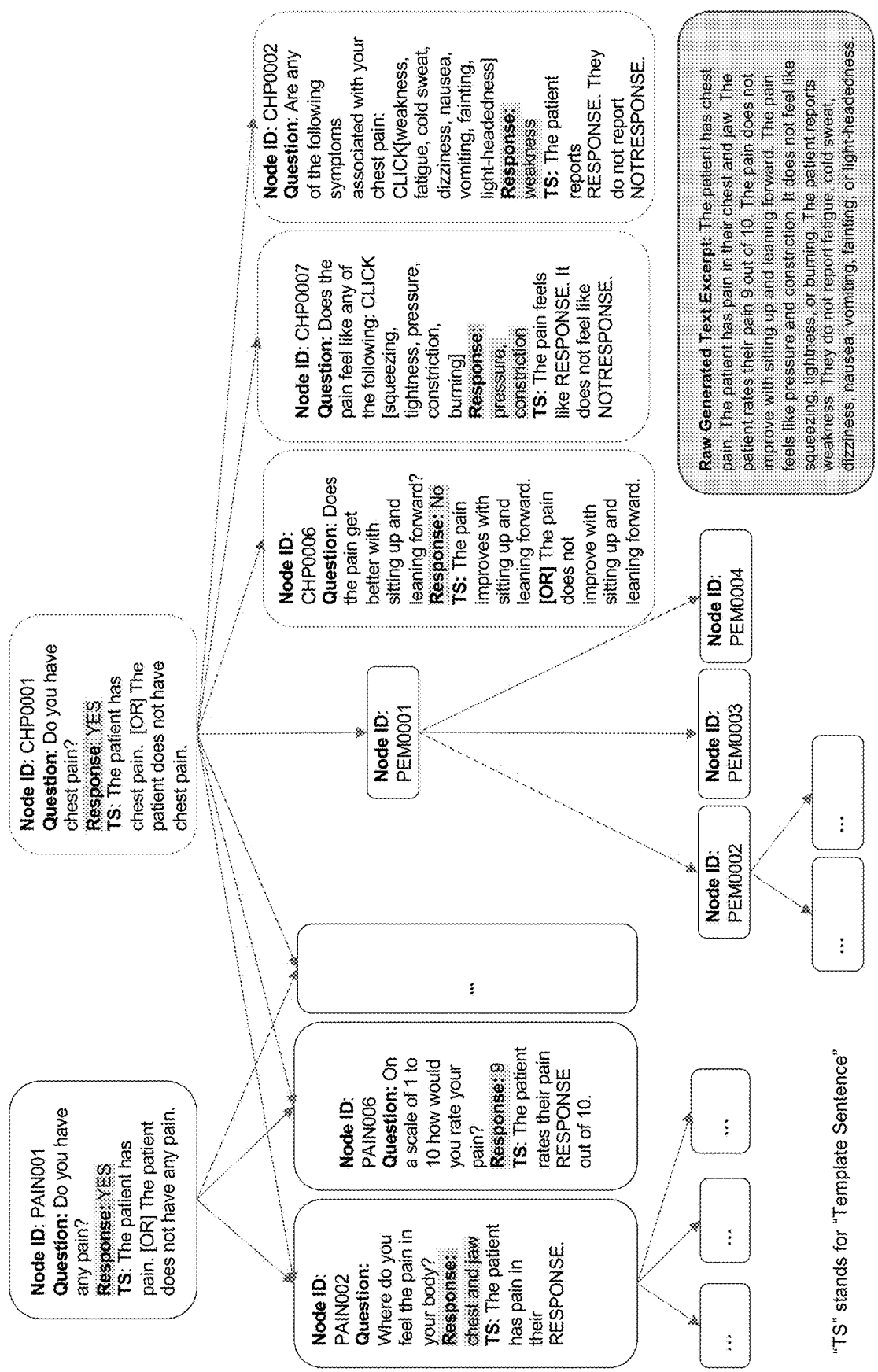
Figure 67:
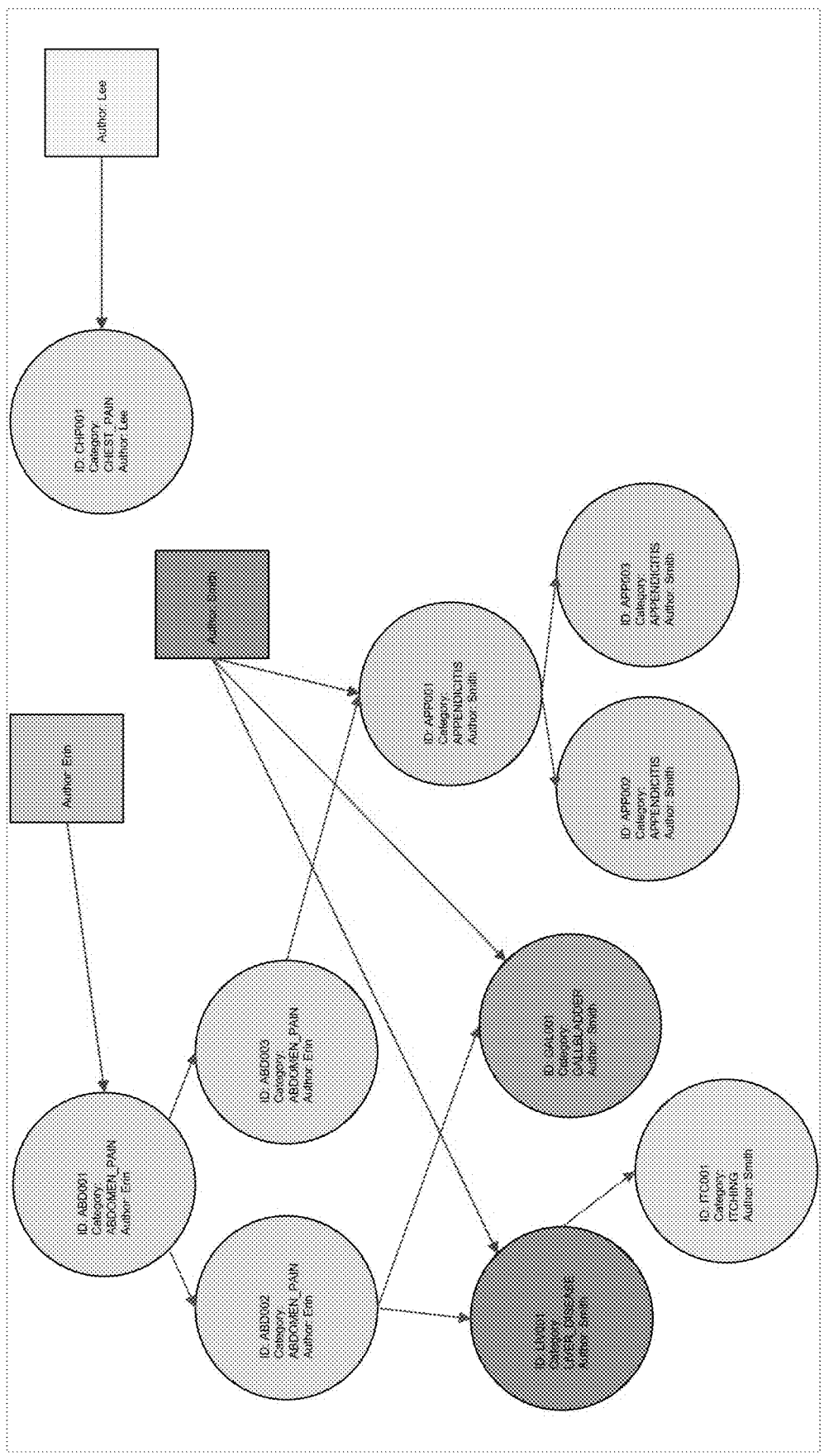

Having thus described the presently disclosed subject matter in general terms, reference will now be made to the accompanying Drawings, which are not necessarily drawn to scale, and wherein:

FIG. 1A is a block diagram of a system for constructing a narrative of an interaction with a subject and for presenting the narrative in accordance with embodiments of the present disclosure;

FIG. 1B is a block diagram of a system for construction a narrative of an interaction with a subject and for presenting the narrative in accordance with embodiments of the present disclosure;

FIG. 1C is a block diagram of a system for construction of a narrative of an interaction with a subject and for presenting the narrative in accordance with embodiments of the present disclosure;

FIG. 2 is a flowchart of a method for constructing a narrative of an interaction with a subject and for presenting the narrative in accordance with embodiments of the present disclosure;

FIGS. 3 and 4 are diagrams of example data structures for constructing a narrative of an interaction with a subject and for presenting the narrative in accordance with embodiments of the present disclosure; and FIG. 5 is a tabular representation of an example data structure for constructing a narrative of an interaction with a subject and for presenting the narrative in accordance with embodiments of the present disclosure; and FIGS. 6-67 are images of images of various screenshots of a system in accordance with embodiments of the present disclosure.

SUMMARY

The presently disclosed subject matter relates to systems and methods for constructing a narrative of an interaction with a subject. According to an aspect, a method includes receiving a plurality of response prompts for interacting with a subject. The method also includes constructing a data structure including a set of nodes. Each of the nodes corresponds to one of the response prompts. The nodes are linked. Each link is traversable based on a response to a response prompt at the respective node. The method also includes providing a narrative build manager configured to receive one or more responses to one or more response prompts of the set of nodes. The narrative build manager is also configured use the one or more responses to traverse the links. Further, the narrative build manager is configured to construct a narrative of an interaction with a subject based on the traversal of the links and the one or more responses to the one or more response prompts at one or more nodes. As an example, one or more nodes can be associated with a template sentence. The template sentence may be used by the narrative build manager.

According to another aspect, a method includes providing a data structure including a set of nodes. Each of the nodes corresponds to a response prompt. The nodes are linked. Each link is traversable based on a response to a response prompt at the respective node. Further, the method includes receiving one or more responses to one or more response prompts of the nodes. The method also includes using the one or more responses to traverse the links. Further, the method includes constructing a narrative of an interaction with a subject based on the traversal of the links and the one or more responses to the one or more response prompts at one or more of the nodes. The method also includes presenting the narrative via a user interface.

According to another aspect, a method includes rendering a user interface for a physical examination section, which includes any of the following user interface design elements: (1) a "for all" button at the beginning of a row of buttons which if selected will cause all buttons in that row to select simultaneously; (2) display of related physical examination findings spatially close to one another in the user interface, for example with related physical examination findings all appearing as buttons in the same row; (3) a "left-right" button which if selected will display another adjacent button on the left and another adjacent button on the right for the purpose of indicating which side(s) of the body a finding appears on; (4) a lung sounds widget which is organized with six panels, one panel for each lobe of the lung, and within each panel displaying buttons for lung sounds such as wheezes, rales, or rhonchi; (5) an abdominal exam widget which is organized with 4 panels for the 4 quadrants of the abdomen or 9 panels for the 9 sections of the abdomen, and within each panel displaying buttons for abdominal findings such as tenderness, rebounding, or guarding; (6) a pulses widget which is organized to allow the user to select a pulse location (such as brachial, radial, ulnar, or dorsalis pedis), a pulse side (right or left), and a pulse strength (such as 0, 1+, 2+, 3+, 4+); and (7) a reflexes widget which is organized to allow the user to select a reflex location (such as biceps, brachioradialis, triceps, patellar, ankle jerk, plantar), a reflex side (right or left), and a reflex strength (such as 0, 1+, 2+, 3+, 4+).

According to another aspect, a method includes rendering a user interface for a medical note, which includes any of the following user interface design elements: (1) buttons which when selected are colorized based on whether the button text indicates a healthy state or a diseased state, for example green for a healthy state and red for a diseased state; (2) placement of "yes" and "no" buttons on opposites sides of a word or phrase describing a disease, symptom, condition, or physical finding; (3) organization of a plan for a patient's medical care with specific fields for differential diagnosis, prescriptions, procedures, and/or referrals, for each chief complaint separately; and (4) display of questions within the medical note interface that enable the user to record information that can be used as the label when training machine learning models, such as questions about whether a patient will be sent to the emergency department or hospitalized.

According to another aspect, a method includes a computing device comprising at least one processor and memory, where the computing device is configured to receive a plurality of response prompts for interacting with a subject and construct a data structure including a set of nodes. Each of the nodes corresponds to one of the response prompts. The nodes are linked. Each link is traversable based on a response to a response prompt at the respective node. The computing device is also configured to receive one or more responses to one or more response prompts of the set of nodes, use the one or more responses to traverse the links, and construct a narrative of an interaction with a subject based on the traversal of the links and the one or more responses to the one or more response prompts at one or more nodes.

According to another aspect, a method includes a computing device comprising at least one processor and memory, where the computing device is configured to provide a data structure including a set of nodes. Each of the nodes corresponds to a response prompt. The nodes are linked. Each link is traversable based on a response to a response prompt at the respective node. The computing device is also configured to receive one or more responses to one or more response prompts of the set of nodes, use the one or more responses to traverse the links, and construct a narrative of an interaction with a subject based on the traversal of the links and the one or more responses to the one or more response prompts at one or more nodes. Further, the computing device is configured to provide a user interface configured to present the narrative.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical endpoint by providing that a given value may be "slightly above" or "slightly below" the endpoint without affecting the desired result.

The use herein of the terms "including," "comprising," or "having," and variations thereof is meant to encompass the elements listed thereafter and equivalents thereof as well as additional elements. Embodiments recited as "including," "comprising," or "having" certain elements are also contemplated as "consisting essentially of" and "consisting" of those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a range is stated as between 1%-50%, it is intended that values such as between 2%-40%, 10%-30%, or 1%-3%, etc. are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

The functional units described in this specification have been labeled as computing devices. A computing device may be implemented in programmable hardware devices such as processors, digital signal processors, central processing units, field programmable gate arrays, programmable array logic, programmable logic devices, cloud processing systems, or the like. The computing devices may also be implemented in software for execution by various types of processors. An identified device may include executable code and may, for instance, comprise one or more physical or logical blocks of computer instructions, which may, for instance, be organized as an object, procedure, function, or other construct. Nevertheless, the executable of an identified device need not be physically located together but may comprise disparate instructions stored in different locations which, when joined logically together, comprise the computing device and achieve the stated purpose of the computing device. In another example, a computing device may be a server or other computer located within a retail environment and communicatively connected to other computing devices (e.g., POS equipment or computers) for managing accounting, purchase transactions, and other processes within the retail environment. In another example, a computing device may be a mobile computing device such as, for example, but not limited to, a smart phone, a cell phone, a pager, a personal digital assistant (PDA), a mobile computer with a smart phone client, or the like. In another example, a computing device may be any type of wearable computer, such as a computer with a head-mounted display (HMD), or a smart watch or some other wearable smart device. Some of the computer sensing may be part of the fabric of the clothes the user is wearing. A computing device can also include any type of conventional computer, for example, a laptop computer or a tablet computer. A typical mobile computing device is a wireless data access-enabled device (e.g., an iPHONE® smart phone, a BLACKBERRY® smart phone, a NEXUS ONE™ smart phone, an iPAD® device, smart watch, or the like) that is capable of sending and receiving data in a wireless manner using protocols like the Internet Protocol, or IP, and the wireless application protocol, or WAP. This allows users to access information via wireless devices, such as smart watches, smart phones, mobile phones, pagers, two-way radios, communicators, and the like. Wireless data access is supported by many wireless networks, including, but not limited to, Bluetooth, Near Field Communication, CDPD, CDMA, GSM, PDC, PHS, TDMA, FLEX, ReFLEX, iDEN, TETRA, DECT, DataTAC, Mobitex, EDGE and other 2G, 3G, 4G, 5G, and LTE technologies, and it operates with many handheld device operating systems, such as PalmOS, EPOC, Windows CE, FLEXOS, OS/9, JavaOS, iOS and Android. Typically, these devices use graphical displays and can access the Internet (or other communications network) on so-called mini- or micro-browsers, which are web browsers with small file sizes that can accommodate the reduced memory constraints of wireless networks. In a representative embodiment, the mobile device is a cellular telephone or smart phone or smart watch that operates over GPRS (General Packet Radio Services), which is a data technology for GSM networks or operates over Near Field Communication e.g. Bluetooth. In addition to a conventional voice communication, a given mobile device can communicate with another such device via many different types of message transfer techniques, including Bluetooth, Near Field Communication, SMS (short message service), enhanced SMS (EMS), multi-media message (MMS), email WAP, paging, or other known or later-developed wireless data formats. Although many of the examples provided herein are implemented on smart phones, the examples may similarly be implemented on any suitable computing device, such as a computer.

An executable code of a computing device may be a single instruction, or many instructions, and may even be distributed over several different code segments, among different applications, and across several memory devices. Similarly, operational data may be identified and illustrated herein within the computing device, and may be embodied in any suitable form and organized within any suitable type of data structure. The operational data may be collected as a single data set, or may be distributed over different locations including over different storage devices, and may exist, at least partially, as electronic signals on a system or network.

The described features, structures, or characteristics may be combined in any suitable manner in one or more embodiments. In the following description, numerous specific details are provided, to provide a thorough understanding of embodiments of the disclosed subject matter. One skilled in the relevant art will recognize, however, that the disclosed subject matter can be practiced without one or more of the specific details, or with other methods, components, materials, etc. In other instances, well-known structures, materials, or operations are not shown or described in detail to avoid obscuring aspects of the disclosed subject matter.

As used herein, the term "memory" is generally a storage device of a computing device. Examples include, but are not limited to, read-only memory (ROM) and random access memory (RAM).

The device or system for performing one or more operations on a memory of a computing device may be a software, hardware, firmware, or combination of these. The device or the system is further intended to include or otherwise cover all software or computer programs capable of performing the various heretofore-disclosed determinations, calculations, or the like for the disclosed purposes. For example, exemplary embodiments are intended to cover all software or computer programs capable of enabling processors to implement the disclosed processes. Exemplary embodiments are also intended to cover any and all currently known, related art or later developed non-transitory recording or storage mediums (such as a CD-ROM, DVD-ROM, hard drive, RAM, ROM, floppy disc, magnetic tape cassette, etc.) that record or store such software or computer programs. Exemplary embodiments are further intended to cover such software, computer programs, systems and/or processes provided through any other currently known, related art, or later developed medium (such as transitory mediums, carrier waves, etc.), usable for implementing the exemplary operations disclosed below.

In accordance with the exemplary embodiments, the disclosed computer programs can be executed in many exemplary ways, such as an application that is resident in the memory of a device or as a hosted application that is being executed on a server and communicating with the device application or browser via a number of standard protocols, such as TCP/IP, HTTP, XML, SOAP, REST, JSON and other sufficient protocols. The disclosed computer programs can be written in exemplary programming languages that execute from memory on the device or from a hosted server, such as BASIC, COBOL, C, C++, Java, Pascal, or scripting languages such as JavaScript, Python, Ruby, PUP, Perl, or other suitable programming languages.

As referred to herein, the terms "computing device" and "entities" should be broadly construed and should be understood to be interchangeable. They may include any type of computing device, for example, a server, a desktop computer, a laptop computer, a smart phone, a cell phone, a pager, a personal digital assistant (PDA, e.g., with GPRS NIC), a mobile computer with a smartphone client, or the like.

As referred to herein, a user interface is generally a system by which users interact with a computing device. A user interface can include an input for allowing users to manipulate a computing device, and can include an output for allowing the system to present information and/or data, indicate the effects of the user's manipulation, etc. An example of a user interface on a computing device (e.g., a mobile device) includes a graphical user interface (GUI) that allows users to interact with programs in more ways than typing. A GUI typically can offer display objects, and visual indicators, as opposed to text-based interfaces, typed command labels or text navigation to represent information and actions available to a user. For example, an interface can be a display window or display object, which is selectable by a user of a mobile device for interaction. A user interface can include an input for allowing users to manipulate a computing device, and can include an output for allowing the computing device to present information and/or data, indicate the effects of the user's manipulation, etc. An example of a user interface on a computing device includes a graphical user interface (GUI) that allows users to interact with programs or applications in more ways than typing. A GUI typically can offer display objects, and visual indicators, as opposed to text-based interfaces, typed command labels or text navigation to represent information and actions available to a user. For example, a user interface can be a display window or display object, which is selectable by a user of a computing device for interaction. The display object can be displayed on a display screen of a computing device and can be selected by and interacted with by a user using the user interface. In an example, the display of the computing device can be a touch screen, which can display the display icon. The user can depress the area of the display screen where the display icon is displayed for selecting the display icon. In another example, the user can use any other suitable user interface of a computing device, such as a keypad, to select the display icon or display object. For example, the user can use a track ball or arrow keys for moving a cursor to highlight and select the display object.

The display object can be displayed on a display screen of a mobile device and can be selected by and interacted with by a user using the interface. In an example, the display of the mobile device can be a touch screen, which can display the display icon. The user can depress the area of the display screen at which the display icon is displayed for selecting the display icon. In another example, the user can use any other suitable interface of a mobile device, such as a keypad, to select the display icon or display object. For example, the user can use a track ball or times program instructions thereon for causing a processor to carry out aspects of the present disclosure.

As referred to herein, a computer network may be any group of computing systems, devices, or equipment that are linked together. Examples include, but are not limited to, local area networks (LANs) and wide area networks (WANs). A network may be categorized based on its design model, topology, or architecture. In an example, a network may be characterized as having a hierarchical internetworking model, which divides the network into three layers: access layer, distribution layer, and core layer. The access layer focuses on connecting client nodes, such as workstations to the network. The distribution layer manages routing, filtering, and quality-of-server (QoS) policies. The core layer can provide high-speed, highly-redundant forwarding services to move packets between distribution layer devices in different regions of the network. The core layer typically includes multiple routers and switches.

FIG. 1A illustrates a block diagram of a system 100 for constructing a narrative of an interaction with a subject and for presenting the narrative in accordance with embodiments of the present disclosure. Referring to FIG. 1A, the system includes a computing device 102 of a notetaker 104 and a computing device 106 of a physician 108. In this example, the notetaker 104 may be a physician's assistant who is interviewing a patient 110 prior to the patient's 110 appointment with the physician 108. During the interview, the notetaker 104 may interact with the computing device 102 for receiving response prompts to present to the patient 110 and for receiving responses to the response prompts from the patient 110. For example, a display 112 of the computing device 102 may display to the notetaker 104 a series of response prompts (e.g., questions or multiple choice prompts) to present to the patient 110. Examples of the notetaker 104 presenting the response prompts to the patient 110 includes, but are not limited to, showing the display with the response prompts to the patient 110, or speaking the response prompts to the patient 110, or speaking an alternative phrasing of the response prompts with the same meaning to the patient 110. As the response prompts are presented to the patient 110, the patient 110 may in turn provide a response to each response prompt. The responses may be received and suitably stored at the computing device 102 or in the cloud. As described in further detail herein, a response may be used to determine one or more subsequent response prompts for presentation to the patient 110. Further, a narrative of the interaction with the patient 110 may be constructed based on the responses. This narrative can include information about the patient's current condition and medical history. The narrative may be constructed on one or more computing devices. For example, the narrative may be constructed on the patient's device, the physician's device, a device in the cloud, and/or combinations thereof. Subsequently, the narrative may be communicated to the computing device 106 via one or more networks 114 such that the narrative may be presented to the physician 108 via a user interface of the computing device 106.

FIG. 1B illustrates a block diagram of a system 100 for construction a narrative of an interaction with a subject and for presenting the narrative in accordance with embodiments of the present disclosure. Referring to FIG. 1B, the system includes a computing device 102 used by a patient 110 and a computing device 106 of a physician 108. Before the patient 110 has an appointment with the physician 108, the patient 110 may interact with the computing device 102 to receive response prompts and to enter responses to the response prompts. A display 112 of the computing device 102 may display to the patient 110 a series of response prompts (e.g., questions or multiple choice prompts). As the response prompts are presented to the patient 110, the patient 110 may in turn provide a response to each response prompt. The computing device 102 may be a device belonging to the patient, a device provided by a medical facility, or another device. The responses may be received at the computing device 102, and suitably stored at the computing device 102 and/or in the cloud. As described in further detail herein, a response may be used to determine one or more subsequent response prompts for presentation to the patient 110. Additionally, a narrative of the interaction with the patient 110 may be constructed based on the responses. This narrative can include information about the patient's current condition and medical history. Subsequently, the narrative may be communicated to the computing device 106 via one or more networks 114 such that the narrative may be presented to the physician 108 via a user interface of the computing device 106.

FIG. 1C illustrates a block diagram of a system 100 for construction of a narrative of an interaction with a subject and for presenting the narrative in accordance with embodiments of the present disclosure. Referring to FIG. 1C, the system includes a computing device 102 used by a physician 108. During the interview, the physician 108 may interact with the computing device 102 to receive response prompts to present to the patient 110. The physician may receive responses to the response prompts from the patient 110. For example, a display 112 of the computing device 102 may display to the physician 108 a series of response prompts (e.g., questions or multiple choice prompts) to present to the patient 110. Examples of the physician 108 presenting the response prompts to the patient 110 include, but are not limited to, showing the display with the response prompts to the patient 110, or speaking the response prompts to the patient 110, or speaking an alternative phrasing of the response prompts with the same meaning to the patient 110. As the response prompts are presented to the patient 110, the patient 110 may in turn provide a response to each response prompt. The responses may be received and suitably stored at the computing device 102. As described in further detail herein, a response may be used to determine one or more subsequent response prompts for presentation to the patient 110. A narrative of the interaction with the patient 110 may be constructed based on the responses. This narrative can include information about the patient's current condition and medical history. The narrative may be constructed on one or more computing devices. For example, the narrative may be constructed on the physician's device, a device in the cloud, and/or combinations thereof. Subsequently, the narrative may be presented to the physician 108 via a user interface of the computing device 102.

In accordance with embodiments, the notetaker's computing device 102 or a device in the cloud may include a narrative build manager 116. The functionality of the narrative build manager 116 described herein may be implemented by hardware, software, firmware, or combinations thereof. For example, the narrative build manager 116 may be implemented by memory 118 and one or more processors 120. The manager 116 may use a data structure including a set of nodes. Each node can correspond to a corresponding one of multiple response prompts for interacting with a subject (e.g., the patient 110). The nodes can be linked, and each link can be traversable based on a response to a response prompt at the respective node. The manager 116 is configured to receive one or more responses to one or more response prompts of the set of nodes, to use the one or more responses to traverse the links, and to construct a narrative of an interaction with a subject based on the traversal of the links and the one or more responses to the one or more response prompts at one or more nodes. Further, the narrative may be communicated to the physician's computing device 106 for presentation to the physician 108.

FIG. 2 illustrates a flowchart of a method for constructing a narrative of an interaction with a subject and for presenting the narrative in accordance with embodiments of the present disclosure. The method is described by example as being implemented by the system 100 shown in FIG. 1, but it should be understood that the method may be implemented by any suitable system.

Referring to FIG. 2, the method includes receiving 200 response prompts for interacting with a subject. Response prompts can include, but are not limited to questions and/or multiple choice prompts. One or more of the nodes may be associated with a template sentence in addition to a response prompt. For example, a node may be associated with a response prompt "When did the symptoms start?" and with a template sentence "The symptoms started on _____." The response prompts can each be a request for health-related information about the subject for use in building a narrative of the subject's health based on an interview of the subject. In examples, response prompts can include prompts for input of the subject's history of present illness, medication usage, allergies, family health history, past medical history, surgical history, social history, physical examination findings, review of systems, and/or discussion and plan.

In accordance with embodiments, response prompts may be input by a user for use in constructing a linked data structure. For example, a user of the computing device 102 may use an application residing thereon to input response prompts. Further, the user may input an indication of an ordering of and an interrelation of the response prompts. Construction of the data structure may include linking the nodes based on the received user input that indicates the ordering of and an interrelation of the response prompts. Further, the user may input a template sentence for each node in addition to a response prompt for each node. A data structure may be, for example, a data tree structure. Nodes may include a parent node and two or more child nodes that are each linked to the parent node, and where the links between the parent node and the child nodes are traversable based on a response to a response prompt at the parent node. The user may input information about the nature of the responses that induce traversal from a parent node to a child node.

The method of FIG. 2 includes constructing 202 a data structure including a set of nodes. Each node corresponds to one of the response prompts. The nodes are linked, and each link is traversable based on a response to a response prompt at the respective node. The computing device 102 or another computing device may construct a data structure including a set of nodes in which each node corresponds to one of the response prompts. The nodes may be linked and traversable based on a response to a response prompt at the respective node.

The method of FIG. 2 includes receiving 204, at a narrative build manager, one or more responses to one or more response prompts of the set of nodes. The notetaker's computing device 102 can receive, via a user interface 122, responses to one or more of the response prompts. The responses may be input by the notetaker 104 by use of the user interface 122. For example, the notetaker 104 may interview the patient 110 by presenting a series of the response prompts to the patient 110. The responses may also be input by the patient 110.

The method of FIG. 2 includes using 206, at the narrative build manager, the response(s) to traverse the links. The ordering of the presentation of the response prompts can be based on the responses given by the patient 110 and input into the computing device 102. Particularly, the manager 116 can traverse the links between nodes based on the responses, thus presentation of a series of response prompts can be different depending on the responses.

The method of FIG. 2 includes constructing 208, at the narrative build manager, a narrative of an interaction with a subject based on the traversal of the links and the response(s) to the response prompt(s) at the nodes. The manager 116 can construct a narrative of an interaction with the patient 110 based on the traversal of the links and the responses to the response prompts at the nodes. The narrative can include text in the form of multiple sentences. The manager 116 can construct the sentences based on a structure linking the nodes and/or based on the responses to the response prompts at the nodes. Further, the narrative can include text in the form of multiple paragraphs. The manager 116 can construct the paragraphs based on a structure linking the nodes and/or based on the responses to the response prompts at the nodes. The manager 116 may be configured to construct a sentence based on a template sentence and a received response to the response prompt for that node.

The method of FIG. 2 includes presenting 210 the narrative via a user interface. The constructed narrative may be constructed at the notetaker's computing device 102 and may be stored in memory 118 and presented via the display 112 of the notetaker's computing device 102. Or, for example, the manager 116 may communicate the narrative to the physician's computing device 106 via the network(s) 114. The computing device 106 may suitably store and present the narrative to the physician 108.

In accordance with embodiments, systems and methods disclosed herein may be implemented via a website accessible by a web browser residing on a computing device that has Internet access. Systems and methods disclosed herein may also be implemented via a desktop application or mobile device application. In an example, the website or application can have functionality for implementing an intelligent medical notes assistant. The assistant can be used to generate a medical note in plain text, rich text, or another file format. The generated medical note can be copy-pasted into any electronic medical record. By use of the medical notes assistant, medical note writing can be accelerated and also well-organized data can be obtained for use in building machine learning applications. Various medical note sections may be included in a generated note, including, but not limited to, the history of present illness (HPI), past medical history (PMH), past surgical history (PSH), medications, allergies, family history (FH), social history (SH), review of systems (ROS), physical examination (PE), and discussion and plan.

In an example, a history of present illness section can be a disease-specific part of the note, for example describing why the patient sought medical care today. The history of present illness section and other note sections can be generated using disease-specific medical knowledge graphs. For example, there is a knowledge graph related to "headache" and another knowledge graph related to "chest pain." In an example, each node in the knowledge graph can be a question. For example, the question "Are you dizzy?" is the root node of the "Dizziness" knowledge graph. A node can lead to more nodes ("children") depending on the patient's response. For example, if a node question is "Are you dizzy?" and the patient's response is "Yes" then that leads to the child nodes (a.k.a. "follow-up questions" or "child questions") "When did the dizziness start?" "Do you feel the room spinning around you?" "Do you feel nauseated?" and other child nodes.

In accordance with embodiments, a system disclosed herein can provide basic knowledge graphs such as graphs for chest pain, headache, shortness of breath, and numerous other complaints, diseases, symptoms, and/or conditions.

Example Workflow with Pre-Interview of Patient: In accordance with embodiments, an example workflow may begin with pre-interview of a patient so that a doctor receives a generated note before they have seen the patient. This reduces the amount of time that the doctor must spend collecting basic information and thereby allows the face-to-face time between the doctor and patient to be focused on more complex medical interviewing, responding patient questions, and physical examination. Example steps follow:

1) Clinic requests that a patient response a system questionnaire before the appointment. A system questionnaire may replace paper forms, may replace competing patient questionnaire software, or may provide a new service for a clinic that previously did not use any pre-appointment questionnaires.
2) Patient fills out the questionnaire using a desktop computer or mobile device, either at home or in the clinic.
3) Patient submits completed questionnaire, which is routed to the doctor.
4) Doctor opens questionnaire:
   To view the generated note
   To edit the text of the generated note directly
   To use the system's interface to edit the patient's information
5) At the end of the patient visit, the doctor copies the generated note into their electronic medical record. Note that if the patient used a template created by their doctor, then the generated note may be in the exact format that the doctor specified.

Example Workflow During Interview of Patient: In accordance with embodiments, in another example user workflow a clinician can use the questionnaire while they are interviewing a patient, for example by clicking buttons, making selections from menus, or typing in the patient's responses to the questions. This workflow can have the goals of accelerating the process of gathering information during a patient interview, assisting in an interview for a rare disease by reminding the doctor of what questions to ask for that disease, or assisting in medical student education by reminding the medical student of what questions to ask for that disease. Example steps follow:

1) When a patient arrives, the doctor opens a questionnaire for that patient.
2) The doctor fills out the questionnaire by verbally asking the patient the questions and filling in the responses using the system's efficient user interface.
3) The doctor copies the final generated note out of the system's product and into the electronic medical record.

A description of an example website in accordance with embodiments of the present disclosure is provided in the following table Example Website Description Throughout, the word "template" or "questionnaire" may refer to a knowledge graph data structure, a data structure of linked nodes, and/or another data structure that specifies the content of a particular note section.

| Page | Description |
| --- | --- |
| Landing page | This page may include pinned templates, frequently accessed templates, pinned template combinations, and/or access to previously written notes. This page may include buttons or links that allow a user to create a new blank note, edit an existing note, create a new note template, and/or edit an existing note template. |
| Note browsing page | This page enables the user to browse notes that they have previously created. These notes may be completed or in progress. |
| Template browsing page | This page enables the user to browse different templates, such as templates for different diseases related to the History of Present Illness section, templates for different Physical Exam sections, and/or templates for different Review of Systems sections. |
| Login page | On this page the user inputs their username and password. Single-factor or multifactor authentication may be used. |
| Account page | On this page the user can enter or update personal information about themselves such as first name, last name, phone number, address, email address, preferred pronouns, location, payment information. and associated medical facilities or clinicians. |
| About us | On this page the user can read about the company's mission and/or team. |
| Contact us | On this page the user can send the company feedback, suggestions for how to improve the product, comments, or questions. |

-continued

| Page | | Description |
|---|---|---|
| Recommendation | | This feature enables the user to recommend the product to a friend. |
| Create Note | HPI | History of Present Illness. This section focuses on why the patient is in a medical facility today. This section uses disease-related knowledge graphs either provided by Cydoc or created by a user. The user selects which diseases, conditions, and/or symptoms are relevant to the patient's visit today. Then the knowledge graphs for each of those selected diseases, conditions, and/or symptoms are used to display questions to the user in a dynamic way through a user interface. The questions that are displayed may change depending on the user's responses. This process is inspired by the way in which a doctor's questions may change depending on a patient's responses to previous questions.<br>The History of Present illness includes a carefully designed user interface to allow efficient responding of questions, and display of questions is different depending on the question type. |
| | PMH | Past Medical History: This section enables a user to enter information about a patient's past medical history, including past diagnoses, yes or no for whether the patient has the diagnosis, onset of the diagnosis, whether the condition has resolved, date of resolution, and/or comments. |
| | PSH | Past Surgical History: This section enables a user to enter information about a patient's past surgical history, including the procedure name, the procedure date, and/or comments. |
| | Meds | Medications and Supplements: This section enables a user to enter information about a patient's medications, including the medication name, start date, whether the patient is currently taking the medication, end date, schedule, dose, reason for taking, side effects, and/or comments. |
| | Allergies | Allergies: This section enables a user to enter information about a patient's allergies, including the inciting agent, type of reaction, and/or comments. |
| | FH | Family History: This section enables a user to enter information about their family history, including diagnoses, whether the patient's family includes anyone with that diagnosis, which family member(s) had or have the condition, whether the condition was the cause of death for each family member, and/or comments. |
| | SH | Social History: This section enables a user to enter information about a patient's social history, including tobacco use, alcohol use, recreational drug use, living situation, employment, diet, and exercise. For substance user, the user can enter information about the specific kinds of substances used, the quantity of substances used, the duration of time substances have been used, the method by which substances are used, whether the patient is interested in quitting, and/or whether the patient has tried to quit before. |
| | ROS | Review of Systems: This section enables a user to enter whether or not a patient is experiencing particular symptoms. The symptoms are organized according to body system or other topical grouping. |
| | PE | Physical Exam: This section enables a user to enter information about a patient's physical examination findings.<br>The physical exam includes a carefully designed user interface to allow efficient recording of normal and abnormal findings by clicking on buttons, using widgets, and/or using auto-populating drop-down menus.<br>Physical exam findings that have a particular side (for example, right vs. left eye, right vs. left ear) are displayed using buttons that expand to include a "right" indicator and a "left" indicator when clicked, so that the user may specify the side(s) of the physical exam finding. Custom widgets enable efficient entering of lung sounds, abdominal quadrant findings, heart murmurs, tendon reflexes, and pulses. Buttons may be colorized according to whether a physical exam finding is normal or abnormal, for example green for normal and red for abnormal. |
| | Plan | Discussion and Plan<br>This section is important for future machine learning applications. This is also an important section in a medical note. Here the user specifies what they think the diagnosis is, and they describe the treatment plan.<br>Fields may include:<br>Differential Diagnosis: here the user can enter what they think the differential diagnosis is and why. For example, the differential diagnosis for headache might be, "Migraine, Tension Headache, Dehydration."<br>Plan (Medications): the user can write down detailed information about any medications they intend to prescribe to treat the patient's condition, including information about the medication |

-continued

| Page | Description |
|---|---|
| | dose and schedule.<br>Plan (Procedures/Services): the user can write down what procedures (e.g. appendectomy, electrocardiogram) they intend to order to treat the patient's condition.<br>Referrals/Consults: the user can write down if the patient should see any specialists, go to a hospital, etc.<br>Example additional fields (which are not usually part of a Discussion and Plan but which are included for downstream machine learning purposes):<br>How sick is the patient on a scale of 1 (healthy) to 10 (critically ill)?<br>Will the patient be sent to the emergency department?<br>Will the patient be admitted to the hospital?<br>What other questions were asked to the patient that were not part of the existing template?<br>Additional fields beyond the ones listed may be included as well. |
| Generate Note | This page summarizes the entire note in free text, rich text, or another format that enables the user to copy and paste the generated note into an electronic medical record or transfer the generated note into an electronic medical record in some other manner. The Generate Note section has various parts:<br>The History of Present illness section is displayed as free text that is generated based on user responses to response prompts, template sentences, machine learning processing steps, and/or rule-based processing steps.<br>Additional data about the patient may be represented in text using whitespace to make sure it displays as a table, in rich text using a table format, or in free text. The point of the "Generate Note" functionality is to allow the user to copy all of the note information from the user interface into whatever electronic medical record their hospital or clinic is using. |
| Create Template: History of Present Illness | The Create Template: History of Present Illness feature enables a user to create a custom template for a particular disease, condition, or symptom. This custom template may be a knowledge graph that can be used in the History of Present Illness section of the note.<br>The feature provides a graphical user interface that allows a user to design and input a custom knowledge graph. The user inputs the question text, question type, template sentence, question order, and question relationships. In addition to creating new templates from scratch, users can also edit templates that were previously created by themselves, by others, or by Cydoc. |
| Create Template: Physical Exam | On this page a user can create a custom template for a Physical Exam section. The user can specify the words that should appear on or within buttons, widgets, and/or auto-populating dropdown menus. They can specify whether particular buttons correspond to normal or abnormal physical exam findings, which can change the display color of these buttons. They can specify whether particular buttons correspond to findings that can be found on the left and/or right side of the body, in which case the button may include the functionality of popping out a left indicator or right indicator when it is first tapped so that the user may select on which side(s) of the body the finding is observed. The user can specify the locations on the page that different user interface elements should appear, and/or the relative ordering in which different user interface elements should appear. |
| Create Template: Review of Systems | On this page a user can create a custom template for a Review of Systems section. The user can specify which sections to include, and what the title of each section should be. They can specify what words should appear within each section. |
| Tutorial | This page provides a written, drawn, photographed, and/or video explanation of how to use the product: how to fill out a note, what the generated note looks like, how to use the Create Template functionality, what the different question types mean, etc. |

Multiple Devices and/or Users: It can be assumed that people may use this product across multiple devices and/or users even for the same note. For example, a doctor may fill out one note partially on their phone and partially on two different desktop computers in different parts of the hospital. Automatic saving of data may be enabled to ensure no data is lost when a user transitions between devices. It can be assumed that people may also use this product across a single device; for example, a doctor may fill out one note entirely on a single hospital computer.

Proper Display on Varying Screen Sizes: It can be assumed that people may use this product on any computing device, including desktop computers and mobile devices. The website or application may display differently on mobile devices than desktop computers, with custom interfaces optimized for smaller or larger screens respectively.

Numerous Uses: Systems disclosed herein can be used in human medicine, veterinary medicine, social work, psychology, physical therapy, occupational therapy, chiropractic, optometry, and all professions in which a patient (human or animal) has a physical, mental, or social issue that must be evaluated through structured questioning and summarized in a written note. A user may be a patient, doctor, nurse, physician assistant, nurse practitioner, veterinarian, dentist, social worker, psychologist, physical therapist, student, secretary, and/or any other individual who interacts with a patient. Systems disclosed herein can also be used in clinical trials, medical research, and other research enterprises that require collecting structured information and summarizing it.

Knowledge Graph: Systems disclosed herein can gather information through a knowledge graph that enables dynamic patient questioning as well as through customized interfaces for specific note sections. In accordance with embodiments, dynamic patient interviewing can be built or constructed using a knowledge graph with a unique structure. The knowledge graph may consist of disease, condition, or symptom-specific trees that can link to one another. For example, the "Chest Pain" tree can link to the "Aortic Aneurysm" or "Pulmonary Embolism" trees. The system may come with many disease, condition, and symptom-specific trees built in. In accordance with embodiments, each disease, condition, or symptom-specific tree may be associated with the following elements:

Body System: this indicates the body system related to the disease or condition. E.g. "Cardiovascular," "Respiratory," "Gastrointestinal" etc.

Category: this indicates the name of the disease or condition, e.g. "Chest Pain", "Headache", "Diabetes," etc.

Example Question Nodes (Response Prompt Nodes) of Knowledge Graph Data Structure. A knowledge graph can be created from Question Nodes. Each Question Node of the knowledge graph may be defined by some or all of the following attributes:

| Attribute | Example Data Type | Description |
|---|---|---|
| ID | string | An alphanumeric identifier that uniquely identifies the node |
| Root Indicator | 0 or 1 | If equal to 1, indicates that this node is the root of a tree. If equal to 0, indicates that this node is not the root of a tree. |
| Question/ Response Prompt | string | The question text itself. For example, "Did the chest pain come on suddenly?" "Do you have high blood pressure?" "Have you had any recent operations on your heart or arteries?" or "Select any of the following symptoms you are experiencing: headache, drowsiness, chest pain, shortness of breath." |
| Question Type/ Response Prompt Type | string | There are at least 13 basic question types which are described in more detail below in the "Question Types" section. |
| Body System | string | A string describing what body system is related to this node. For example, the body system may be one of the body systems in this list: Cardiovascular/Hematologic, Dermatologic, Endocrine, Gastrointestinal, General/Lifestyle, Genitourinary, HEENT, Immune, Neurologic/Psychiatric, Pain, and Respiratory. |
| Category | string | A string describing more specifically what disease, symptom, or condition is related to this node. For example, the category could be ALLERGY, ANXIETY, or AORTIC_ANEURYSM. |
| Creation Time | DateTime | A timestamp for when the node was created. |
| Note Section | string | A string describing what note section relates to this node. For example, the note section could be "HPI" (for History of Present Illness) or "ROS" (for Review of Systems). |
| Patient View | string | A string with a patient-friendly description of the Category. For example, "Feeling Anxious" for Category ANXIETY. |
| Doctor View | string | A string with a doctor-targeted description of the Category. For example, "Generalized Anxiety Disorder" for Category "ANXIETY." |
| Response Leading to More Questions | string | Specifies what kind of response triggers traversal to the child nodes of this node. For example, if the Response Leading to More Questions is "Yes" then this means a "Yes" response will cause the algorithm to ask the questions specified as child nodes. |
| Child Nodes | list of strings | The alphanumeric identifiers of the nodes considered children of this node. |
| Template Sentence | string or list of strings | A template sentence (or set of template sentences) that will be used in the generation of the initial version of the medical note. For example, "The patient has a family history of RESPONSE" may be the template sentence for the question "Does the patient have a family history of diabetes or kidney disease?" If the patient selects "diabetes" then the resulting sentence will be "The patient has a family history of diabetes." |
| Template Sentence for Yes | string | A template sentence that is relevant if this is a yes or no question and the answer is yes. For example, "The patient has a headache." |
| Template Sentence for No | string | A template sentence that is relevant if this is a yes or no question and the answer is no. For example, "The patient does not have a headache." |
| Doctor Created | string | The unique Doctor ID of the doctor that created this question. If Cydoc created this question then Doctor Created will indicate that Cydoc created the question. |

Example Additional Nodes: To enable computationally efficient querying of the knowledge graph data structure, additional specialized kinds of nodes may be included. Examples of additional specialized kinds of nodes are Doctor Nodes and Category Nodes.

Doctor Nodes (or "Author Nodes"): As an example, Doctor Nodes may be included in a knowledge graph in addition to Question Nodes. A Doctor Node connects to one or more Question Nodes. A Doctor Node is associated with a doctor attribute that stores information about the doctor that created one or more Question Nodes. A Doctor Node may connect to any Question Node for which the doctor attribute of the Doctor Node matches the doctor attribute of the Question Node. If a "root node" indicates the root node of all Question Nodes related to a particular Category, then a Doctor Node may connect to all "root nodes" for which the doctor attribute of the root node matches the doctor attribute of the Doctor Node. A Doctor Node may be associated with some or all of the following attributes: User ID (a unique identifier of the doctor), Creation Time (a timestamp for when a doctor was created), Name (the name of the doctor), Graph ID (an identifier for a graph), Roots (identifiers for the roots of all the graphs that a doctor has created), and/or Questions (identifiers for all the questions that a doctor has created). One use of Doctor Nodes is to increase the speed at which all the Question Nodes created by a particular doctor can be retrieved. Doctor Nodes can enable more efficient querying of Question Nodes according to the identity of the doctor who created those Question Nodes. Note that the use of the word "Doctor" does not restrict this description only to physician users; here a "Doctor" refers to any user of the product regardless of their professional background.

Category Nodes: As an example, Category Nodes may be included in a data structure in addition to Question Nodes.

Category Nodes may be created from a set of all unique categories retrieved from the Category attribute of Question Nodes in a knowledge graph. Category Nodes may also be created from a set of all unique elements retrieved from any attribute of Question Nodes in a knowledge graph. A Category Node may be restricted to only connect to other Category Nodes. If "disease subgraph" refers to a collection of Question Nodes that all share the same disease Category and their connections to each other, then a purpose of Category Nodes may be to exemplify conceptual connections between different disease subgraphs within the knowledge graph. The Category Nodes may reflect what disease categories are connected to one another, which in turn may enable more efficient implementation of truncated graph traversal by category. For example, if a user requests all of the "Chest Pain" Question Nodes, the Category Nodes may enable efficient identification of which other categories are connected to chest pain (such as pain, shortness of breath, pulmonary embolism, pneumothorax, and/or diet). In turn, the categories connected to each of these categories can be identified (e.g. all categories connected to pneumothorax) and it may become possible to easily decide "how far out to go" when traversing disease categories. A limit may be set on "how far out to go" for a category. A Category Node may be defined by the following attributes: Category Node ID (a unique identifier), Category (a string describing the category), Creation Time (time stamp for when a node was created), and/or Child Categories (a list of categories that this category node is related to, for example a list of all categories that this category is connected to according to Question Node connectivity). Note that Category Nodes may be created based on the disease Category attribute of Question Nodes, but Category Nodes could also be created based on any other attribute or collection of attributes of Question Nodes, for example the Patient View, Doctor View, Body System, and/or Note Section.

Example Question Types. Nodes in the knowledge graph may be associated with the attribute "Question Type." In examples, there can be at least 13 different question types, which are displayed differently to the user to enable efficient data collection. When users are creating their own custom knowledge graphs, the user can specify the question type of each question that they write.

Example Question Types

| Question Type | Definition | Example | Display |
|---|---|---|---|
| YES-NO | a yes or no question | "Do you have chest pain?" | Question text followed by a button for "Yes" and a button for "No" |
| CLICK-BOXES | a multiple-choice question for which the user can select all, some, or none of a predefined set of response choices | "Are you suffering any of the following symptoms? headache, dizziness, vision changes" | Question text followed by separate buttons for each of the possible response choices |
| SHORT-TEXT | free-text response | "What happened before you fell?" | Question text followed by a text box |
| LIST-TEXT | list of text responses | "What foods did you eat while traveling?" | Question text followed by multiple short text boxes for the list elements. The user can add additional list elements or can delete existing list elements. In |

-continued

| Question Type | Definition | Example | Display |
|---|---|---|---|
| | | | the user interface, each list element may be implemented using a search-select drop down, such that when a user begins typing they see related answer choices appear which they then have the option to select. |
| NUMBER | numerical value | "How many centimeters is the laceration?" | Question text followed by a box that accepts numerical input |
| SLIDING SCALE | numerical value on a sliding scale | "On a scale of 1 to 10, how would you rate your pain?" | Question text followed by a slider that the user can drag to any number between predefined numerical upper and lower limits. |
| TIME | numerical value plus time units of minutes, hours, days, weeks, months, or years. | "At what age did your child first smile?" | Question text followed by a numerical value box and buttons for the time units. |
| BODY-LOCATION | a question asking about the body location of a particular symptom | "Where is the pain?" | Question text followed by a diagram of the body that the user can click to select different regions. Or, question text followed by buttons for different body locations, organized according to body location. |

In accordance with embodiments, an "Unsure" option may be implemented in instance of "Yes"/"No" options for use when a user is "unsure." Providing an "unsure" option helps avoid circumstances in which a user leaves a question blank or in which a user arbitrarily chooses a "yes" or "no" response when they are truly uncertain.

Example Special Question Types BLANK and POP: It is desirable to reduce repetitive information entry within a single visit. Therefore, to make information gathering as efficient as possible, the product may include special question types in the knowledge graph that enable synchronization between the History of Present Illness section and other topic-specific note sections. These special question types are MEDS-BLANK, MEDS-POP, PMH-BLANK, PMH-POP, PSH-BLANK, PSH-POP, FH-BLANK, and FH-POP. MEDS-BLANK and MEDS-POP enable synchronization between the medications section and the HPI. PMH-BLANK and PMH-POP enable synchronization between the past medical history section and the HPI. PSH-BLANK and PSH-POP enable synchronization between the past surgical history section and the HPI. FH-BLANK and FH-POP enable synchronization between the family history section and the HPI.

When a patient responds to one of these special question types in the "History of Present Illness" section, the information they enter will automatically appear in the appropriate topic-specific section (e.g. "Medications") and vice versa.

"BLANK" means that a custom interface related to the corresponding section is shown, with all entries blank and nothing prepopulated. For example, a MEDS-BLANK question means a blank medications interface is shown. If a patient enters data into a MEDS-BLANK question within the HPI, the Medications section will be synchronized with the data the patient entered.

"POP" means that a custom interface related to the corresponding section is shown, with the identifying column prepopulated according to a list specified in a database. The identifying column could be a medication name, disease name, or procedure name, for example. The interface may additionally include a "Yes/No" option so the user can specify if a particular entry applies to them. Information entered in to the interface will be synchronized with the corresponding topic-specific note section.

In an example for a "POP" question, a MEDS-POP question may be: "Are you taking any of the following medications? metformin, insulin, azithromycin."

The display for that question in the HPI will be a custom medications interface with metformin, insulin, and azithromycin shown.

There will be a Yes/No option associated with each of the medications so that the patient can check "yes" if they are taking the medication and "no" if they are not All medications that the patient is taking (i.e., for which the response is yes) will be synchronized with the table in the Medication section. In an alternative implementations, all medications (i.e., for which the response is yes or no) may be synchronized with the table in the Medications section.

| Question Type | Definition | Example | Display |
| --- | --- | --- | --- |
| PMH-BLANK | Past medical history, blank | "What conditions have you been diagnosed with?" | This will display with a past medical history interface. |
| MEDS-BLANK | Medications, blank | "What medications are you taking?" | This will display with a medications interface. |
| FH-BLANK | Family history, blank | "What conditions have members of your family been diagnosed with?" | This will display with a family history interface. |
| PSH-BLANK | Past surgical history, blank | "What operations or procedures have you undergone?" | This will display with a past surgical history interface. |
| PMH-POP | Past medical history, prepopulated | "Have you ever been diagnosed with any of the following conditions? diabetes, kidney disease, heart attack" | This will display with a past medical history interface, with the prespecified conditions prepopulated. |
| MEDS-POP | Medications, prepopulated | "Are you taking any of the following medications? aspirin, metformin, acetaminophen." | This will display with a medications interface, with the prespecified medications prepopulated. |
| FH-POP | Family history, prepopulated | "Has anyone in your family ever been diagnosed with any of the following conditions? diabetes, kidney disease, heart attack" | This will display with a family history interface, with the prespecified conditions prepopulated. |
| PSH-POP | Past surgical history, prepopulated | "Have you ever undergone the following operations? appendix removal, gallbladder removal" | This will display with a past surgical history interface, with the prespecified conditions prepopulated. |

Example Node Order: Nodes in a knowledge graph may be ordered. Node order may be determined by an attribute of one or more nodes, or node order may be determined by one or more attributes of one or more edges (links between nodes). The attribute(s) that determine node order may be composed of one or more symbols, letters, numbers, and/or another representation. An ordering of Question Nodes can be useful in the generation of text. A sentence may be produced from a Question Node based on the template sentence and the user answer. Multiple sentences may be produced from multiple Question Nodes. The ordering of Question Nodes can determine an ordering of multiple sentences. For example, if one sentence is generated per node, the ordering of nodes may be used to define the ordering of generated sentences.

Node Order per Node Attribute: An ordering of nodes in a knowledge graph may be defined by an attribute assigned to one or more nodes. This Node Order attribute may store a value that indicates an ordering of nodes. For example, if there are three nodes, the first may have a Node Order attribute of "1", the second may have a Node Order attribute of "2", and the third may have a Node Order attribute of "3" which thus defines a numerical ordering of these nodes. For example, if there are two nodes, the first may have a Node Order attribute of "a" and the second may have a Node Order attribute of "b" which thus defines an alphabetical ordering of these nodes.

Node Order per Edge Attribute: An ordering of nodes in a knowledge graph may be defined by one or more attributes assigned to one or more edges. This Edge Order attribute may store a value that indicates an ordering of nodes via indicating an ordering of edges. For example, if there are three nodes referred to by "abc," "def," and "ghi" and "abc" connects to "def" by an edge with Edge Order "1", and "abc" connects to "ghi" by an edge with Edge Order "2", then that defines a numerical ordering of these nodes starting with "abc" and proceeding to "def" and then to "ghi." There may also be multiple edge attributes that define an ordering of edges, for example edge attributes "From Node Order" and "To Node Order." The attribute "From Node Order" can store a value indicating the order of this edge's parent node, while the attribute "To Node Order" can store a value indicating the order of this edge's child node.

One benefit of storing the node order as an attribute or attributes of edges is that this may prevent the need to duplicate nodes any time the node order is changed. In some cases, it may be advantageous to avoid ever deleting nodes because users may want to define custom graphs based on existing nodes, and later deletion of nodes could disrupt these custom user-created graphs. If node order is stored with edges then there is no need to modify nodes when node order changes; only the edges need to be modified to store the new node order. However, if node order is stored as a node attribute, then any time the node order changes, new nodes need to be created with the new node order, even if all other attributes of those nodes remain the same.

Querying the Knowledge Graph: The knowledge graph may be queried in many ways. The graph may be queried to provide a subset of nodes and/or a subset of edges, according to any attribute or combination of attributes of nodes and/or edges. In examples, the knowledge graph may be queried to obtain all nodes that have a Category of ALLERGY and/or all edges attached to these nodes. The knowledge graph may be queried to obtain all nodes and/or edges that are connected to any node with a Category of ALLERGY including nodes that have other Categories. The knowledge graph may be queried to obtain all nodes and/or edges that were created by a particular user.

Dropdown Menus: Within the topic-specific interfaces (e.g. Medical History, Medications, Family History, or Surgical History) there may be dropdown menus (for example implemented as "Multiple Selection" and/or "Search Selection" and/or "Multiple Search Selection" dropdown menus as defined in React or Semantic UI) for various fields, to enable collection of structured data and to accelerate the process of entering information into the system. The following fields may come with predefined lists of terms accessible through a dropdown interface: diagnoses, procedures, medications, side effects, family members, and symptoms. Diagnosis and procedure terms may be associated with, copied from, or derived from SNOMED Clinical Terms (SNOMED-CT), International Statistical Classification of Diseases and Related Health Problems (ICD), Clinical Classifications Software (CCS), and/or Current Procedural Terminology (CPT) codes.

Topic-Specific Section Loading: It is also desirable to reduce repetitive information entry across different visits. Specifically, the product should not require a user to fill out information in the relatively static topic-specific sections in every visit from scratch. The topic-specific sections are described as "relatively static" because they are unlikely to change substantially from one interview to the next—for example, topic-specific sections may include:

Medications (e.g., if the patient is taking metformin now, they will likely be taking it later);

Past Medical History (e.g., if the patient has been diagnosed with a heart attack, this will remain part of their medical history for all future visits);

Past Surgical History (e.g., if a patient has had their appendix removed, then appendectomy will remain part of their surgical history for all future visits);

Allergies (e.g., if the patient is allergic to penicillin, this will remain listed in their allergies section for all future visits);

In accordance with embodiments, the topic-specific section information may be automatically loaded into the current note interface from the patient's most recent past note and/or from a database that stores the patient's most recent topic-specific section information. Automatically loading the topic-specific sections may increase the speed at which the user can correctly fill in all of the elements of the note interface. The interface may allow the user to edit the information or to "confirm" the information, for example by clicking a button. The database may store the date when the information was last confirmed, as well as which user confirmed it.

Generating a Note or Narrative: In accordance with embodiments, systems and methods disclosed herein can transform questionnaire results into a medical note or narrative based on a knowledge graph structure and artificial intelligence. Systems disclosed herein can transform question-response pairs obtained through the knowledge graph structure into complete, grammatical sentences to produce a coherent medical note. Further, systems disclosed herein can use a rule-based system for the initial sentence generation. The rule-based system may rely on specification of particular question types (e.g. YES-NO, CLICK-BOXES, SHORT-TEXT, NUMBER, TIME, etc.), and specification of a template sentence for each question. The sentences can be formed into paragraphs using the information stored in the knowledge graph structure. For example, the sentences can be concatenated, one after the other, based on the node order defined in the knowledge graph structure and/or the connectivity of nodes in the knowledge graph structure, to produce an overall narrative. As previously described, the node order may be defined using an attribute of nodes or using one or more attributes of edges.

Examples of initial text generation through a rule-based system:

| Question Type | Question Text | Template Sentence(s) for Completion | User Input of Patient's Response | Generated Sentence |
|---|---|---|---|---|
| YES-NO | Do you have a headache? | Yes: The patient reports a headache. No: The patient does not have a headache. | Yes | The patient reports a headache. |
| YES-NO | Do you have a headache? | Yes: The patient reports a headache. No: The patient does not have a headache. | No | The patient does not have a headache. |
| CLICK-BOXES | How would you describe the chest pain? burning, crushing, sharp, dull | The patient's chest pain is | burning, crushing | The patient's chest pain is burning and crushing. |
| TIME | How long ago did the shortness of breath start? | The shortness of breath started ago. | 9 days | The shortness of breath started 9 days ago. |
| SHORT-TEXT | Please describe the previous incident where you lost consciousness. | In the previous incident where the patient lost consciousness, | I got up quickly from the dinner table and then fainted onto my couch | In the previous incident where the patient lost consciousness, I got up quickly from the dinner table and then fainted onto my couch. |
| BODY-LOCATION | Where is the pain located? | The pain is located in the patient's | right arm | The pain is located in the patient's right arm. |

Family History (e.g., if the patient's grandfather died of cancer, this will remain part of the family history for all future visits);

Social History (e.g., if the patient has ever smoked tobacco, this will remain part of their social history for all future visits)

Template Sentences: One or more nodes within the knowledge graph may be associated with a template sentence, which may be used in the note generation process. The table below provides additional examples of template sentences for different Question Types and Question Text, along with User Input of the Patient's Response and the resulting Generated Sentence. The Generated Sentence becomes part of the narrative that is produced. The Generated Sentence is produced by combining the template sentence with the User Input of Patient's Response. For YES-NO questions, the patient's "Yes" or "No" answer determines which of 2 template sentences will be selected to produce the final sentence. For all other question types shown here, the patient's answer is inserted into the template sentence to produce the final Generated Sentence. For CLICK-BOXES questions, both the options that the patient did select (ANSWER) as well as the options the patient did not select (NOTANSWER) may be used in creating the final Generated Sentence. For CLICK-BOXES, LIST-TEXT, or other question types that produce lists of items, commas and the word "and" or the word "or" may be used to join together multiple options.

Additional examples of sentence generation through a rule-based system, with many examples of Template Sentence(s) for Completion:

| Question Type | Question Text | Template Sentence(s) for Completion | User Input of Patient's Response | Generated Sentence |
|---|---|---|---|---|
| BODY LOCATION | Where do you feel the muscle cramps? | The patient feels muscle cramps in the ANSWER. | right calf and right foot | The patient feels muscle cramps in the right calf and right foot. |
| BODY LOCATION | Where do you feel the tingling? | The patient feels tingling in the ANSWER. | left hand | The patient feels tingling in the left hand. |
| CLICK-BOXES | Which of the following symptoms do you experience with allergies? runny nose, congestion, watery eyes, red eyes, sneezing, cough, fatigue | The patient experiences ANSWER when they have allergies. The patient denies NOTANSWER. | runny nose, congestion, watery eyes | The patient experiences runny nose, congestion, and watery eyes when they have allergies. The patient denies red eyes, sneezing, cough, or fatigue. |
| CLICK-BOXES | Which of the following do you experience along with anxiety? feeling restless, fatigue, difficulty concentrating, irritability, tense muscles, problems falling asleep | The patient experiences ANSWER with anxiety. The patient denies NOTANSWER. | fatigue, problems falling asleep | The patient experiences fatigue and problems falling asleep with anxiety. The patient denies feeling restless, difficulty concentrating, irritability, or tense muscles. |
| CLICK-BOXES | When are your joints the most painful? in the morning, in the afternoon, at night | The patient's joints are the most painful ANSWER. | in the morning | The patient's joints are most painful in the morning. |
| CLICK-BOXES | Which of the following symptoms do you experience during the day (if none, leave blank)? shortness of breath, chest tightness, cough, wheezing | The patient experiences the following symptoms during the day: ANSWER. The patient denies NOTANSWER. | [blank-no options were selected] | The patient denies shortness of breath, chest tightness, cough, or wheezing. |
| CLICK-BOXES | Do you use insulin from: a pen, a bottle and syringe | The patient uses insulin from ANSWER. | a pen | The patient uses insulin from a pen. |
| CLICK-BOXES | Which eye(s) are affected? left eye, right eye, both eyes | The following eyes are affected: ANSWER. | left eye | The following eyes are affected: left eye. |
| CLICK-BOXES | Have you had exposure to any of the following? radiation, infrared radiation, lightning strike, excessive sunlight, high-voltage current | The patient reports exposure to ANSWER. | excessive sunlight | The patient reports exposure to excessive sunlight. |
| FH-BLANK | Please list the members of your family with psychiatric conditions, their diagnoses, and date when they were diagnosed, if applicable. | The following members of the patient's family have a psychiatric diagnosis: ANSWER | mother with schizophrenia (January 2017), brother with anxiety (April 2005) | The following members of the patient's family have a psychiatric diagnosis: mother with schizophrenia (January 2017), brother with anxiety (April 2005). |
| FH-POP | Do you have a family history of: allergies, asthma, ezcema, hay fever | The patient has a family history of ANSWER. The patient denies a family history of NOTANSWER | allergies, eczema | The patient has a family history of allergies and eczema. The patient denies a family history of asthma or hay fever. |

Additional examples of sentence generation through a rule-based system, with many examples of Template Sentence(s) for Completion:

| Question Type | Question Text | Template Sentence(s) for Completion | User Input of Patient's Response | Generated Sentence |
|---|---|---|---|---|
| FH-POP | Does anyone in your family have a history of aortic dissection, blood vessel problems? | The patient reports a family history of ANSWER. The patient reports no family history of NOTANSWER. | Aortic dissection in mother | The patient reports a family history of aortic dissection in mother. The patient reports no family history of blood vessel problems. |
| FH-POP | Do you have a family history of any of the following? (if none, leave blank) rheumatoid arthritis, osteoarthritis | The patient has a family history of ANSWER. | rheumatoid arthritis | The patient has a family history of rheumatoid arthritis. |
| LIST-TEXT | Please list any other allergens that trigger your allergies, which you have not already listed. | ANSWER also trigger the patient's allergies. | peanuts, walnuts | Peanuts and walnuts also trigger the patient's allergies. |
| LIST-TEXT | What do you do to try to reduce your blood pressure? | To reduce their blood pressure, the patient tries ANSWER. | exercising, eating less salt | To reduce their blood pressure, the patient tries exercising and eating less salt. |
| LIST-TEXT | What foods and drinks do you normally have for breakfast? | The patient normally eats ANSWER for breakfast. | cereal, milk, eggs | The patient normally eats cereal, milk, and eggs for breakfast. |
| MEDS-BLANK | Please list the medications you are currently taking for your allergies in the table below, including any side effects. | The patient is currently taking ANSWER for their allergies. | Zyrtec with no side effects | The patient is currently taking Zyrtec with no side effects for their allergies. |
| MEDS-BLANK | Please list which medications you have tried for your symptoms. | The patient has tried ANSWER to relieve their symptoms. | Advil | The patient has tried Advil to relieve their symptoms. |
| MEDS-BLANK | Please list which medications you have tried for your heartburn. | The patient has tried ANSWER to relieve their heartburn. | Pepcid | The patient has tried Pepcid to relieve their heartburn. |
| MEDS-BLANK | Please list which medication(s) you are currently taking for hyperlipidemia. | The patient is taking the following medications for hyperlipidemia: ANSWER. | atorvastatin, colestipol | The patient is taking the following medications for hyperlipidemia: atorvastatin and colestipol. |
| MEDS-POP | Are you currently taking any of the following medications? glucocorticoids, cholinesterase inhibitors, anticholinergics, sympathomimetics, amphetamines, cocaine | The patient is currently taking ANSWER. | glucocorticoids | The patient is currently taking glucocorticoids. |
| NUMBER | How many drinks of wine do you have in a 24-hour period? | The patient has ANSWER drinks of wine in a 24-hour period | 2 | The patient has 2 drinks of wine in a 24-hour period. |
| NUMBER | How many episodes of wheezing have you had in the last 12 months? | The patient has had ANSWER episodes of wheezing in the last 12 months. | 20 | The patient has had 20 episodes of wheezing in the last 12 months. |
| PMH-BLANK | What was your child hospitalized for? | The patient was previously hospitalized for ANSWER. | pneumonia | The patient was previously hospitalized for pneumonia. |
| PMH-BLANK | Please fill out the pregnancy complications in the table below. | The patient suffered pregnancy complications: ANSWER. | pre-eclampsia, gestational diabetes | The patient suffered pregnancy complications: pre-eclampsia and gestational diabetes. |
| PMH-POP | Do you have any of the following conditions? asthma, eczema, hay fever | The patient has the following atopic conditions: ANSWER. The patient does not have the following | [blank-no options were selected] | The patient does not have the following atopic conditions: asthma, eczema, hay fever. |

Additional examples of sentence generation through a rule-based system, with many examples of Template Sentence(s) for Completion:

| Question Type | Question Text | Template Sentence(s) for Completion | User Input of Patient's Response | Generated Sentence |
|---|---|---|---|---|
| PMH-POP | Do you have a history of: aortic aneurysm, Marfan syndrome, Ehlers-Danlos syndrome, connective tissue disorder, high blood pressure, atherosclerosis, smoking | atopic conditions: NOTANSWER The patient has a history of ANSWER. The patient has no history of NOTANSWER. | Marfan syndrome | The patient has a history of Marfan syndrome. The patient has no history of Ehlers-Danlos syndrome, connective tissue disorder, high blood pressure, atherosclerosis, or smoking. |
| PMH-POP | Do you have a history of any of the following? recent infection, recent diagnosis of cancer, IV drug use, osteoporosis | The patient has a history of ANSWER. The patient denies a history of NOTANSWER. | recent infection, osteoporosis | The patient has a history of recent infection and osteoporosis. The patient denies a history of recent diagnosis of cancer or IV drug use. |
| PMH-POP | Have you had any of the following in the past? pulmonary embolism, deep vein thrombosis | The patient has a history of ANSWER. | deep vein thrombosis | The patient has a history of deep vein thrombosis. |
| PSH-BLANK | Please list the operations you have had on your heart or arteries in the table below. | The patient has had recent operations on their heart or arteries: ANSWER. | CABG | The patient has had recent operations on their heart or arteries: CABG. |
| PSH-POP | Have you had any of the following surgeries? open heart surgery, stent placement, cardiac bypass surgery | The patient has had the following surgeries: ANSWER. | stent placement | The patient has had the following surgeries: stent placement. |
| SCALE1TO10 | How would you rate your stress level on a scale of 1 (no stress) to 10 (highest stress)? | The patient reports a stress level of ANSWER out of 10. | 7 | The patient reports a stress level of 7 out of 10. |
| SCALE1TO10 | On a scale of 1 (poor) to 10 (excellent), how well do you think you are controlling your blood sugar? | The patient believes that they are controlling their blood glucose levels at a ANSWER out of 10, where 1 is poor and 10 is excellent. | 4 | The patient believes that they are controlling their blood glucose levels at a 4 out of 10, where 1 is poor and 10 is excellent. |
| SCALE1TO10 | On a scale of 1 (least fit) to 10 (most fit), how would you rate your personal fitness? | The patient rates their personal fitness as ANSWER out of 10, where 10 is "most fit." | 9 | The patient rates their personal fitness as 9 out of 10, where 10 is "most fit." |
| SHORT-TEXT | When were you hospitalized for an asthma attack? | The patient was hospitalized for an asthma attack in ANSWER. | July 2009 | The patient was hospitalized for an asthma attack in July 2009. |
| SHORT-TEXT | Please describe what caused your back injury. | The patient describes their back injury as follows: | I was lifting a heavy box and felt a sudden pain in my lower back. | The patient describes their back injury as follows: I was lifting a heavy box and felt a sudden pain in my lower back. |
| SHORT-TEXT | What did you do yesterday? | The patient states that yesterday, they ANSWER. | went grocery shopping and walked the dog | The patient states that yesterday, they went grocery shopping and walked the dog. |
| SHORT-TEXT | What company, organization, or institution do you work for? | The patient works at ANSWER. | Costco | The patient works at Costco. |
| SHORT-TEXT | What questions or concerns do you have? | The patient reports the following questions and | How do I lower my blood sugar? | The patient reports the following questions and |

Additional examples of sentence generation through a rule-based system, with many examples of Template Sentence(s) for Completion:

| Question Type | Question Text | Template Sentence(s) for Completion | User Input of Patient's Response | Generated Sentence |
|---|---|---|---|---|
| | | concerns: ANSWER | | concerns: How do I lower my blood sugar? |
| SHORT-TEXT | What are your exercise goals? | The patient has the following exercise goals: ANSWER. | to run a mile in 8 minutes | The patient has the following exercise goals: to run a mile in 8 minutes. |
| TIME | How long ago was your last menstrual period? | The patient's last menstrual period was ANSWER ago. | 3 weeks | The patient's last menstrual period was 3 weeks ago. |
| TIME | How long ago were you diagnosed with asthma? | The patient was diagnosed with asthma ANSWER ago | 5 years | The patient was diagnosed with asthma 5 years ago. |
| TIME | How often do you use your inhaler? Every: | The patient uses their inhaler every ANSWER. | 2 hours | . . . The patient uses their inhaler every 2 hours. |
| TIME | When were you diagnosed with COPD? | The patient was diagnosed with COPD ANSWER ago. | 10 years | The patient was diagnosed with COPD 10 years ago. |
| YES-NO | Are you currently eating a low-fiber diet? | Yes: The patient is currently eating a low-fiber diet. No: The patient does not eat a low-fiber diet. | Yes | The patient is currently eating a low-fiber diet. |
| YES-NO | Did the pain come on suddenly? | Yes: The patient's pain came on suddenly. No: The patient's pain did not start suddenly. | No | The patient's pain did not start suddenly. |
| YES-NO | Did the chest pain come on suddenly? | Yes: The chest pain came on suddenly. No: The chest pain did not come on suddenly. | Yes | The chest pain came on suddenly. |

Refining a Note or Narrative: Once the initial note is generated using the rule-based method just described, the text may be altered, updated, edited, rephrased, rearranged, improved, and/or highlighted using machine learning, rules, and other artificial intelligence techniques. The following are some examples of how sentences can be altered, updated, or improved:

- Machine learning can be used to change verb tense from first person or second person to third person: "In the previous incident where the patient lost consciousness, I got up quickly from the dinner table and then fainted onto my couch"→"In the previous incident where the patient lost consciousness, they got up quickly from the dinner table and then fainted onto their couch"
- Rules can be used to create gender-specific language: with target pronouns "female"→"In the previous incident where the patient lost consciousness, she got up quickly from the dinner table and then fainted onto her couch."
- Rules can be used to replace "the patient" alternately with "he/she" or the patient's name: with target gender "female" and name "ANGELA SMITH"→"In the previous incident where Ms. Smith lost consciousness, she got up quickly from the dinner table and then fainted onto her couch."
- Rules can be used to perform a "translation" between colloquial terms and medical terms. For example, "shortness of breath"="dyspnea", "heart attack"="myocardial infarction", "fast breathing"="tachypnea" and so on. This "translation" may also be used in data analysis, databases, or other parts of the product.

Create Custom Knowledge Graphs: In accordance with other embodiments, systems and methods disclosed herein can allow users to create custom knowledge graphs. Allowing users to create custom knowledge graphs enables inclusion of an unlimited number of diseases and conditions and symptoms, as users can define a knowledge graph for anything. Furthermore, custom knowledge graphs make the product accessible for any medical specialty, including medical subspecialties that may focus on rare conditions, because users can define custom knowledge graphs for even rare conditions. User knowledge graphs may be aggregated into the system's main knowledge graph. Incorporation of user knowledge graphs into the system's main knowledge graph may lead to improved quality of the system's main knowledge graph because some users of the product may be experts on particular conditions and can thus create the best knowledge graphs possible for those conditions.

The custom knowledge graphs may include custom questions. Each custom question may be paired with a custom template sentence. Example pairs follow:

YES-NO question example: "Do you have chest pain?" is paired with the template sentences of "The patient reports chest pain" (for a yes response) and "The patient reports no chest pain" (for a no response.)

LIST-TEXT question example: "Please list the foods you ate while traveling" is paired with the template sentence, "The patient ate RESPONSE while traveling." (Thus if the patient listed "meat, cheese, and pears" the produced sentence would be "The patient ate meat, cheese, and pears while traveling.)

TIME question example: "How long has this headache lasted?" is paired with the template sentence, "The headache has lasted RESPONSE." (Thus, if the patient typed in "5 hours" the produced sentence would be "The headache has lasted 5 hours.")

Social Networking: In accordance with other embodiments, the system may include a social networking component in which a user can browse, save, and rate custom knowledge graphs created by other users. For example, if 500 different doctors have created different knowledge graphs for "chest pain" then other doctors can "rate" each of these knowledge graphs on a 0-5 star scale, which then enables quantitative determination of the chest pain knowledge graph with the highest average score. Doctors can also "save" knowledge graphs created by other doctors that they want to use in the future. The highest-rated knowledge graphs (closest to 5/5 stars) for "chest pain" may appear at the top of search results for "chest pain." Thus, the product may have a social component.

Account Types: In accordance with embodiments different account types may be generated. Examples follow:

| User Profiles/Account Types: | |
|---|---|
| Account Type | Features |
| Patient Account | A patient account may be generated. A patient account may enable a patient: To enter demographic information and personal information such as first name, last name, phone number, address, email address, preferred pronouns, and location To fill out questionnaires To match themselves with doctors or clinics. |
| Doctor Account | A doctor account may be generated. A doctor account may be intended for a doctor, researcher, physician assistant, nurse, medical student, or other clinician. A doctor account may enable a clinician: To enter information about degrees obtained, degrees in progress, current job, and current institution. To send a patient a questionnaire for the patient to fill out To receive a filled-out questionnaire from a patient To fill out a questionnaire during or after interviewing a patient in order to generate a note quickly To save their most commonly used note questionnaires To match themselves with patients or clinics. To pay for continued access to the product, for example via a monthly subscription fee. |
| Clinic Account | A clinic account may be generated. A clinic account may be intended for a clinic, hospital, research group running a clinical trial, or other medical organization. A clinic account may be associated with doctors, researchers, and clinicians. A clinic account can match itself with patients and doctors, and can match patients with doctors or researchers. |
| Manager Account | A manager account may be generated. A manager account may be intended for an administrative employee of an organization. A manager account may create new doctor accounts or delete existing doctor accounts. A manager account may pay the product-related fees of associated doctor accounts. |
| Researcher Account | A researcher account may be generated. A research account may be intended for a machine learning researcher. The machine learning researcher can submit machine learning models to be trained and evaluated on the system's data. |

In accordance with embodiments, a cloud service provider such as Microsoft Azure or Amazon AWS may be used to host the website or application, store the data, and/or run the machine learning models.

In an example where protected health information is stored in a database, numerous different techniques may be incorporated to enable the system to achieve compliance with HIPAA and HITECH regulations, which specify that protected health information must be encrypted while in transfer and at rest, data must be backed up, and user actions must be logged to record who has accessed what data and when.

In another example, a note may be generated based on information that a user entered in to the product's user interface, but no data may be stored in any database, meaning that the user must save the generated note somewhere else outside of the product if they wish to access it in the future.

For data storage and data analysis, automatic or manual tagging of disease and procedure phrases with SNOMED Clinical Terms (SNOMED-CT), International Statistical Classification of Diseases and Related Health Problems (ICD), Clinical Classifications Software (CCS), and/or Current Procedural Terminology (CPT) codes may be used. Automatic tagging methods may include rule-based methods and machine-learning-based methods. Tagging phrases with codes enables better data organization. For example, such tagging can indicate how "anterior STEMI" is related to "myocardial infarction" and how "tuberculous pneumonia" is related to "tuberculosis."

Artificial Intelligence: In accordance with other embodiments, systems disclosed herein can include artificial intelligence built on data collected through the knowledge graph, data collected through the custom interfaces, and/or data available through other public or private sources. Artificial intelligence may include rule-based expert systems, regression, random forests, support vector machines, neural networks, and/or other algorithms.

Some of the artificial intelligence systems may produce results that are used in the Plan section of the note, for example to show the user possible diagnoses relevant to the differential diagnosis, and/or to show the user possible medications, procedures, services, referrals, and/or consults that may be an appropriate part of the plan for this note. For example, some of the artificial intelligence systems may produce results for the following tasks related to the Plan section:

Predict the most likely diagnoses.

Predict the medications that should be used for treatment, if any.

Predict the procedures or services that should be ordered for treatment or further diagnostic workup, if any (e.g. appendectomy for appendicitis, EKG for abnormal heart rhythm).

Predict whether the patient needs a referral or a consult, and if so, what kind of specialist they need to see.

Some of the artificial intelligence systems may produce results that are used to display predictions about the patient, for example results for the following tasks:

Predict how sick the patient is on a scale of 1 to 10 where 1=healthy and 10=critically ill/ICU-level illness. This could be helpful in emergency room triage. For example, if a patient is critically ill but was somehow "missed" by the person coordinating triage, the software could identify them as being high risk so they could be seen by a doctor sooner.

Predict whether the patient needs to be admitted to the hospital.

Some of the artificial intelligence systems may produce results that are related to the History of Present Illness section and the underlying knowledge graphs, for example results for the following tasks:

Predict what other questions to ask the patient. For example, in the Discussion and Plan section of the note interface the doctor may record what other questions they asked the patient that were useful for determining the diagnosis. By combining this data with the questions that the patient was already asked, it may be possible to build a predictive model to predict which additional questions to ask the patient next in the History of Present Illness section. This is an application of artificial intelligence to grow the knowledge graph of questions.

Predict how to expand the Cydoc base knowledge graph using custom knowledge graphs defined by the users.

Medical Record Number: Each patient may be assigned a unique identifier, which is effectively a medical record number (MRN). The MRN may be assigned in such a way that from the MRN alone, a given patient is assigned to a training set (70%), validation set (15%), or test set (15%). As an example, if MRNs range from 0-100, then a new patient may be assigned the next sequentially available number between 0 and 70 with a 70% probability, the next available number between 70 and 85 with a 15% probability, or the next available number between 85 and 100 with a 15% probability. The training, validation, and test sets of patients determined in this way may be used in development or evaluation of artificial intelligence systems.

Automatic Formatting of Data: In accordance with embodiments, systems disclosed herein can include a framework to automatically format, preprocess, and/or clean data collected through the knowledge graph and custom interfaces to create tabular data structures. One motivation is to eliminate the need to perform manual data processing every time a new machine learning model must be trained. The tabular data structure (e.g. a pandas dataframe) may include one patient per row and one feature per column. Each feature may be presented in a clean state wherein all elements use the same measurement units and/or are drawn from a well-defined list of options. These tabular structures may be used to train and evaluate machine learning models. The formatting, pre-processing, and/or cleaning of the tabular structures may be determined in software in a flexible and extensible manner so that a developer can select which features to include in a model and how the features should be prepared. Feature preparation may include, for example, conversion into one-hot or multi-hot vectors for categorical variables, normalization using the training set mean and standard deviation, and so forth.

In accordance with embodiments, artificial intelligence, data mining, and medical knowledge may be used to build a diagnosis and treatment knowledge graph that interfaces with the questionnaire knowledge graph in order to make predictions about diagnoses and treatments.

Submission of Models: In accordance with embodiments, systems disclosed herein can include a user interface that allows machine learning researchers to submit machine learning models to be trained and evaluated on the system's data set. The researchers may not gain access to the data. Rather, they may follow predefined specifications about how to design their model so that it can be applied directly to system's data. The system may include a model library where machine learning researchers can donate models to solve different medical machine learning tasks. Other users (e.g. doctors and patients) can browse these models and apply them to a particular patient.

In an example, workflow for a machine learning researcher may include the following:
1) Write code for a machine learning model that accepts as input a particular kind of data described in the system's specifications.
2) Write code to calculate performance metrics based on the model's predictions.
3) Submit the machine learning model code and performance metrics code to the system.
4) Receive results from the system that report the performance metrics of the specified model on the system's data.

In an example, a workflow for doctors or patient may include the following:
1) Browse available machine learning models.
2) Click on a machine learning model to load it.
3) Submit a patient's data to the machine learning model.
4) Receive predictions from that machine learning model for that particular patient.

Transformation of Printable Questionnaires to Structured Electronic Data: In accordance with embodiments, the system may include printable questionnaires that can be automatically transformed into structured electronic data using artificial intelligence and other techniques. An example use case is to enable clinics to offer their patients paper forms in the waiting room, and then transform these paper forms into electronic data by photographing or scanning the forms. An example workflow follows:

1) A user prints off a questionnaire in a custom format. The printed off questionnaire includes a QR code that indicates which questionnaire the user is filling out (e.g. chest pain questionnaire), and which user is filling it out. Different questions are displayed according to their question type, e.g. with empty bubbles beside the associated text for CLICK-BOXES questions, and with text boxes for SHORT-TEXT questions.

2) The user fills out the questionnaire. For example, a user colors in bubbles of CLICK-BOXES questions and writes out handwritten free text for free text questions.

3) The user photographs the questionnaire and uploads it to the system. The QR code identifies the patient and which questionnaire was filled out. A machine learning system for handwriting recognition converts the free text into electronic text data. A computer vision model converts the other question types into structured data appropriate for that question type. For example, a computer vision model may convert a CLICK-BOXES question type into a table in which one column contains the response choice option and the other column includes a 1 or 0 depending on whether the bubble was filled in or not.

4) The data from the printed-off questionnaire is loaded into the system's custom user interface. A note is generated.
5) The generated note is copied into the electronic health record.
6) The original photographs are stored so that users can reference the pictures to clarify any data that appears confusing.

FIG. 3 is a diagram of an example data structure for constructing a narrative of an interaction with a subject and for presenting the narrative in accordance with embodiments of the present disclosure. FIG. 3 depicts example questions for chest pain and pain in general. Each box represents a node in the data structure. Each node includes a Node ID, which is an alphanumeric identifier that uniquely identifies the node. Each node has an associated response prompt (shown in the figure by "Question"), and an associated template sentence (shown in the figure by "TS"). The nodes can be linked in different ways; the links are represented as arrows. The linking of the nodes produces the data structure. The first chest pain question in the example is CHP0001 "Do you have chest pain?" If the response is yes, then the arrows to the child questions PAIN002, PAIN006, PEM0001, CHP0006, CHP0007, CHP0002, and other child questions may be traversed, and these child questions may be presented. These child questions may be follow-up question such as "Does the pain get better with sitting up and leaning forward?" or "On a scale of 1 to 10 how would you rate your pain?" Empty boxes with ellipses represent additional child questions not explicitly shown. The PEM questions, PEM0001, PEM0002, PEM0003, and PEM0004 represent pulmonary embolism nodes, with their question text and other content not explicitly shown. The link between the chest pain question CHP0001 and the pulmonary embolism question PEM0001 exemplifies how it is possible to connect data structures of different diseases or conditions to form a larger data structure. Note that it is possible to reach PAIN002, PAIN006 and other pain-related nodes from the PAIN001 node "Do you have any pain?" as well as the CHP0001 node "Do you have chest pain?" Thus, nodes can be linked in many different ways, and a single node may be used as part of questionnaires for many different diseases, symptoms, or conditions. The links, represented as arrows, are traversed according to the user's responses. There may be many different formats of the response prompts (shown in the figure by "Question") or template sentences (shown in the figure by "TS"). Multiple different formats for the response prompts (questions) are shown, including yes or no (CHP0001, CHP0006, PAIN001), multiple choice (CHP0007, CHP0002), numerical (PAIN006), and body location (PAIN002) each of which may have a unique way of being displayed in a corresponding user interface.

FIG. 4 is a diagram of the same example data structure shown in FIG. 3 for constructing a narrative of an interaction with a subject and for presenting the narrative in accordance with embodiments of the present disclosure, with additional information added to emphasize the narrative construction. Specifically, a field labeled "Response" and highlighted in yellow has been added to nodes, containing an example user response for the nodes. For example the user has responded YES to CHP0001, which is shown as "Response: YES." This response causes the links to the child nodes to be traversed. The part of the data structure which defines what kind of response causes a traversal to other nodes is not explicitly shown. Based on the user's responses and the template sentences a raw narrative is constructed and shown in yellow as "Raw Generated Text Excerpt." The text is an excerpt because it does not include sentences corresponding to nodes that are part of the data structure but not shown in full detail in the figure. The generated text has been created by inserting the user's response into the blank marked with "RESPONSE" in the template sentence, or by choosing the correct template sentence corresponding to a Yes or No response for a Yes or No question. For example, the sentence "The patient has chest pain" is selected based on a YES response to "Do you have chest pain?"; the user's response "chest and jaw" is inserted into "The patient has pain in their RESPONSE" to create the sentence "The patient has pain in their chest and jaw"; the user's response "pressure, constriction" is inserted into "The pain feels like RESPONSE" to create the sentence "The pain feels like pressure and constriction." For multiple-choice questions, the template sentence may also include options that the user did not select, represented as NOTRESPONSE. Thus, if the user does not select "squeezing, tightness, burning" for CHP0007, a sentence "It does not feel like squeezing, tightness, or burning" may be generated from this node in addition to other sentences. The generated text is referred to as "raw" because it has not undergone any clean-up steps based on rules, machine learning techniques, or artificial intelligence techniques.

FIG. 5 is another representation of an example data structure for constructing a narrative of an interaction with a subject and for presenting the narrative in accordance with embodiments of the present disclosure. Here, each row of the table corresponds to one node in the data structure, and each column of the table corresponds to a different attribute of that node. The node attributes (columns) include "Body System", which indicates which body system the node's question relates to. Body Systems shown include "CVRESP" as an example indicator for "cardiovascular and respiratory" and "MSK" as an example indicator for "musculoskeletal." The "Question Category" is the name of the disease, symptom, or condition that the node's question relates to, e.g. CHEST_PAIN, JOINT_PAIN, or PAIN. The "Question ID" is the alphanumeric ID that uniquely identifies the node. The "Question" is the text of the response prompt, which may be phrased as a question. The "Question Type" indicates a category for the "Question" which may determine how the response prompt is presented to the user in a user interface. For example, a CLICK-BOXES (multiple choice) question may be presented as the response prompt text e.g. "Do you have any of the following symptoms with your joint pain?" followed by individual clickable options for "rash," "redness," and "swelling." "Response to More Questions" (abbreviation for "Response Leading to More Questions") describes the nature of the user response that should trigger traversal to the child nodes. "Child Questions" is a list of the Question IDs for child nodes that should be traversed to if the user provides a response matching the description in the "Response to More Questions." "Template sentence" is a template sentence for questions that are not YES-NO questions. "YES: Template sentence" is a template sentence for a YES-NO question, and will become part of the generated note if the user inputs Yes to the corresponding question. "NO: Template sentence" is a template sentence for a YES-NO question, and will become part of the generated note if the user inputs No to the corresponding question.

Figure 6:
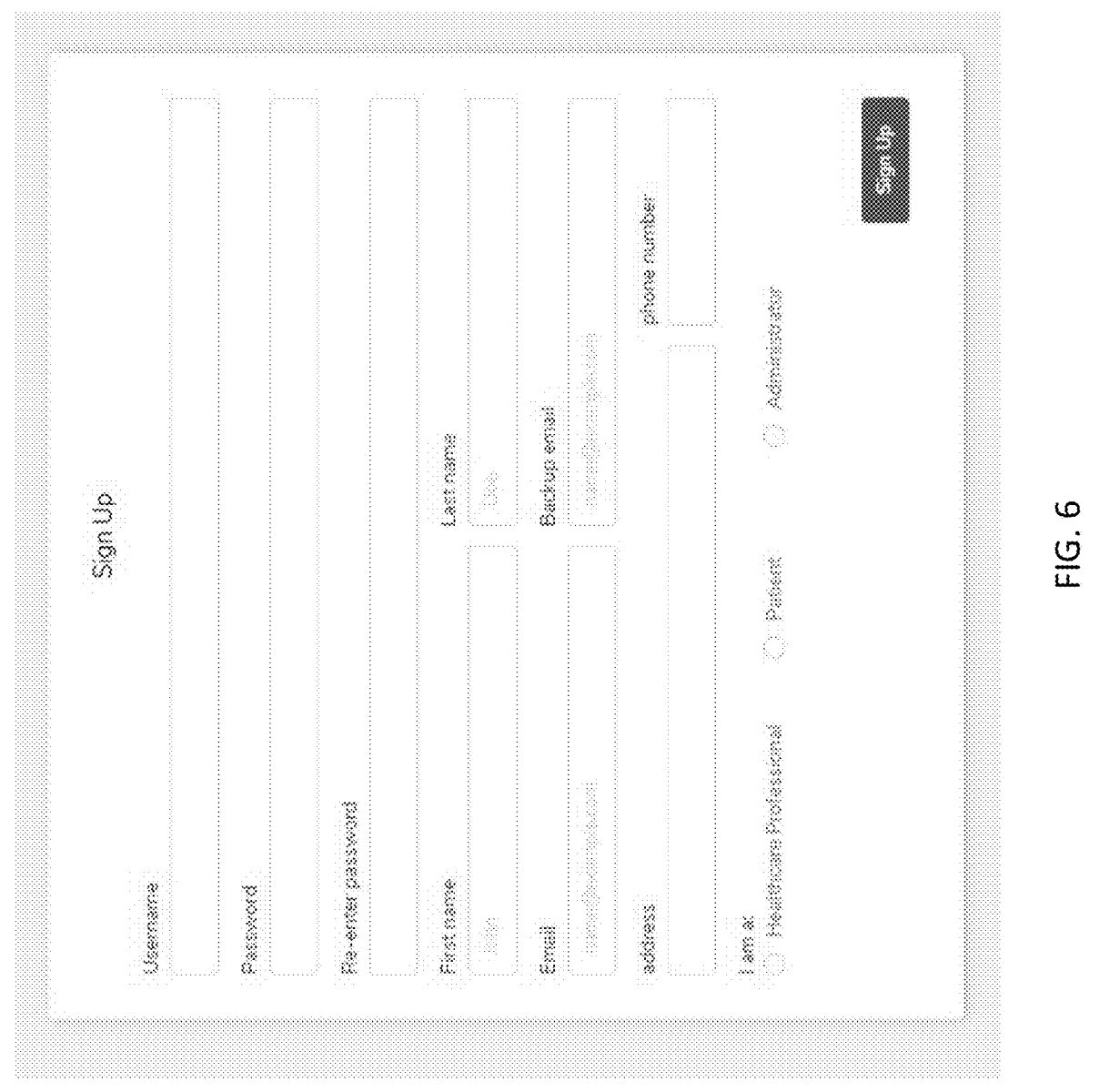

FIGS. 6-67 are various screenshots of a system in accordance with embodiments of the present disclosure.

FIG. 6 is a registration form that a user may fill out indicating personal information such as their first name, last name, email address, and whether they are a healthcare professional, patient, or administrator. The system may have a different user interface depending on whether the user is a healthcare professional, patient, or administrator.

Figure 7:
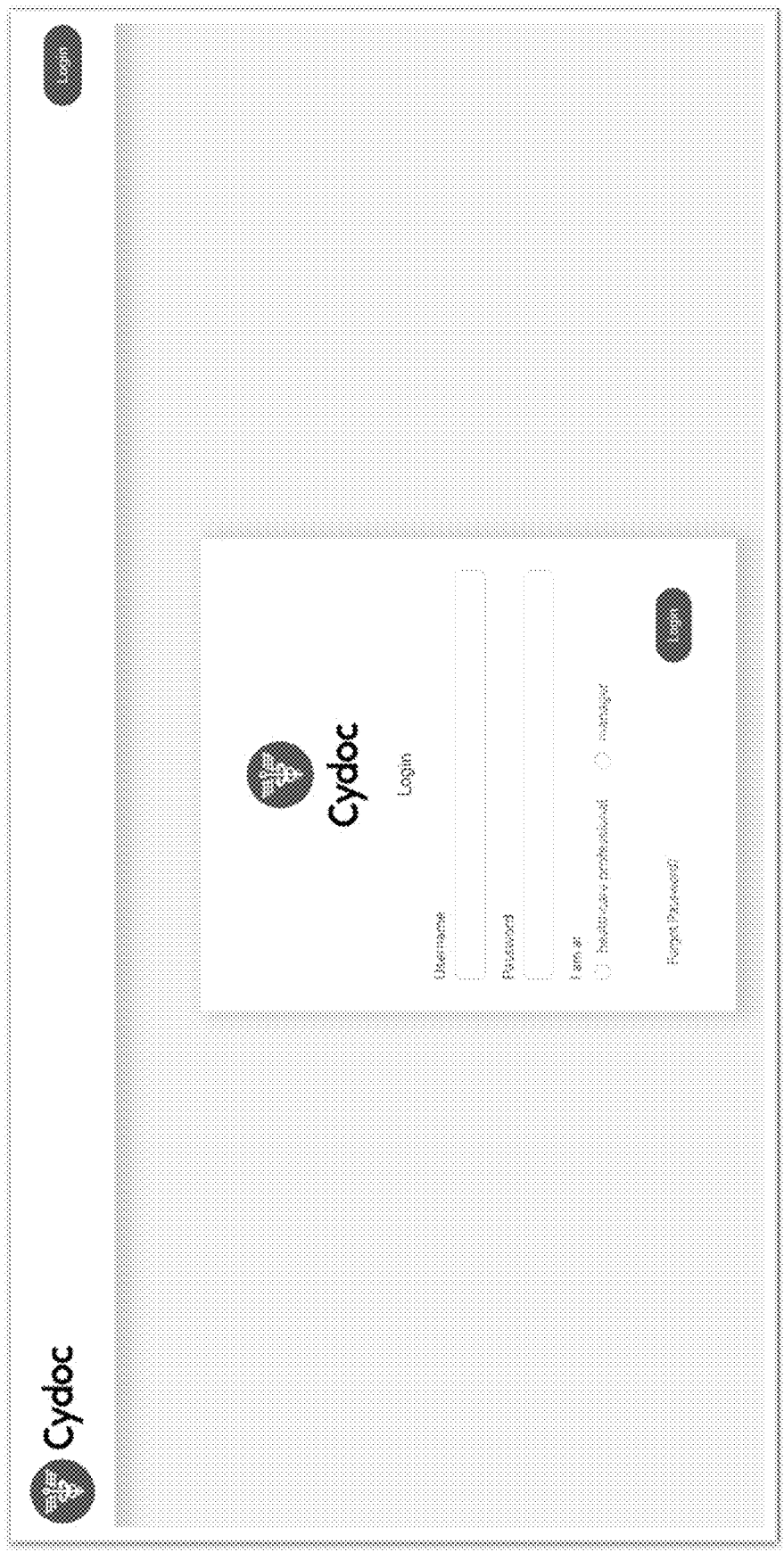

FIG. 7 is a login screen which enables the user to access the application. If any protected health data is stored, user access will comply with HIPAA and HITECH regulations including appropriate security measures, and only allowed users will be able to access protected health information. Multifactor authentication may be required—for example, after entering a username and password, a user may be required to enter a nuermic code sent to their mobile device.

Figure 8:
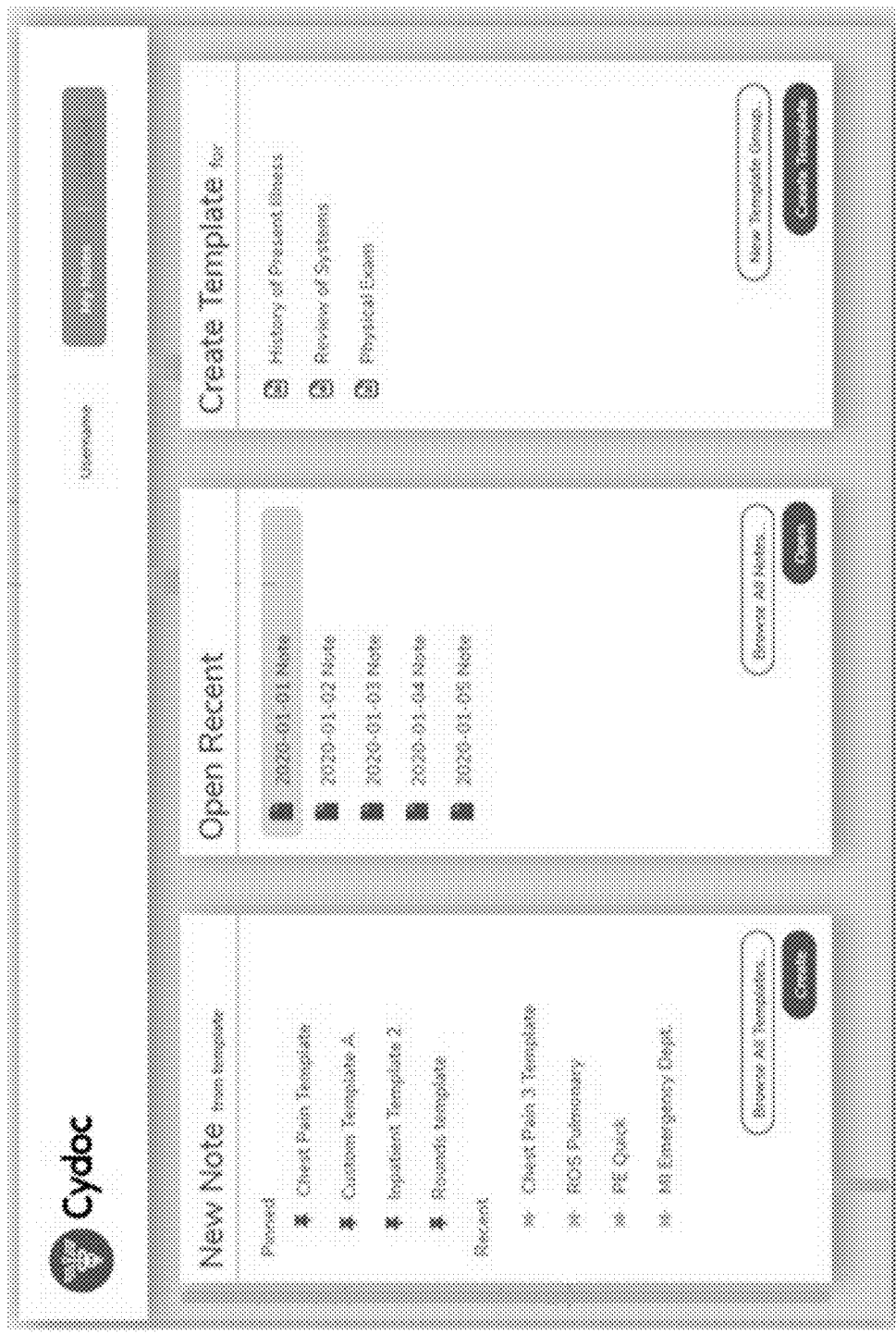

FIG. 8 is an example of a landing page that enables a user to access different functionality of the system. The "New Note" box includes pinned note questionnaires that the user has chosen to pin, as well as recently used questionnaires. The user may click on a questionnaire name to begin filling out a note based on that questionnaire. The user may also browse through all questionnaires on a separate page, if they wish to select a questionnaire that is not shown on the landing page. "Open Recent" enables a user to open a recent note that they were working on. The names of recent notes are shown. If the user clicks on the name of a recent note, that note will be loaded in to the note user interface so that the user may continue working on it. "Create Template" enables a user to create a template or questionnaire for a note section, or create a template group. Different note sections can have custom templates, including the History of Present Illness, Review of Systems, and Physical Exam. A template group indicates a grouping of a History of Present Illness, Review of Systems, and/or Physical Exam template under a single name. The user can click on the elements of the Create Template box to be taken to an interface for creating a custom template.

Figure 9:
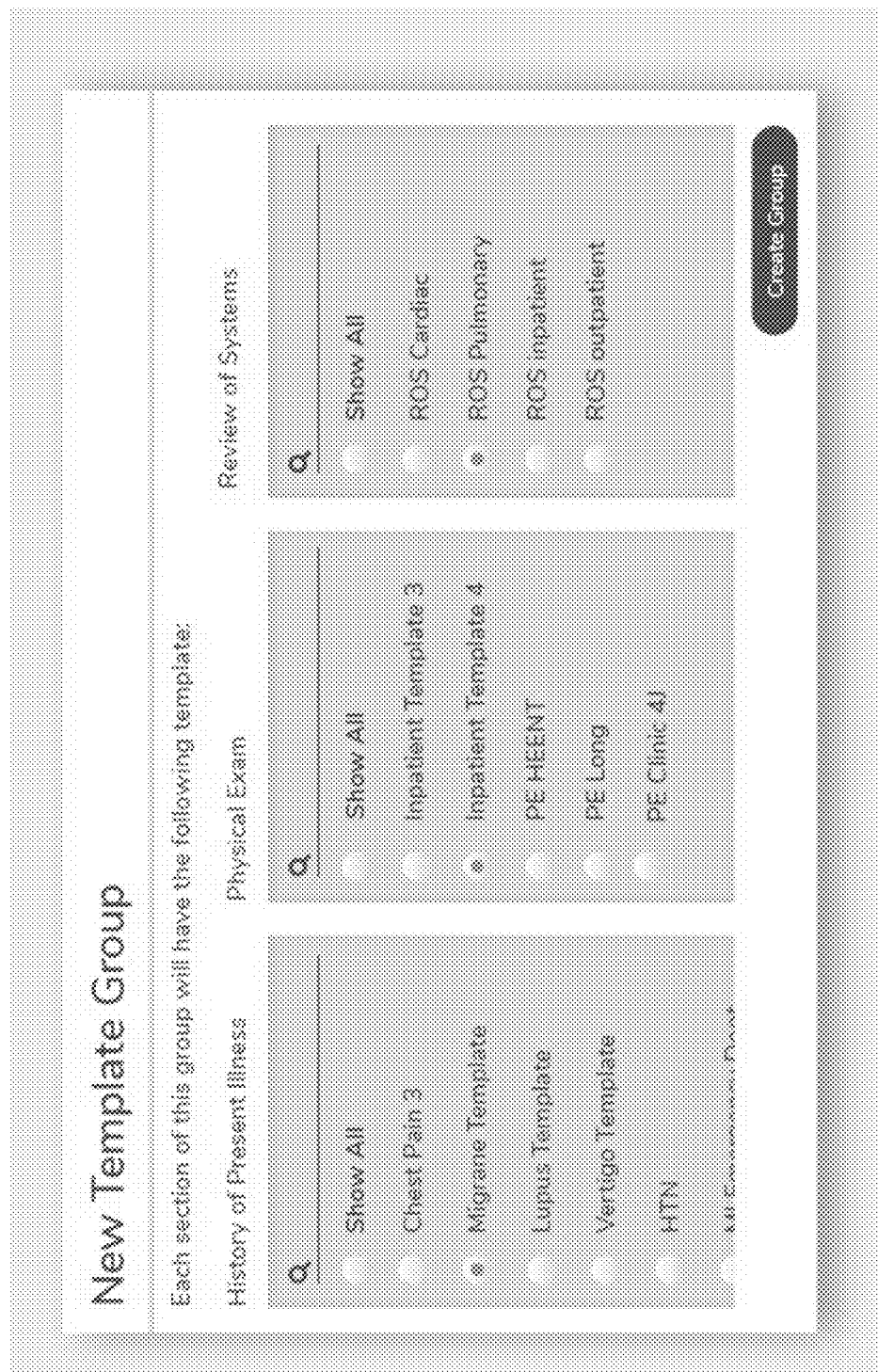

FIG. 9 is an example of creating a template group. The user can select one History of Present Illness template, one Physical Exam template, and one Review of Systems template which will be saved together under a group name. Note that there is a template option "Show all"; if "Show all" is selected then in the note user interface the user will be presented will all of the different specific options for that template. Thus, a user could for example pick "Chest Pain 3" for the History of Present Illness, "Inpatient Template 3" for the Physical Exam, and "Show All" for Review of Systems, in which case the template group would enable creation of a note interface based on "Chest Pain 3" and "Impatient Template 3"; when the user reached the Review of Systems section they would be presented with the different Review of Systems options to select from.

Figure 10:
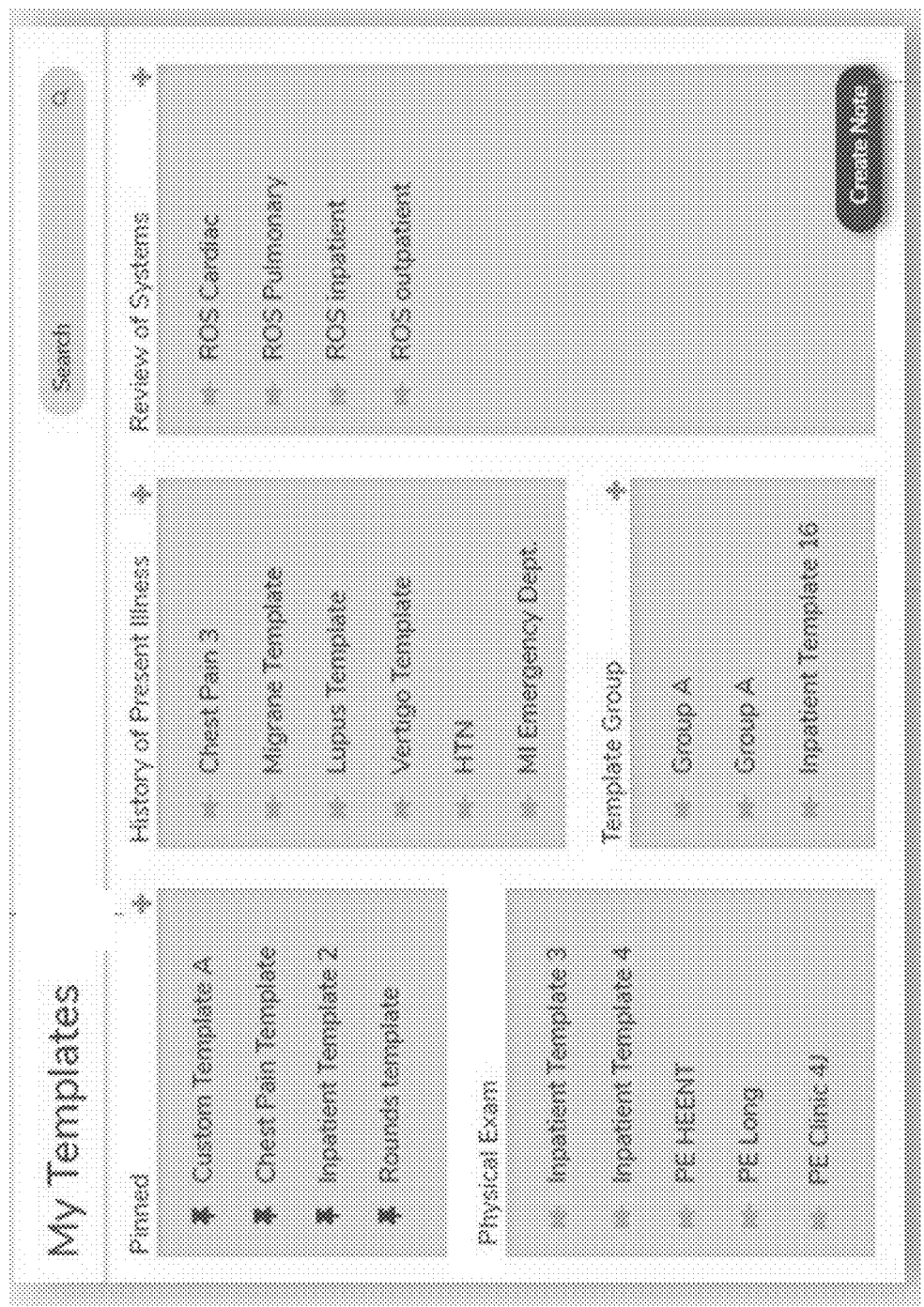

FIG. 10 is an example of a view the user may see if they choose to browse all of their existing templates. Templates are organized according to note section. There is also a box for template groups. The user can pin or unpin templates. The user can use the Search functionality to search for a template using key words and/or the template name.

Figure 11:
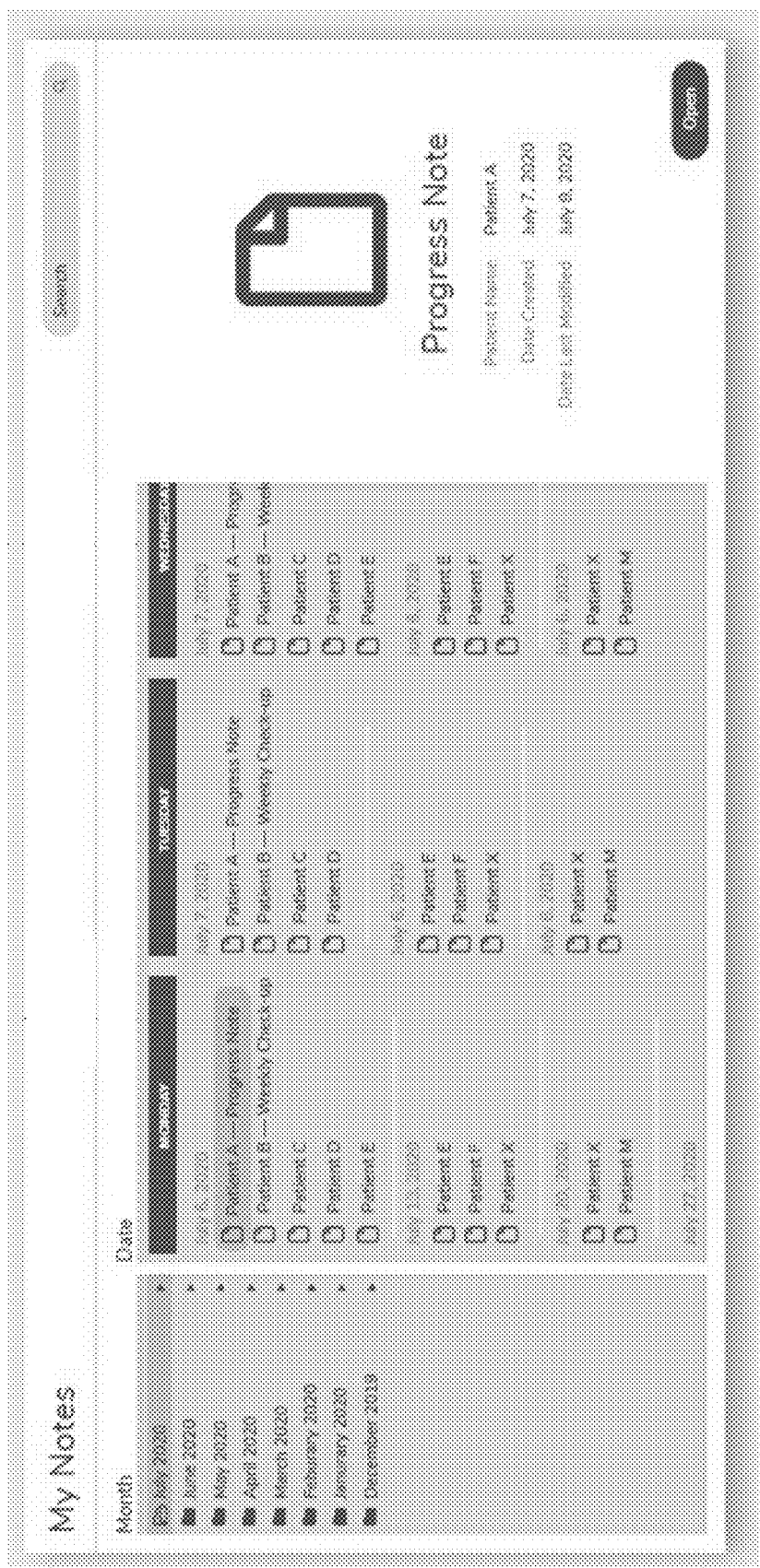

FIG. 11 is an example of a view the user may see if they choose to browse all of their existing notes. On the left, the different months are shown, organized from most recent month to least recent month. If the user selects a month, such as "July 2020" shown in the figure, then a calendar-like organized pop out will display, showing the days of that month. Each day of the month includes a list of patient names and corresponding note names. The user can select a particular note (indicated by a patient name and note name) and load that note into the interface. On the right a preview of note information is shown. This may additionally include an excerpt from the generated note.

Figure 12:

FIG. 12 is an example of the first part of a History of Present Illness section in which the user selects diseases, symptoms, or conditions that are relevant for the visit. The diseases, symptoms, or conditions may be organized by body system as shown in this figure. In this figure, the user has selected Chest Pain, Diabetes, and Joint Pain, which has caused these buttons to display in a different color and also to appear at the top of the page.

Figure 13:
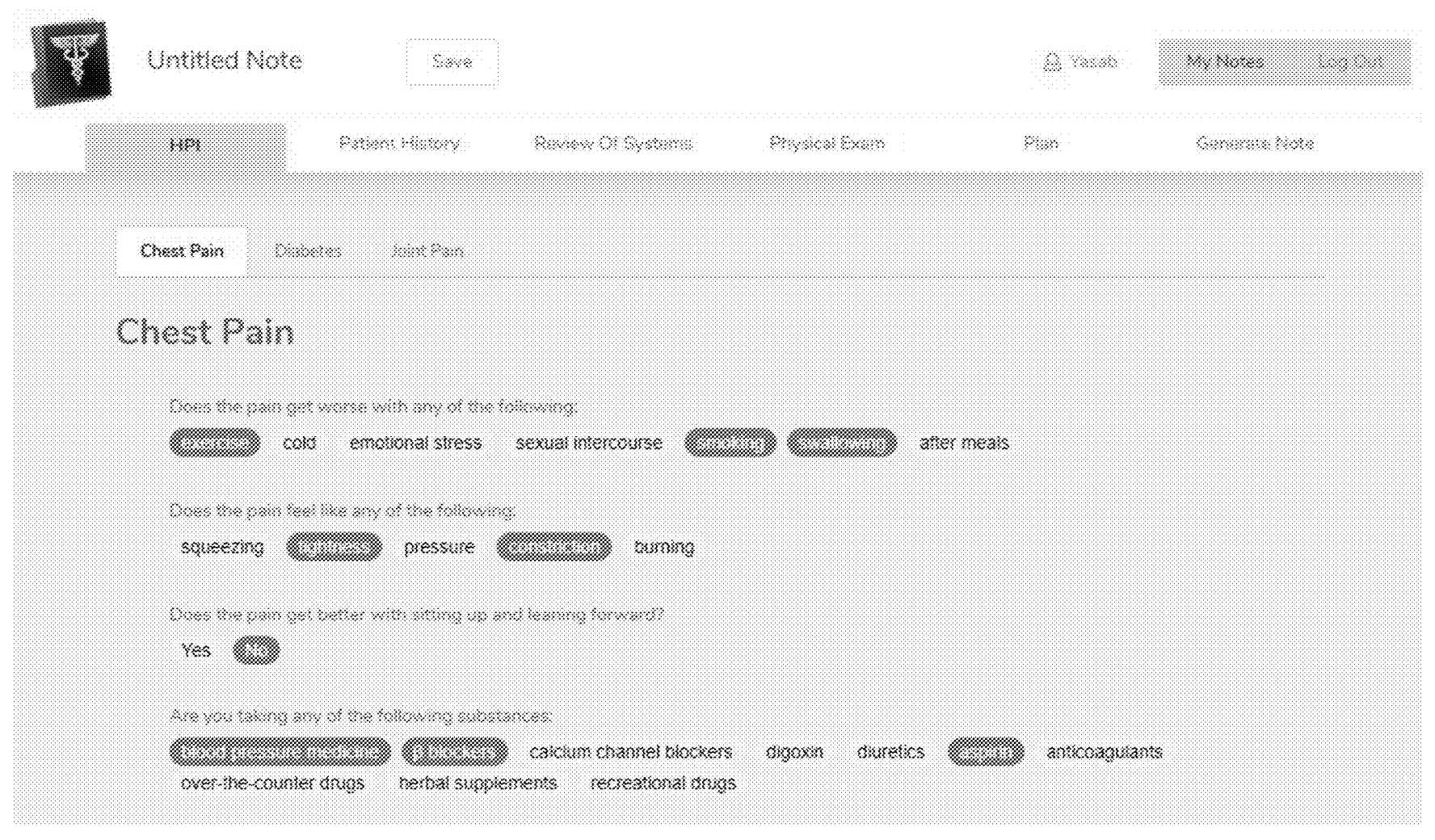

FIG. 13 is an example of the first part of a History of Present Illness questionnaire for Chest Pain. This questionnaire is produced in the user interface based on the data structure of nodes connected by links. The first two questions shown are examples of multiple-choice questions. The third question is an example of a yes or no question. Notice also that at the top there are tabs for Chest Pain, Diabetes, and Joint Pain—one tab for each of the conditions that the user selected in the first part of the History of Present Illness. These can be thought of as the Chief Complaints.

Figure 14:
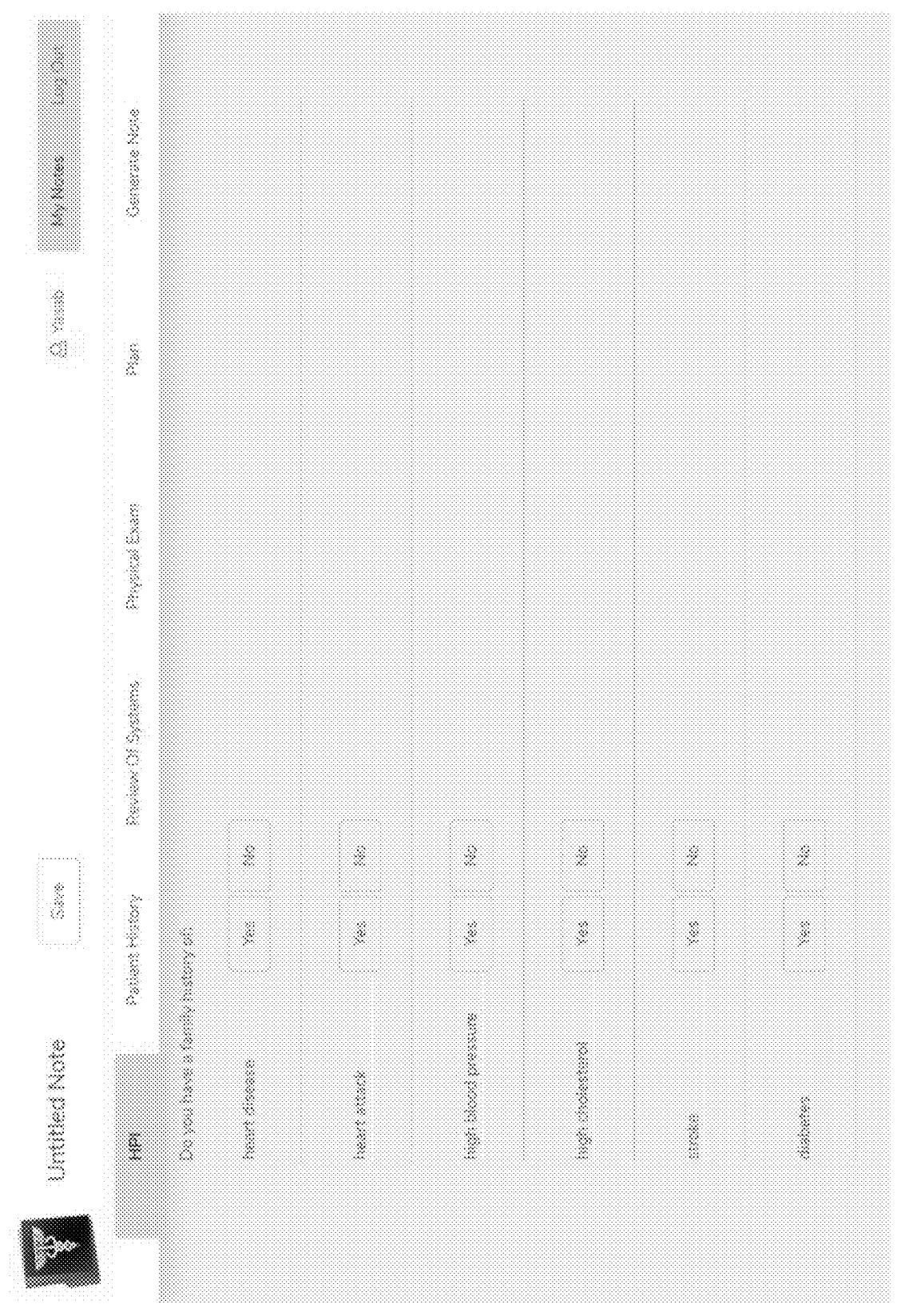

FIG. 14 is an example of an FH-POP question, or family history prepopulated question, which the user has not answered yet. When a node in the data structure is an FH-POP node, the user interface for that node is related to the user interface for the family history section, to facilitate sharing of the state and synchronization of information between the History of Present Illness family history information and the Family History section. When the user has not answered the family history question yet, as shown in this figure, only the names of the conditions are displayed along with a Yes or No option.

Figure 15:
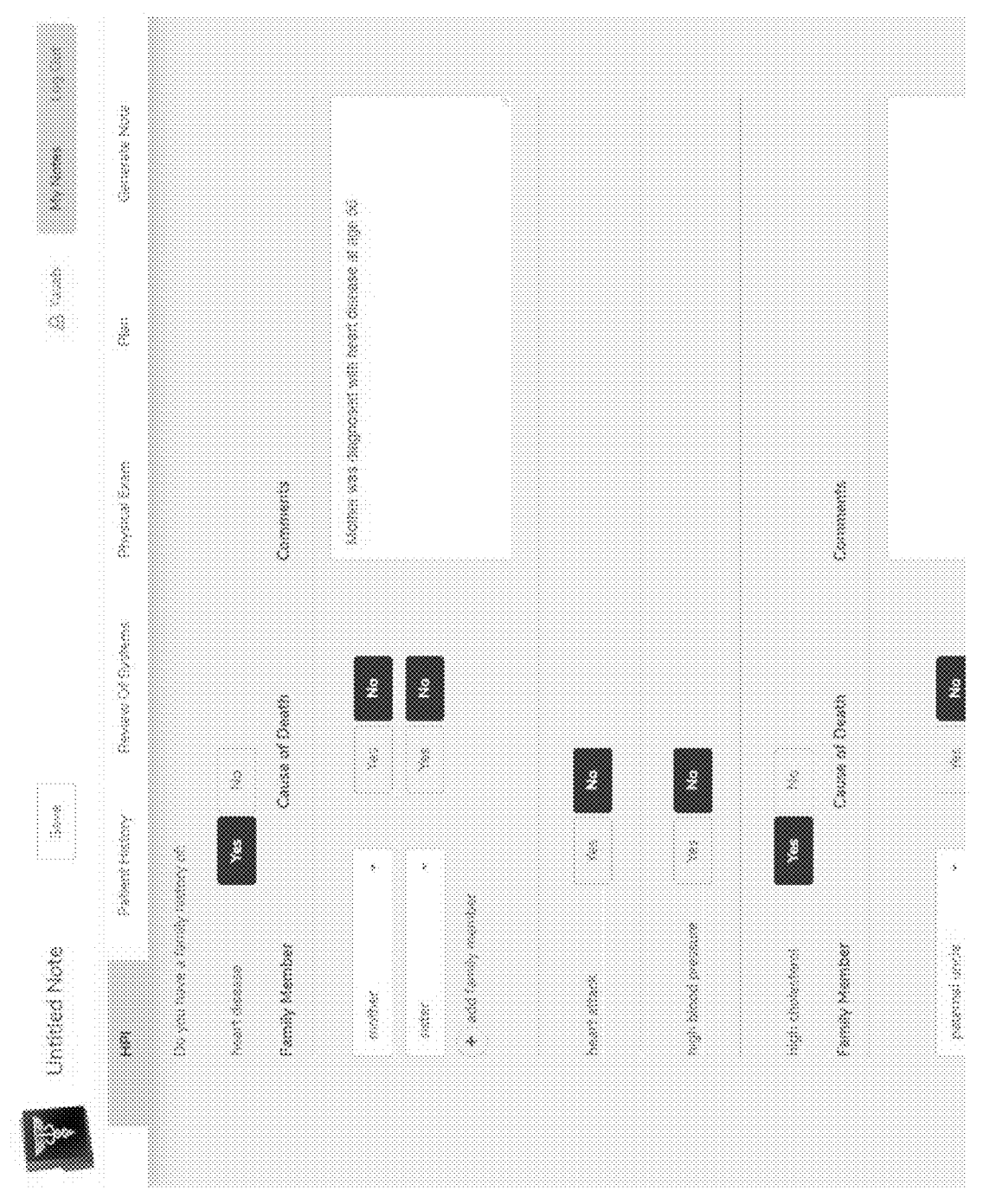

FIG. 15 is an example of the same FH-POP question shown in FIG. 14, except this time the user has filled in some responses. When the user selects Yes for a condition, as shown for "heart disease" then the interface will request specification of which family members have had this diagnosis and whether it was their cause of death. The user interface also provides space for free-text comments. If the user selects No, such as for "heart attack" and "high blood pressure" in this figure, then no further questions will be asked about those conditions.

Figure 16:
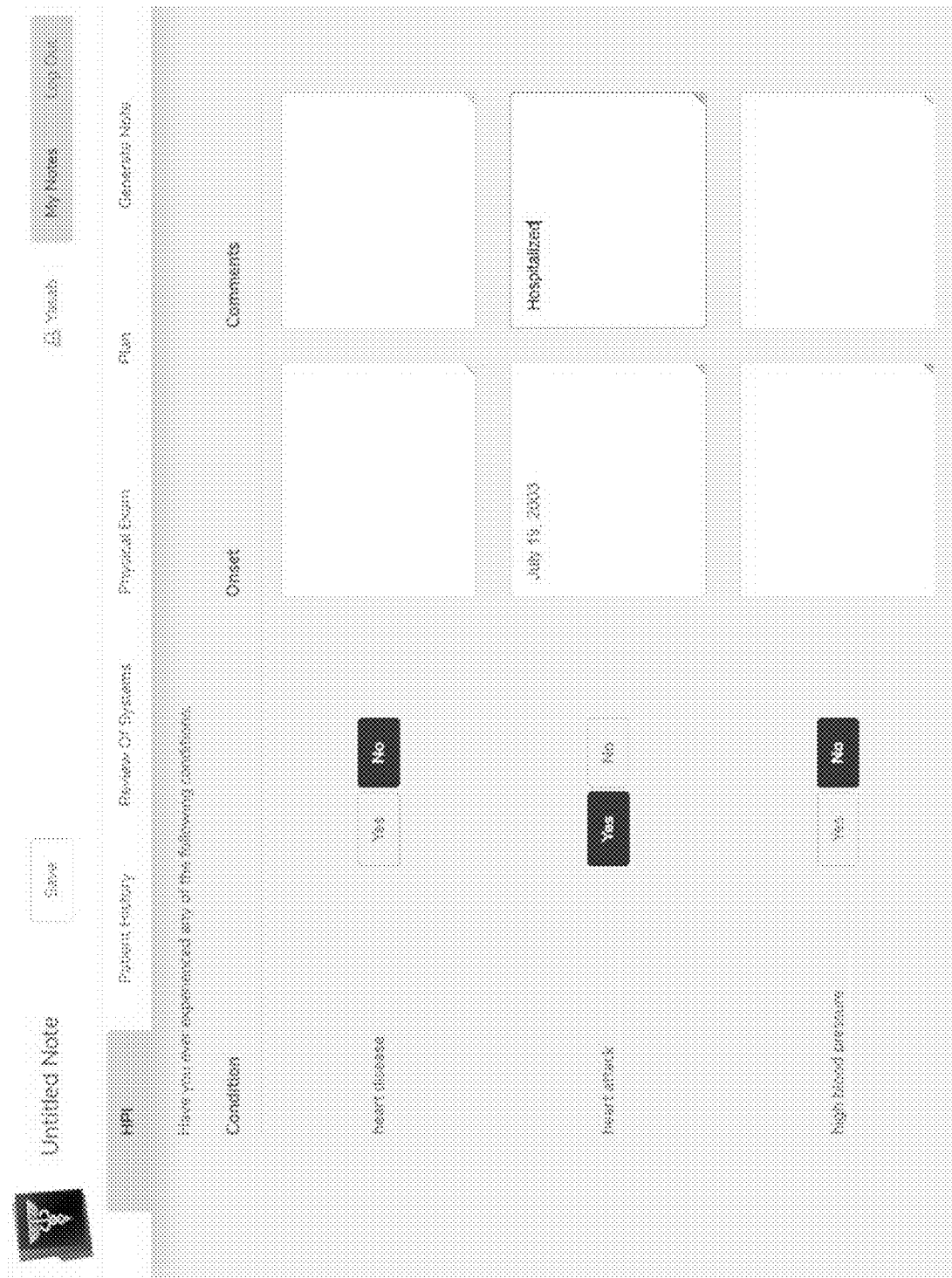

FIG. 16 is an example of a PMH-POP question, or past medical history prepopulated question, which the user had answered. A PMH-POP question enables sharing of state between the History of Present illness past medical history questions and the Past Medical History section of Patient History. The PMH-POP question enables the user to specify Yes or No for a particular list of conditions, shown as one condition per row. The user can also specify the Onset and put in free text Comments.

Figure 17:
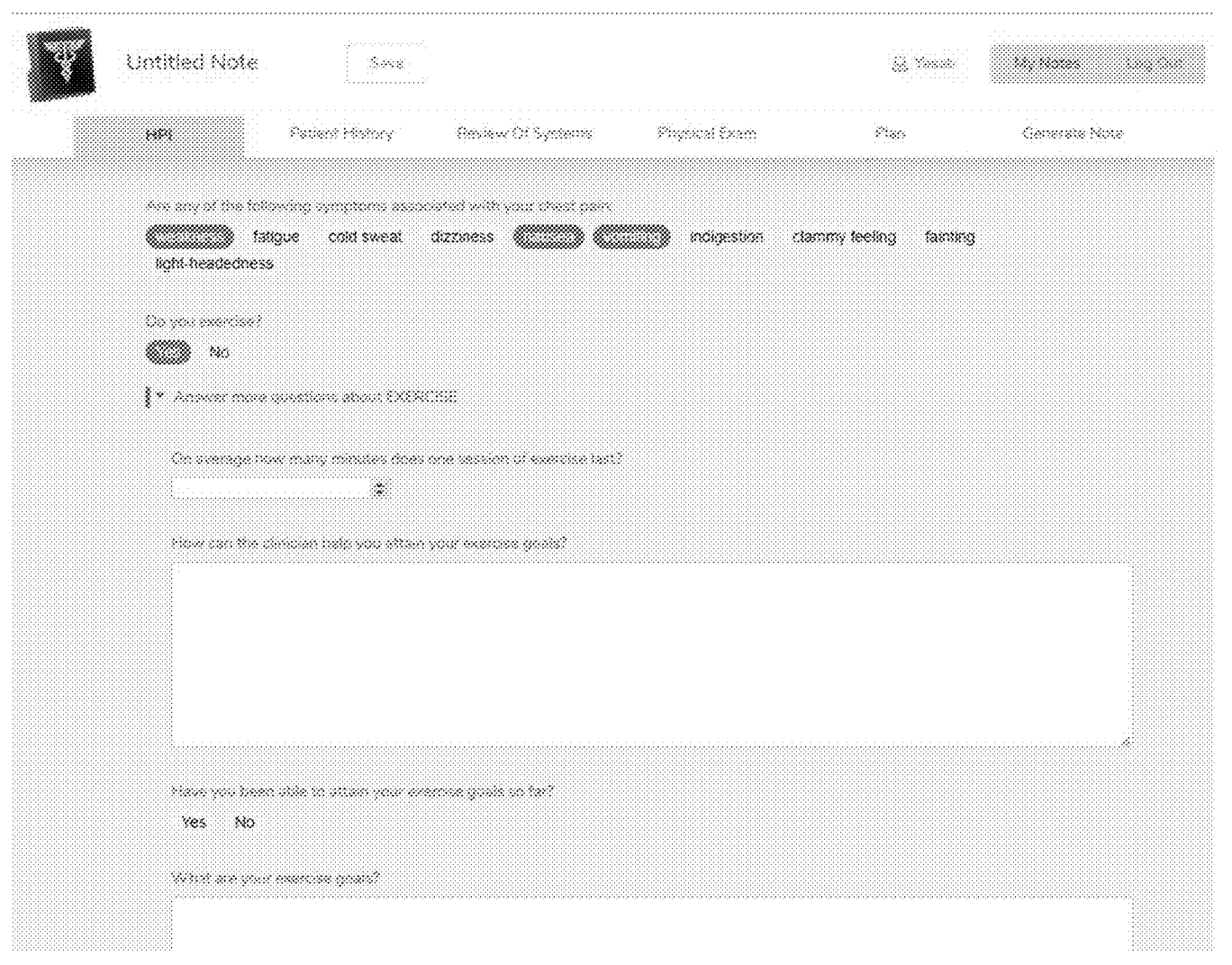

FIG. 17 is an example of how the History of Present Illness section may rely on a data structure that includes many different diseases or conditions. The question "Do you exercise?" has been answered with "Yes" which has triggered the system to pose child questions from an exercise data structure. Thus, the chest pain data structure has made a reference to the exercise data structure; they can conceptually be thought of as part of one large data structure that covers many different medical conditions.

Figure 18:
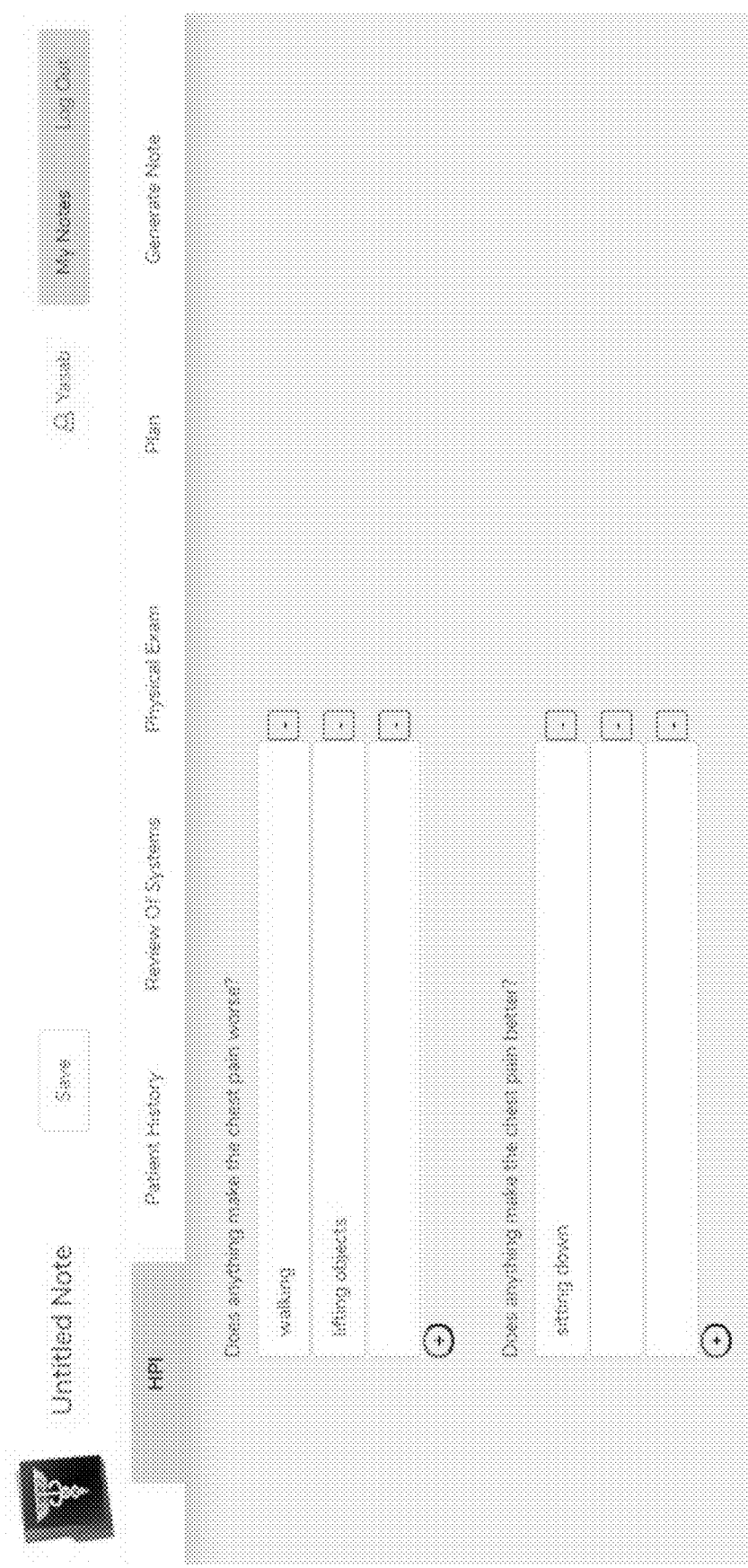

FIG. 18 is an example of two LIST-TEXT questions in the History of Present Illness. The user interface for LIST-TEXT questions is a list. The user can delete elements from the list using the minus button and can add elements to the list with the plus button. Example text has been entered in to the list for each question.

Figure 19:
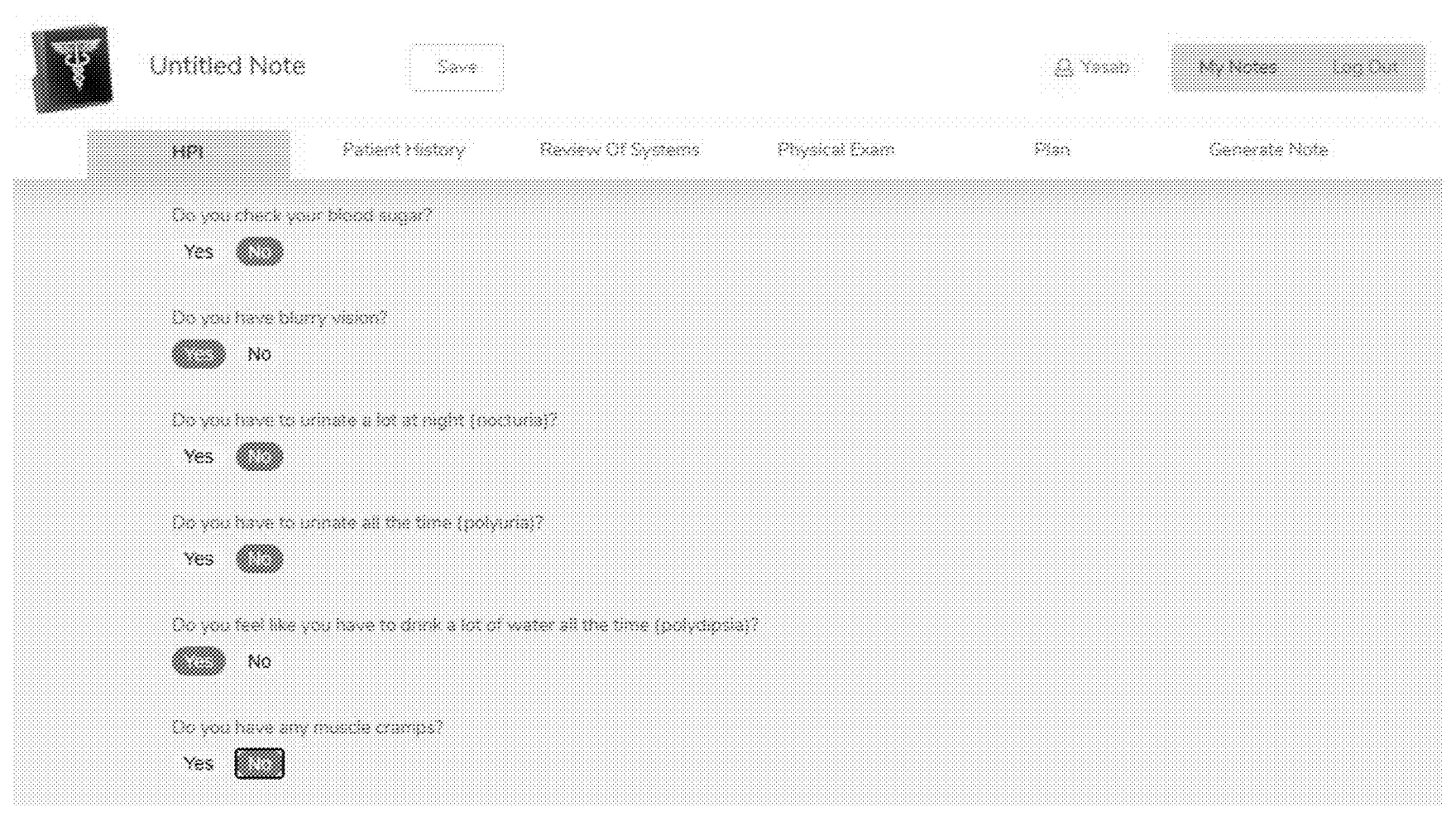

FIG. 19 is an example of some of the diabetes-related questions as part of the History of Present Illness section. The user has filled out responses to these questions.

Figure 20:
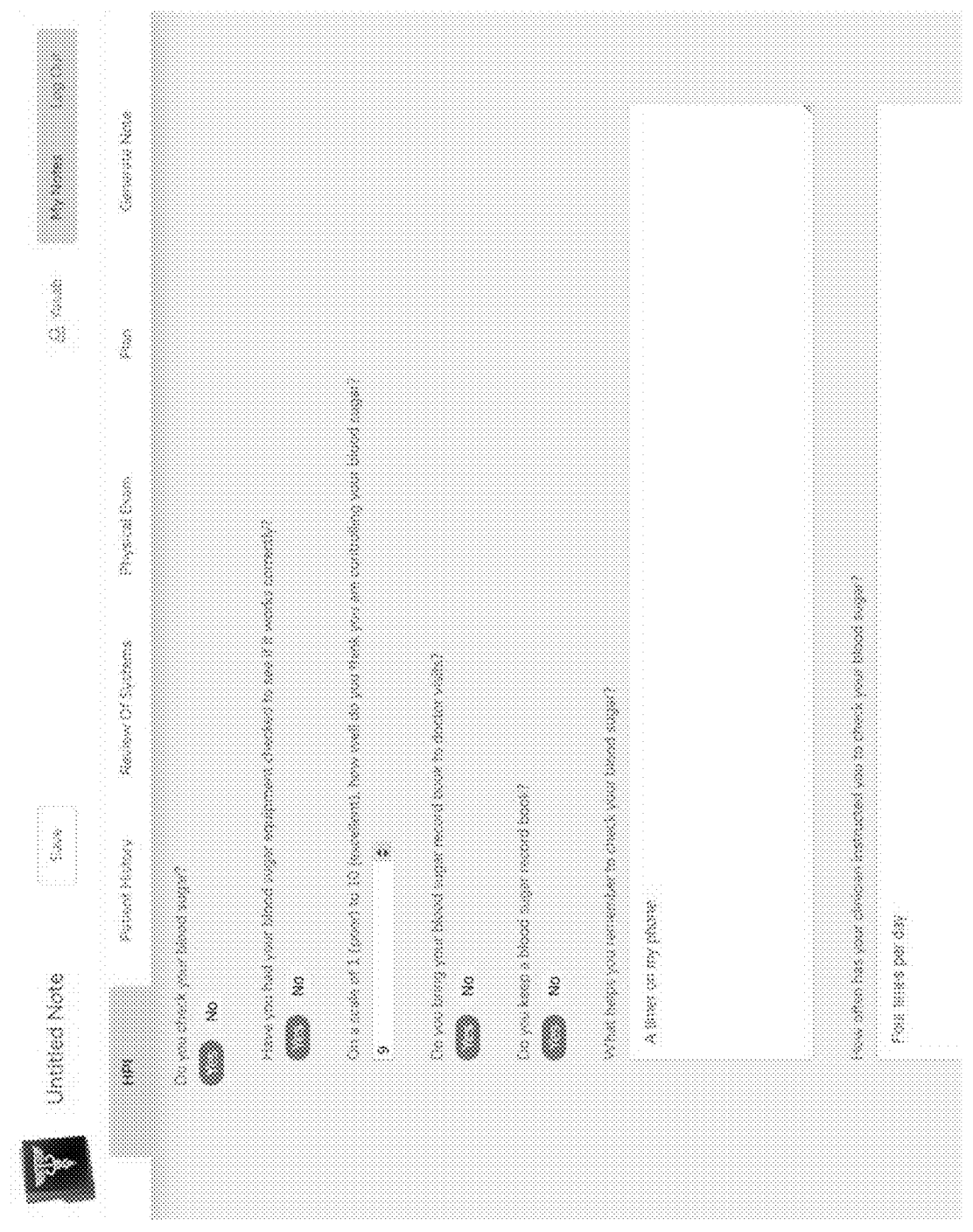

FIG. 20 when considered together with FIG. 19 exemplifies how the data structure may be traversed differently depending on how a user responds to questions. In FIG. 19 the user answered "No" to the question "Do you check your blood sugar?" and this caused no follow-up child questions to be asked. In FIG. 20 the user answered "Yes" to the question "Do you check your blood sugar?" and this caused multiple follow-up child questions to be asked, including "Have you had your blood sugar equipment checked to see if it works correctly?" and "Do you keep a blood sugar record book?" In this example the user has filled out responses to the follow-up child questions.

Figure 21:
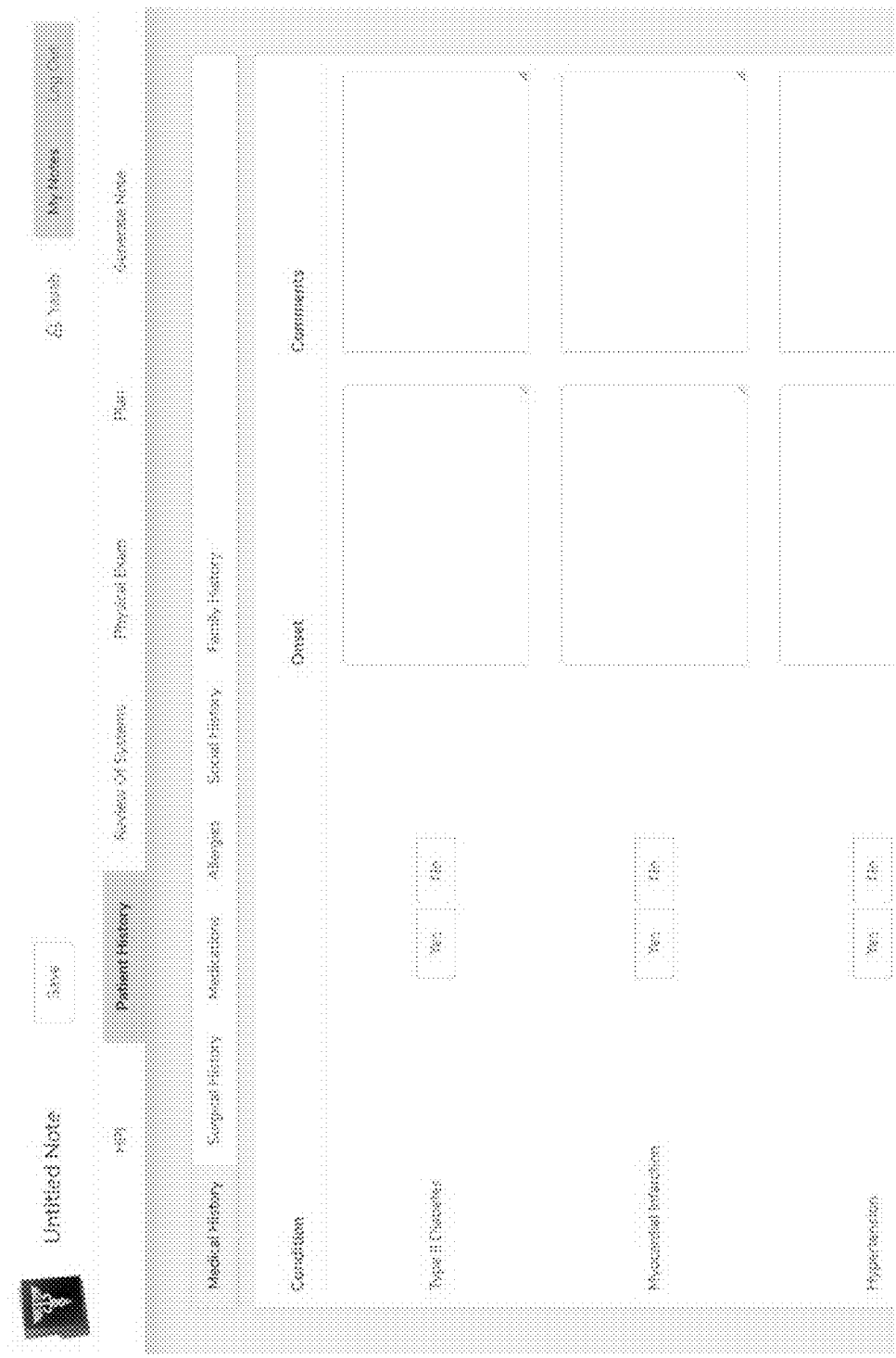

FIG. 21 is an example of a Past Medical History section. In this system the Past Medical History section is a sub-tab of a Patient History section. In the Past Medical History the user can specify a patient's personal history of certain predefined conditions (listed here as Type II Diabetes, Myocardial Infarction, and Hypertension). They can also enter history of custom conditions using a plus row option that is not explicitly shown.

Figure 22:

FIG. 22 is another example of a Past Medical History section. In this example, the user can specify a patient's personal history of predefined or custom conditions. For each condition the user can specify whether or not the patient has it (the first Yes vs No buttons), the Start Year of the condition, whether or not the condition has resolved, the End Year of the condition (if the condition has resolved), and comments.

Figure 23:
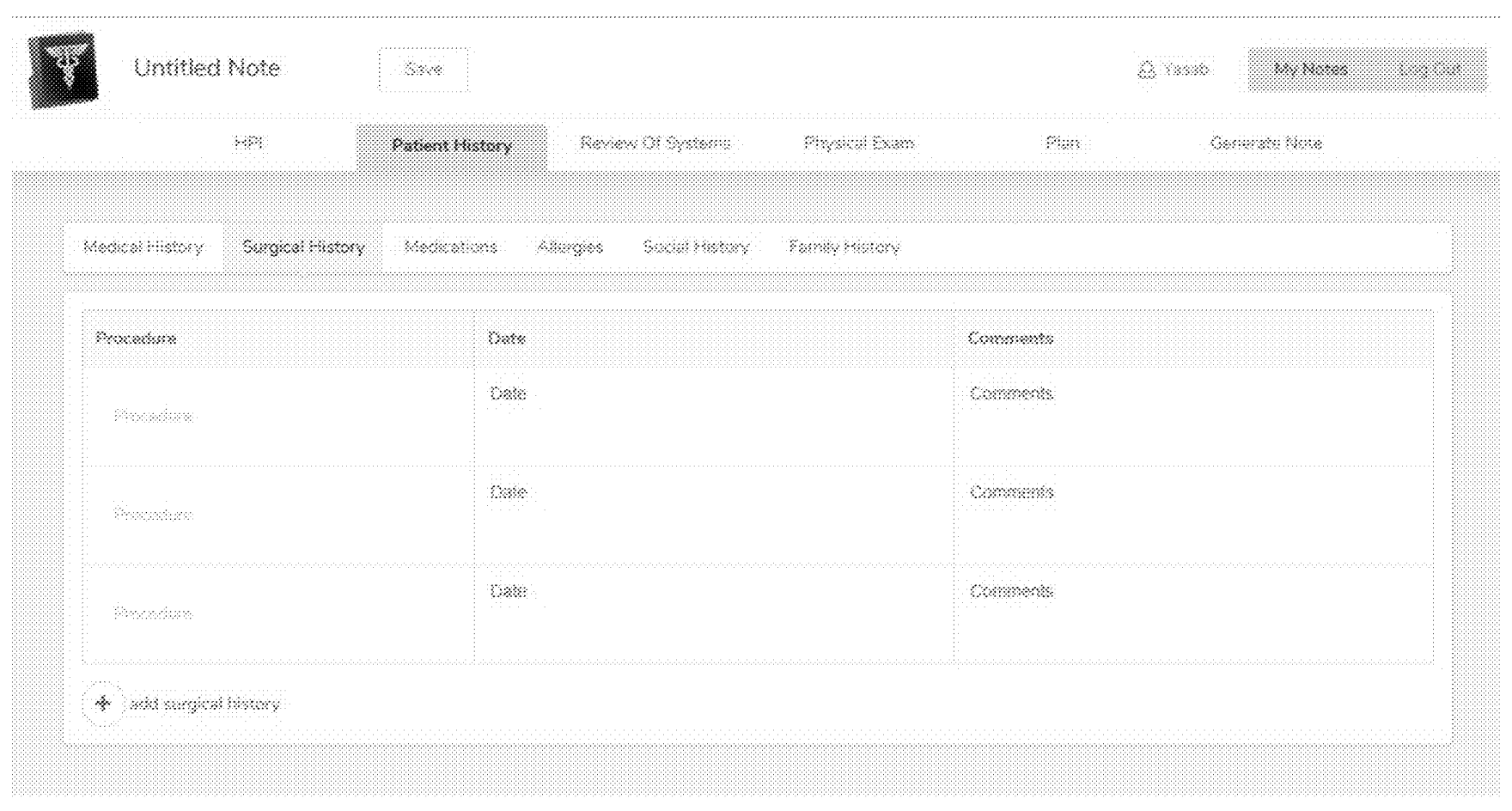

FIG. 23 is an example of a Surgical History section. In this system the Surgical History section is a sub-tab of a Patient History section. In the Surgical History section the user can specify previous procedures, their date, and comments.

Figure 24:
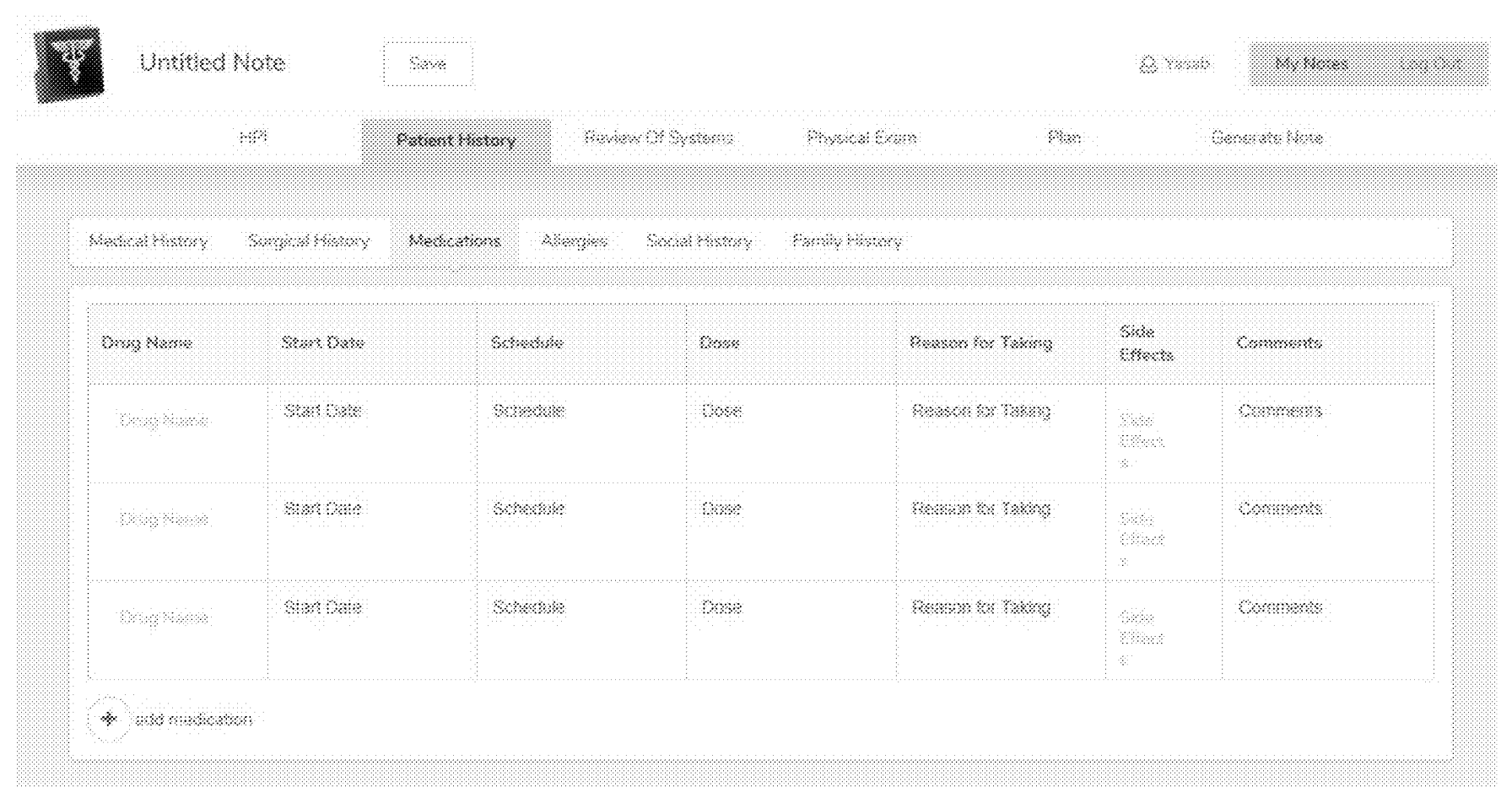

FIG. 24 is an example of a Medications section. In this system the Medications section is a sub-tab of a Patient History section. In the Medications section the user can specify medications according to their names, start date, schedule (i.e. how often they take it), dose, reason for taking (e.g. a particular disease), side effects if any, and free text comments.

Figure 25:
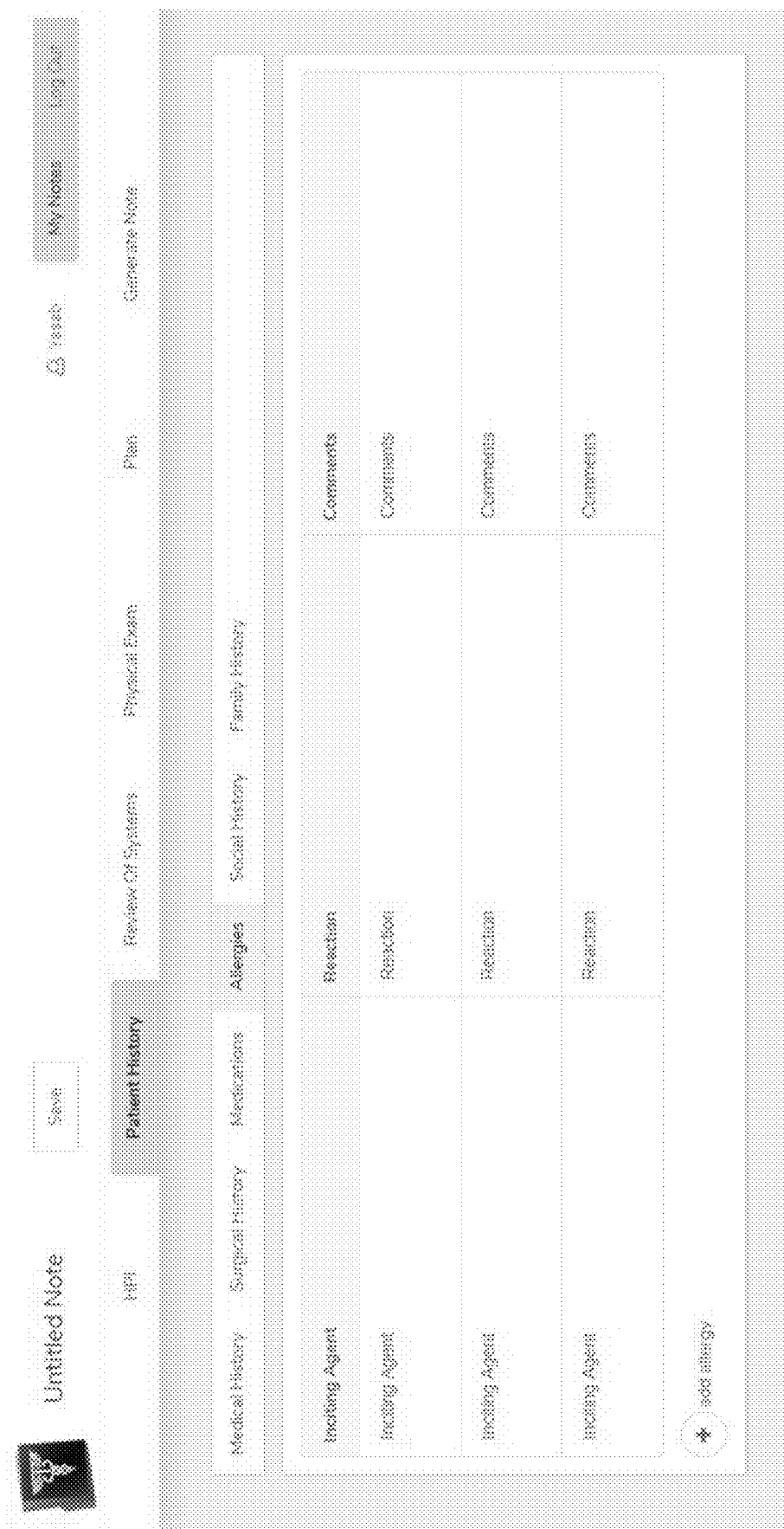

FIG. 25 is an example of an Allergies section. In this system the Allergies section is a sub-tab of a Patient History section. In the Allergies section the user can specify allergies according to the inciting agent (e.g. pollen, bees, peanuts), reaction (e.g. hives, itching, sneezing), and free-text comments.

Figure 26:
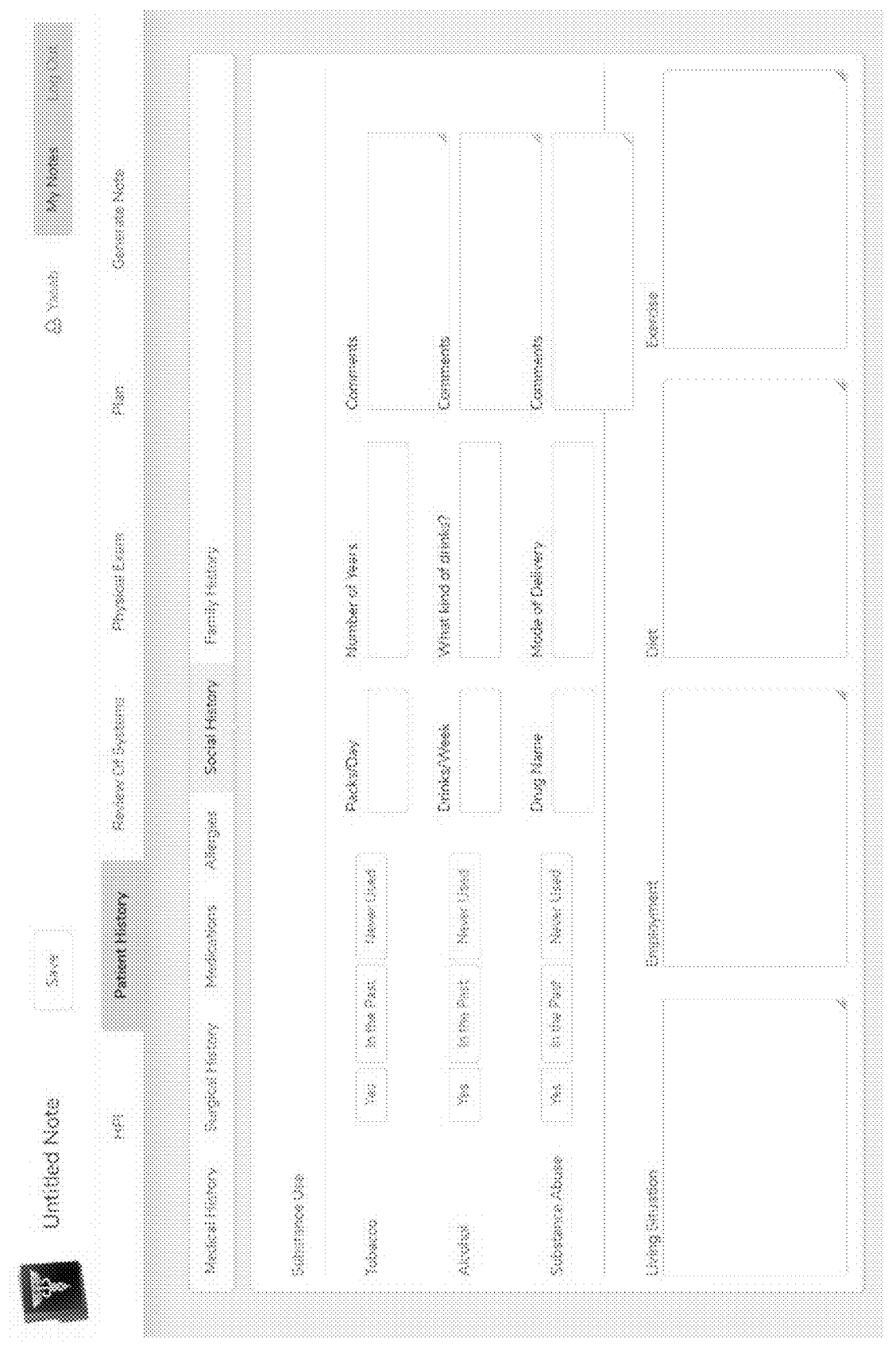

FIG. 26 is an example of a Social History section. In this system the Social History section is a sub-tab of a Patient History section. In the Social History section the user can specify various aspects of their social history. Social History may include substance use such as tobacco (including packs per day and total number of years), alcohol (including drinks per week and type of drinks), and recreational drugs (including their names and modes of delivery). The Social History may also include descriptions of living situation, employment, diet, and exercise.

Figure 27:
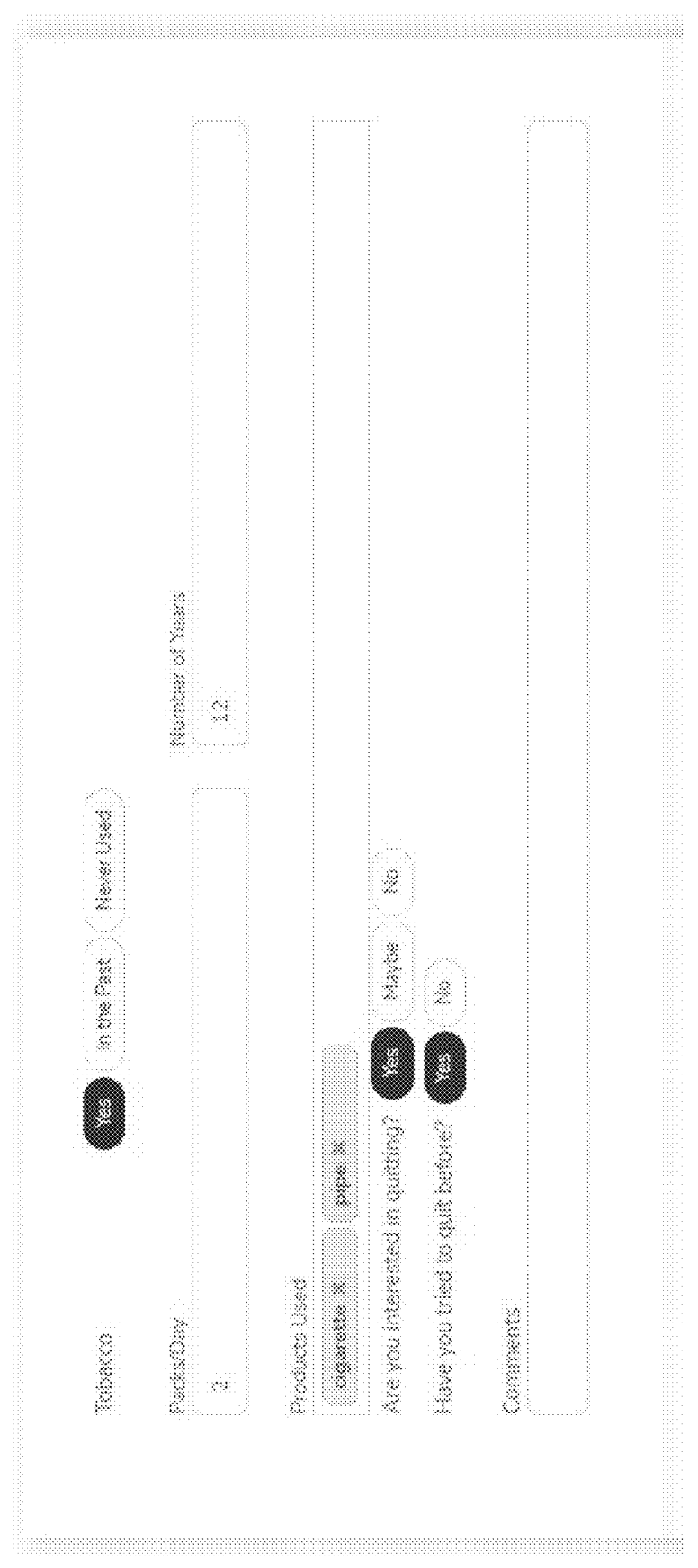

FIG. 27 is an example of a part of a Social History section for describing Tobacco use. In this example the user has selected "Yes" to indicate that the patient does use tobacco. Because the user selected "Yes" additional follow-up questions are posed, including the Packs/Day (filled in here as 2), the Number of Years (filled in here are 12), the products used (filled in here as cigarette and pipe), whether the patient is interested in quitting (filled in here as Yes), and whether the patient has tried to quite before (filled in here as Yes).

Figure 28:
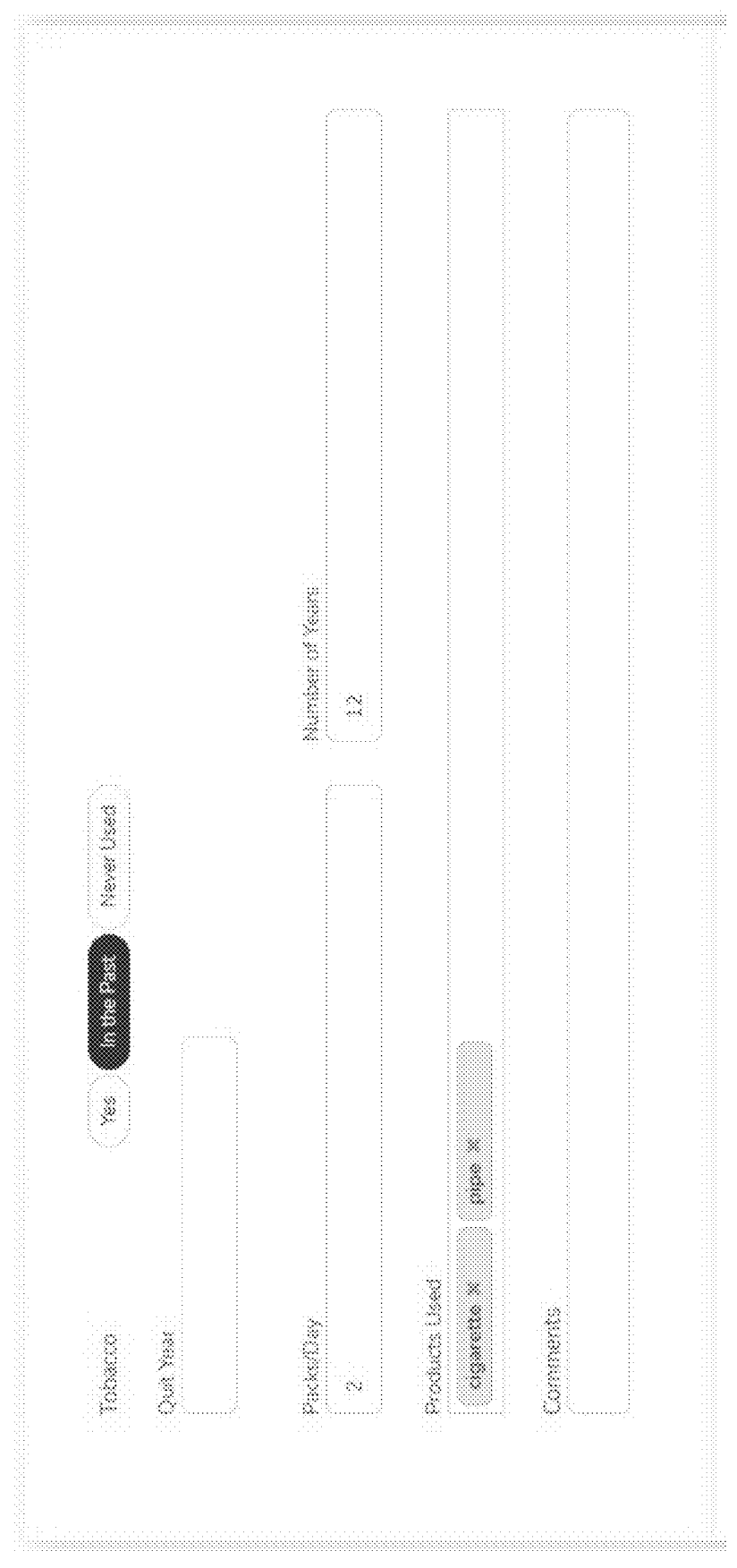

FIG. 28 is an example of a part of a Social History section for describing Tobacco use. In this example the user has selected "In the Past" to indicate that the patient previously used tobacco but does not any more. Because the user selected "In the Past" additional follow-up questions are posed, including the Quit Year (the year in which the patient stopped using tobacco). In this example Packs/Day, Number of Years, and Products Used are filled out.

Figure 29:
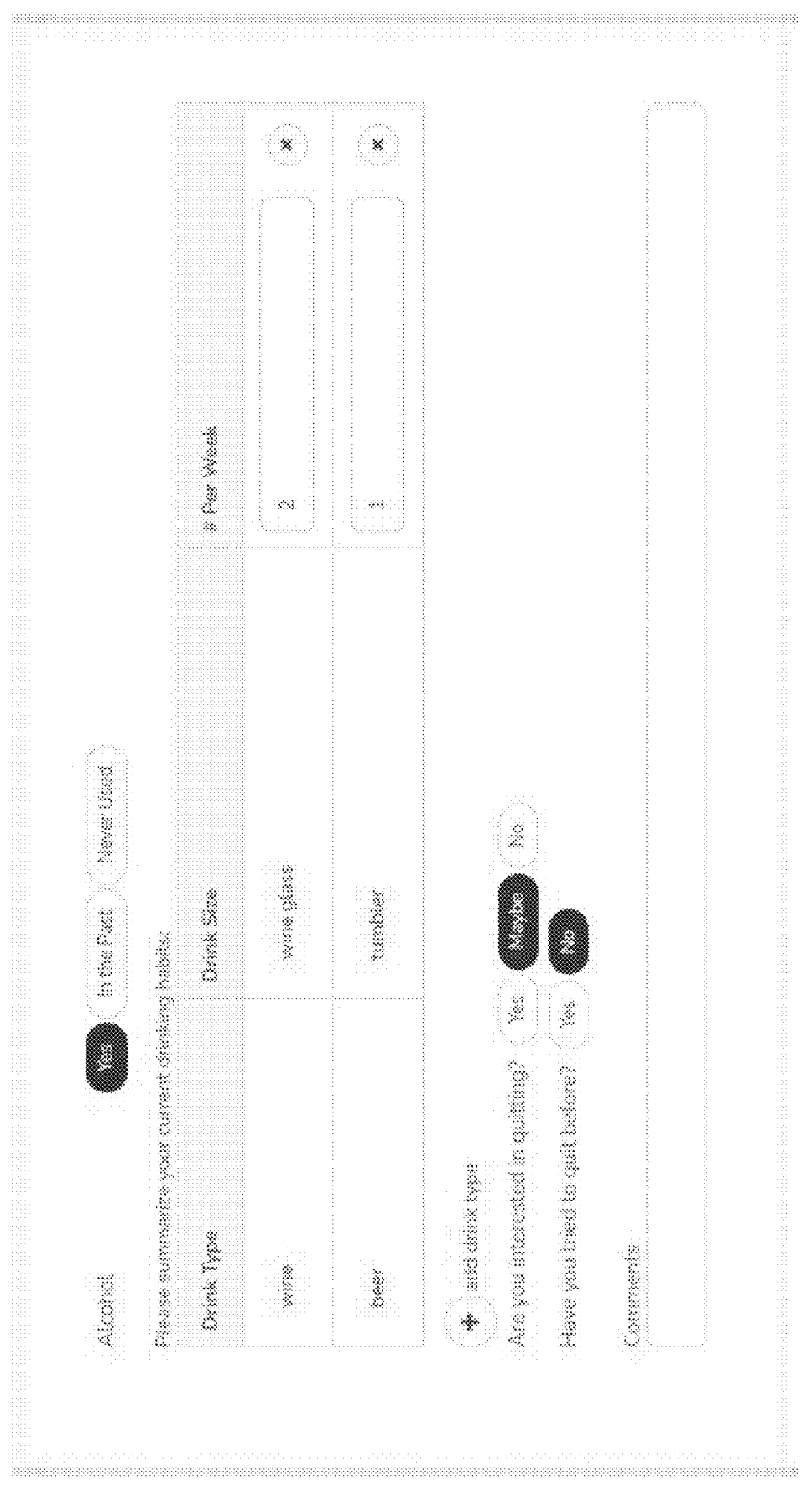

FIG. 29 is an example of a part of a Social History section for describing Alcohol use. In this example the user has selected "Yes" to indicate that the patient does use alcohol. Because the user selected "Yes" additional follow-up questions are posed, including a summary of drinking habits in tabular form (filled in here as 2 glasses of wine and 1 tumbler of beer per week), whether the patient is interested in quitting (filled in here as "Maybe") and whether the patient has tried to quit before (filled in here as "No.")

Figure 30:
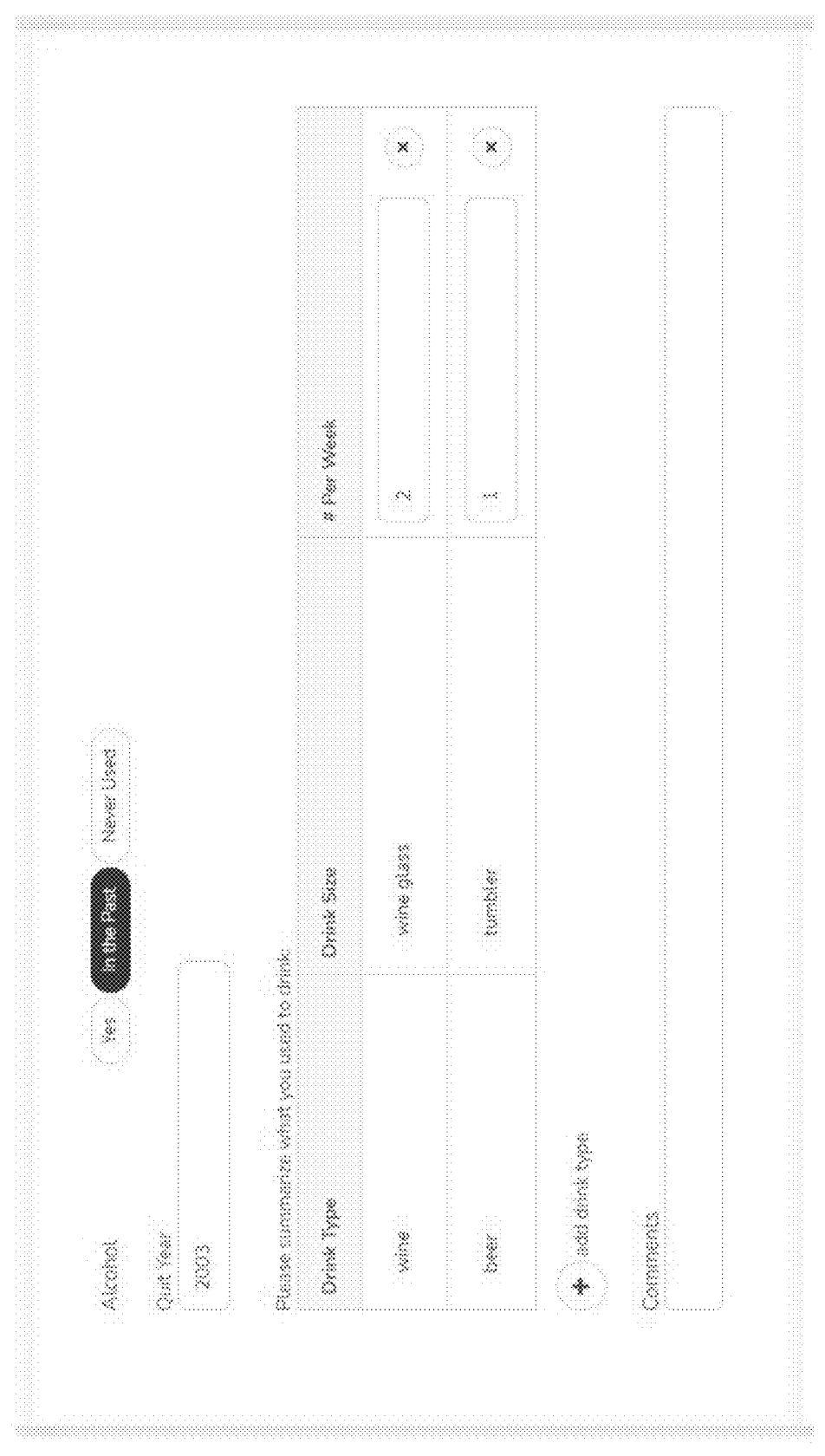

FIG. 30 is an example of a part of a Social History section for describing Alcohol use. In this example the user has selected "In the Past" to indicate that the patient previously used alcohol. Because the user selected "In the Past" additional follow-up questions are posed, including the Quit Year (the year in which the patient stopped using alcohol, filled in here as 2003). The interface also allows the user to specify the patient's previous drinking habits.

Figure 31:
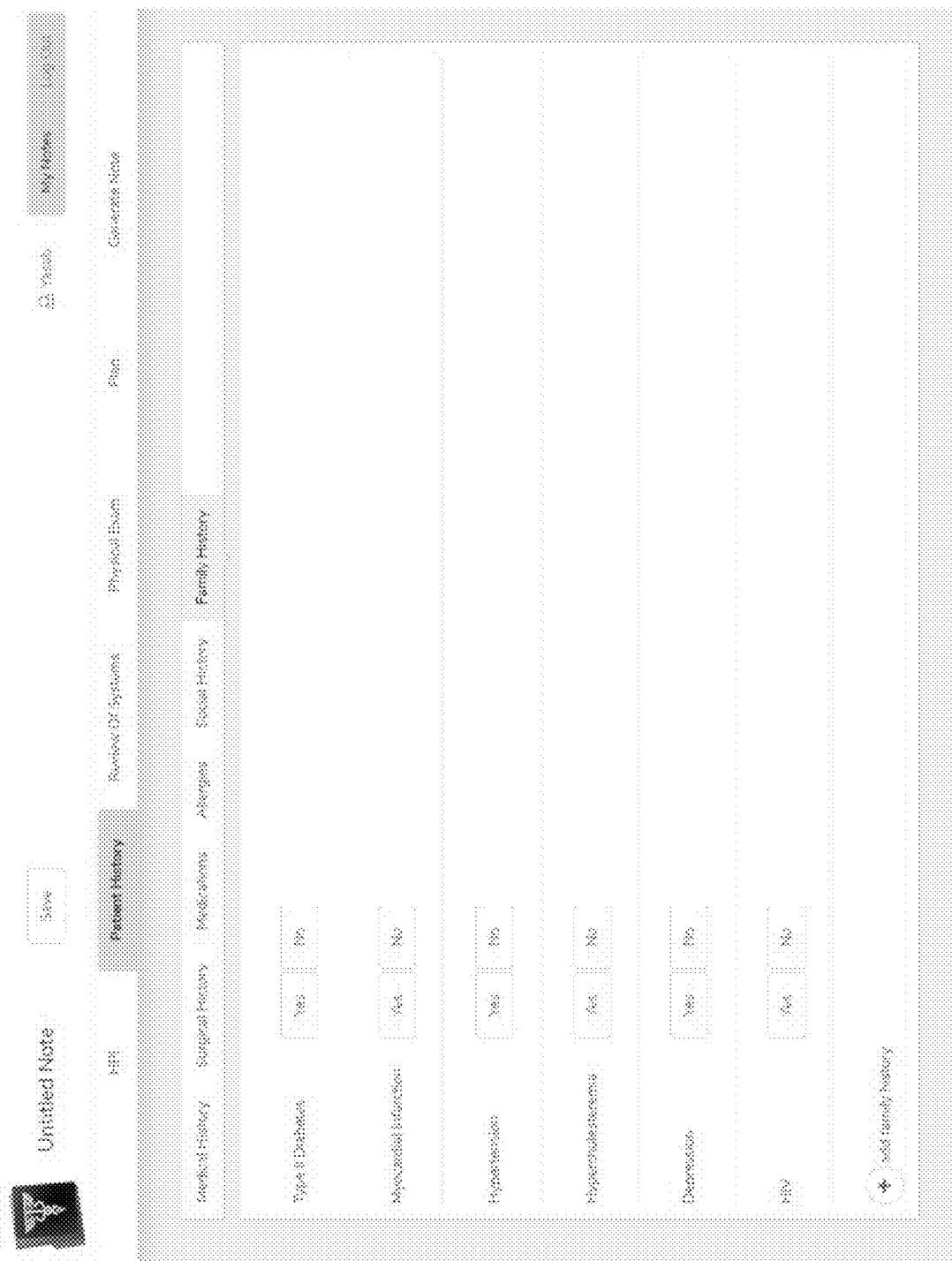

FIG. 31 is an example of a Family History section. In this system the Family History section is a sub-tab of a Patient History section. In the Family History section the user can specify whether they have a family history of certain conditions which may be pre-defined, or custom. Custom family history conditions can be added using the plus button at the bottom that says "+ add family history." Further details of the Family History interface are provided in FIGS. 14 and 15.

Figure 32:
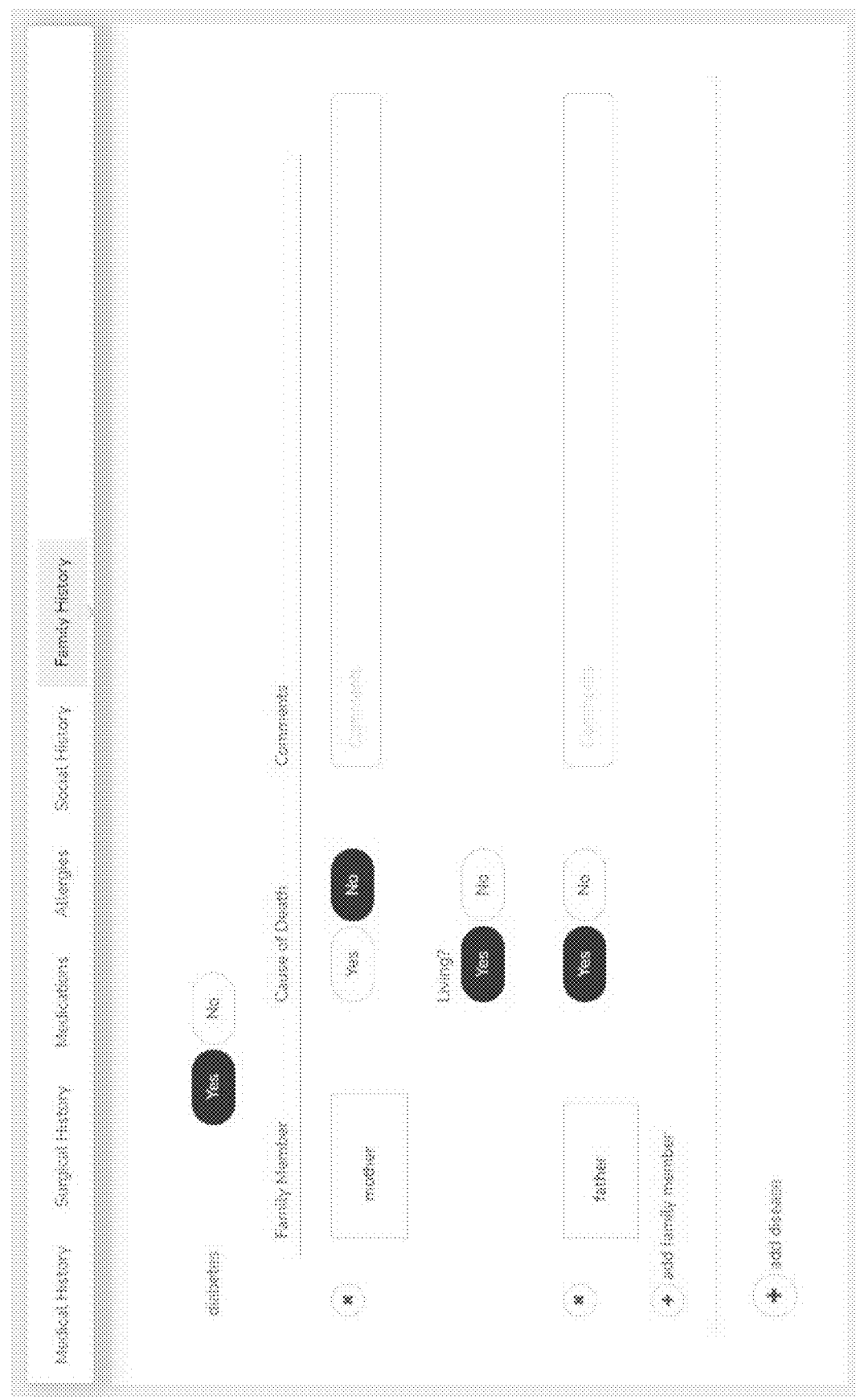

FIG. 32 is another example of a Family History section. In this interface, the user can specify whether the patient has a family history of any particular condition (in this example, "diabetes"). Because the user has selected "Yes" here for a patient having a family history of diabetes, the interface allows entering more detailed information including the family member or family members affected (in this example, "mother" and "father") and for each family member whether it was their cause of death. For "mother" the cause of death option has been selected "No" in this example prompting a follow up question of whether the mother is still living (filled out as "Yes" here). For "father" the cause of death option has been selected "Yes." A button "+ add family member" when clicked will allow the user to add additional family members who have diabetes. A button "+ add disease" will allow the user to add additional diseases found in the patient's family history.

FIG. 33 is an example of the top part of a Review of Systems section in which the user has not yet selected any responses. Each body system is displayed on a card. Different symptoms related to that body system are displayed within the card, with a NO button and a YES button so that the user can indicate whether the symptom is occurring.

Figure 34:
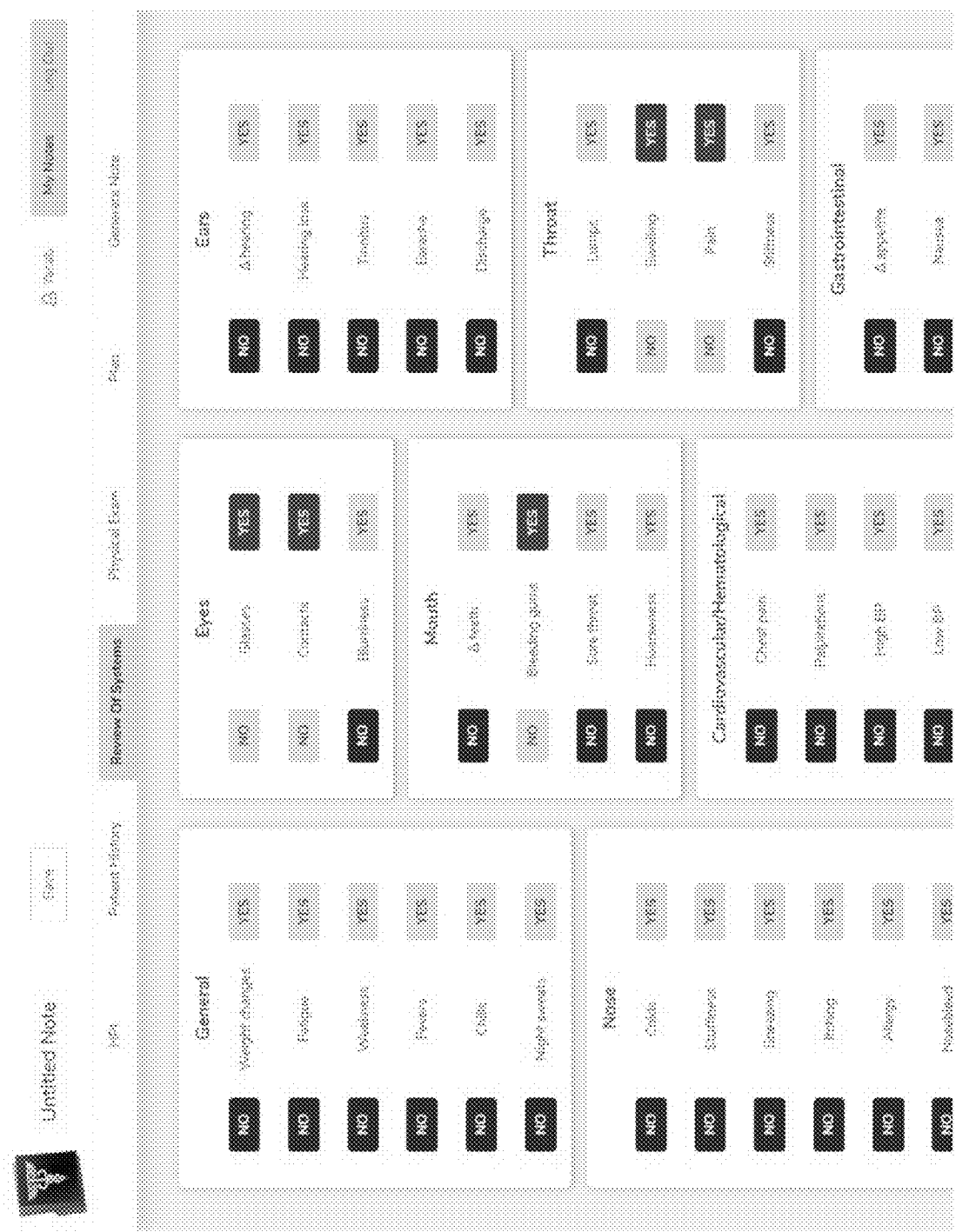

FIG. 34 is an example of the top part of a Review of Systems section in which the user has selected responses. The No responses are shown in green because this indicates health, or the absence of a symptom; the Yes responses are shown in red because this indicates disease, or the presence of a symptom. The Yes and No buttons are shown on opposite sides of the word to minimize the risk of accidentally clicking the wrong response. The display is responsive so that when the screen changes sizes, a different number of blocks will be shown horizontally. On a mobile device one block will be shown at a time and the user can scroll down through all the blocks for all the body systems.

Figure 35:
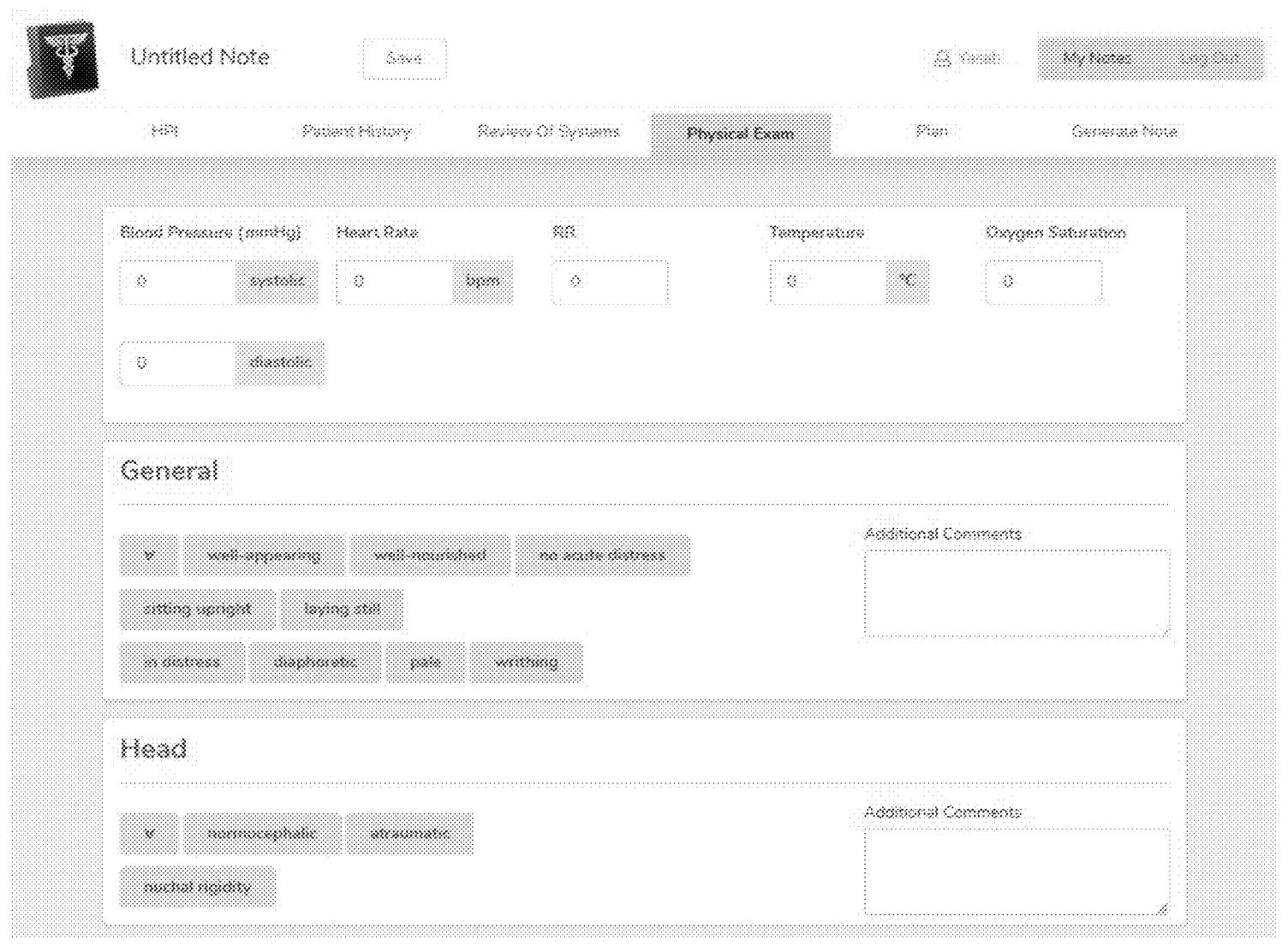

FIG. 35 shows part of a Physical Exam section, specifically the vitals at the top, General, and Head, in which the user has not yet filled in responses. Vitals include blood pressure, heart rate, respiratory rate (RR), temperature, and oxygen saturation. General includes the patient's overall appearance. Head includes descriptions of the patient's head. The buttons that has the upside-down "A" on it (the "for all" symbol in mathematics) represents a button which when clicked will automatically select all of the buttons in its row. Which buttons appear together in a row has been strategically chosen to reflect the way that clinicians perform physical examinations and which findings tend to be observed together. The strategic grouping of particular physical exam findings along with the "for all" button is an example of a user interface design choice intended to accelerate entry of information.

Figure 36:
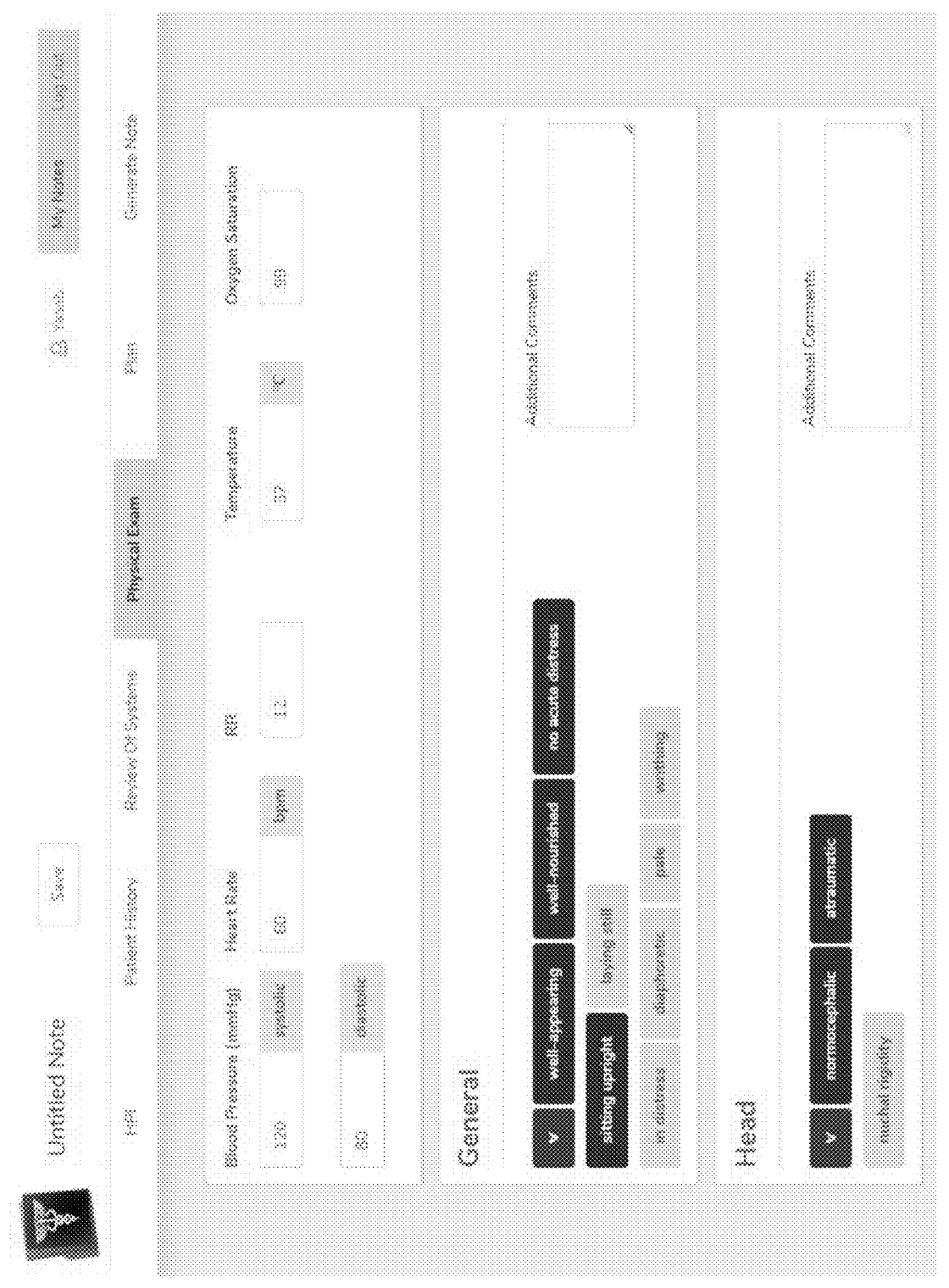

FIG. 36 shows part of a Physical Exam section, specifically the vitals, General, and Head, in which the user has filled in responses. The vital signs have been filled in by entering numbers. The General and Head sections have been filled in by clicking buttons. The "for all" button was used to enable clicking all buttons in one row together.

Figure 37:
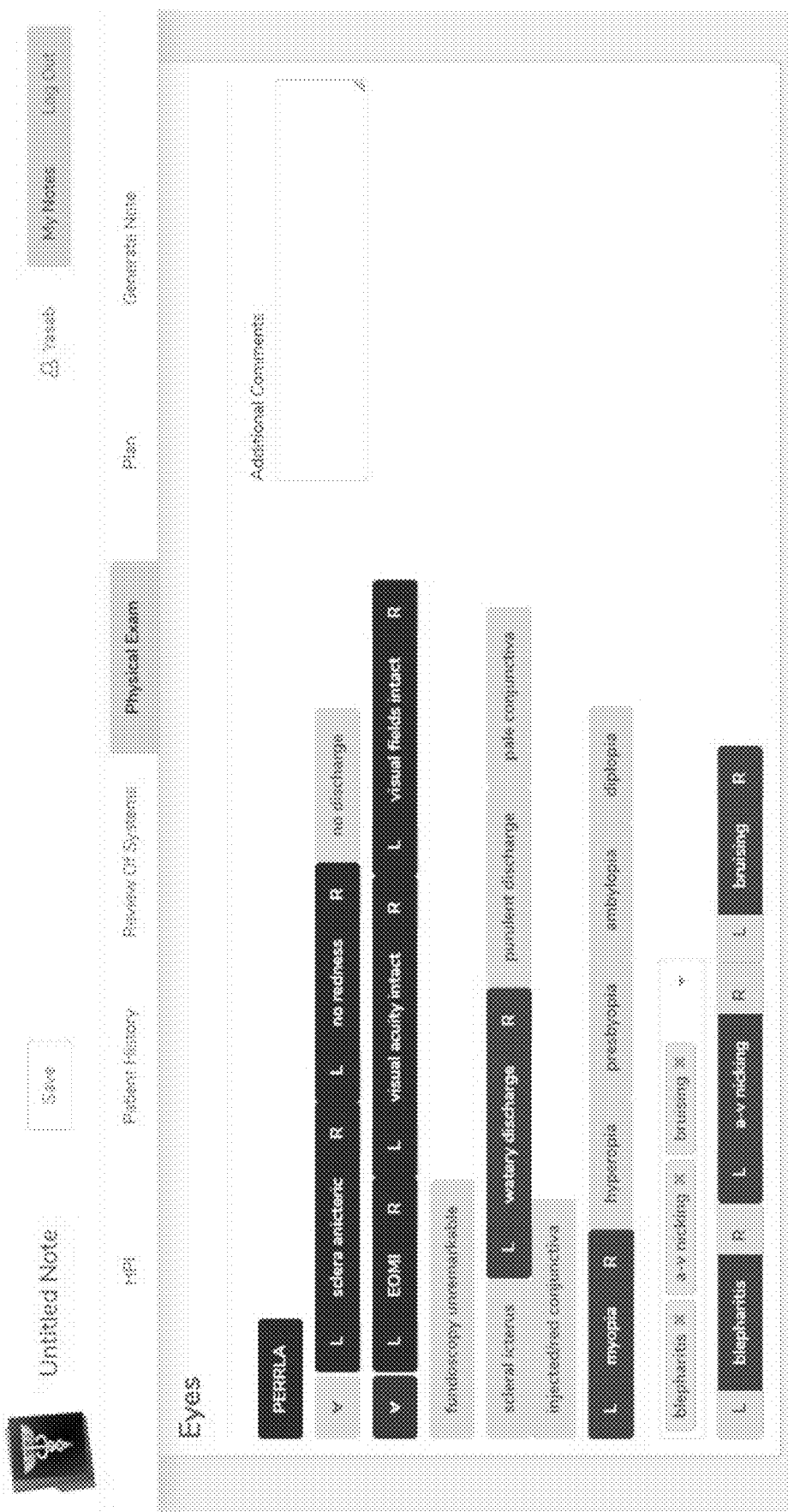

FIG. 37 shows part of a Physical Exam section, specifically the section for the Eyes, in which the user has filled in responses. Normal findings are shown at the top while abnormal findings are shown at the bottom. When normal findings are clicked they turn green. When abnormal findings are clicked they turn red. This section exemplifies the Left-Right button functionality. In the Left-Right button functionality, when a user clicks on a button for a finding that may occur on the left and/or on the right, an L button shows up on the left and an R button shows up on the right. The user can select L to indicate that the finding is seen on the Left, and they can select R to indicate that the finding is seen on the Right. If they leave L unselected it implies that the finding is not seen on the Left. If they leave R unselected it implies that the finding is not seen on the Right. In the figure, a-v nicking is seen on the left, bruising is seen on the right, and watery discharge is seen on both the left and the right. At the bottom, there is a drop-down menu from which the user can select rarer findings; in this example they have selected blepharitis, a-v nicking, and bruising. When the user selected these findings from the drop-down menu they appeared as buttons with the Left-Right functionality. If the user wishes to remove these findings, they can click the "x" in the drop-down menu next to the finding name.

Figure 38:
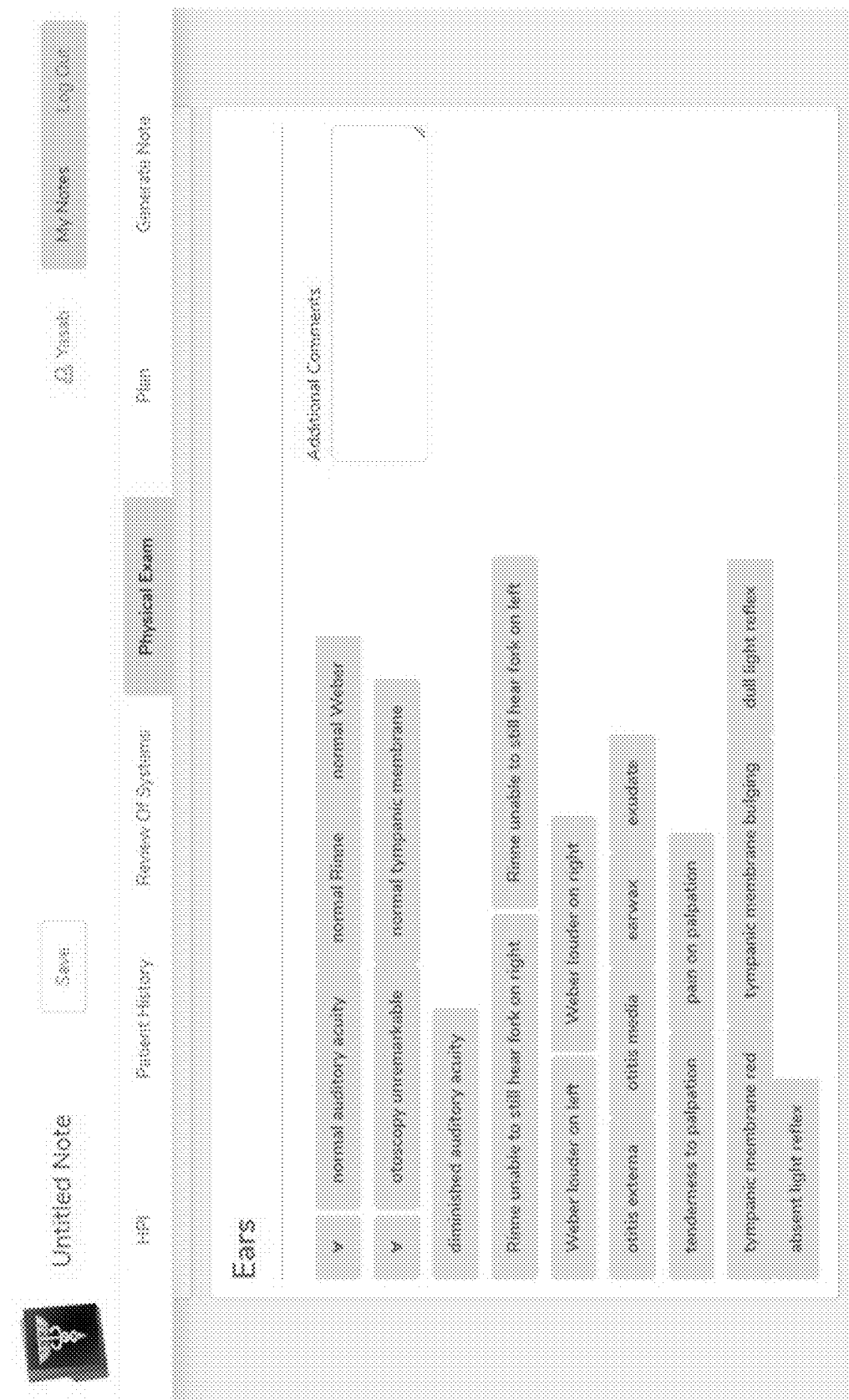

FIG. 38 shows part of a Physical Exam section, specifically the section for the Ears.

Figure 39:
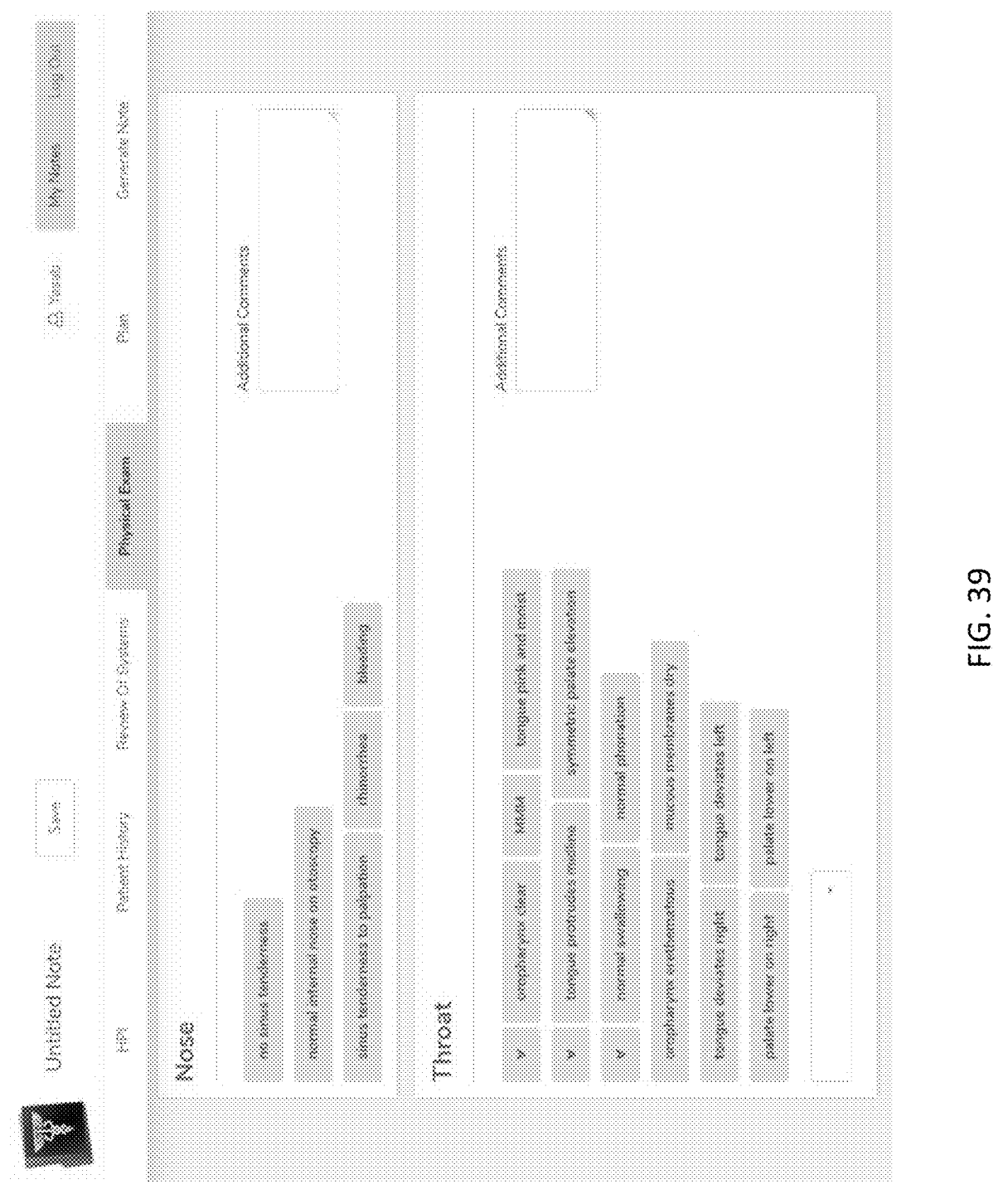

FIG. 39 shows part of a Physical Exam section, specifically the sections for the Nose and Throat.

Figure 40:
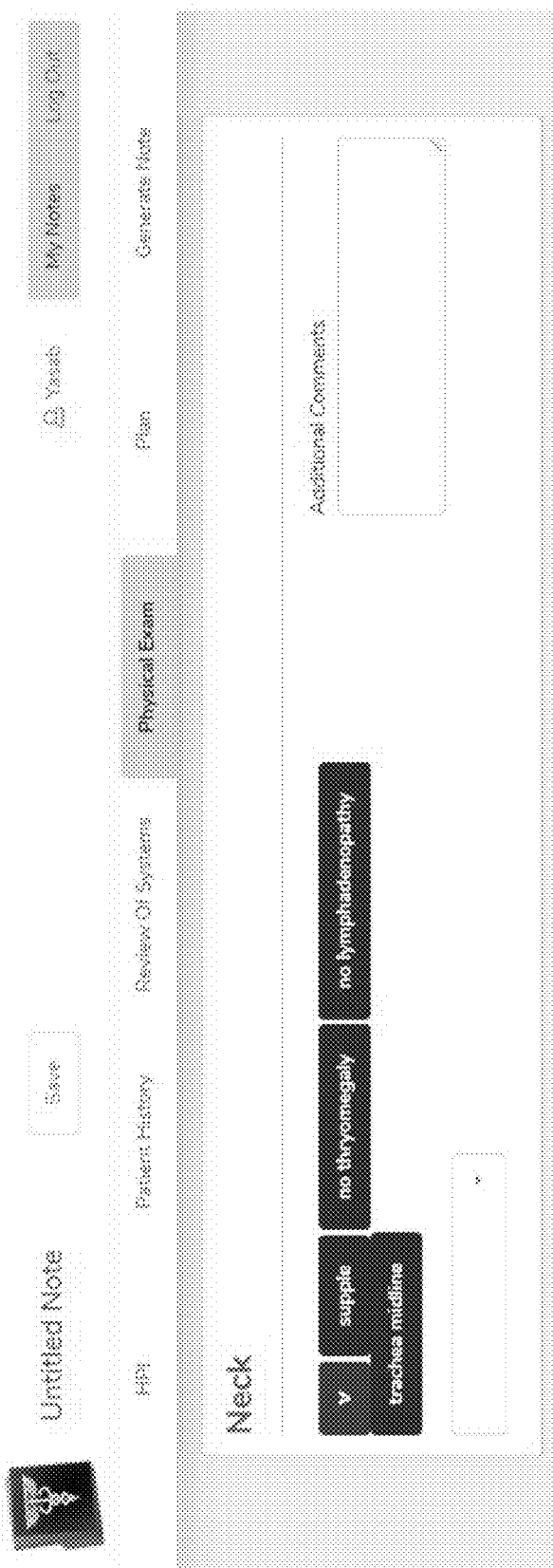

FIG. 40 shows part of a Physical Exam section, specifically the section for the Neck. Here, the "for all" button has been used to select everything in the group "supple, no thyromegaly, no lymphadenopathy, trachea midline."

Figure 41:
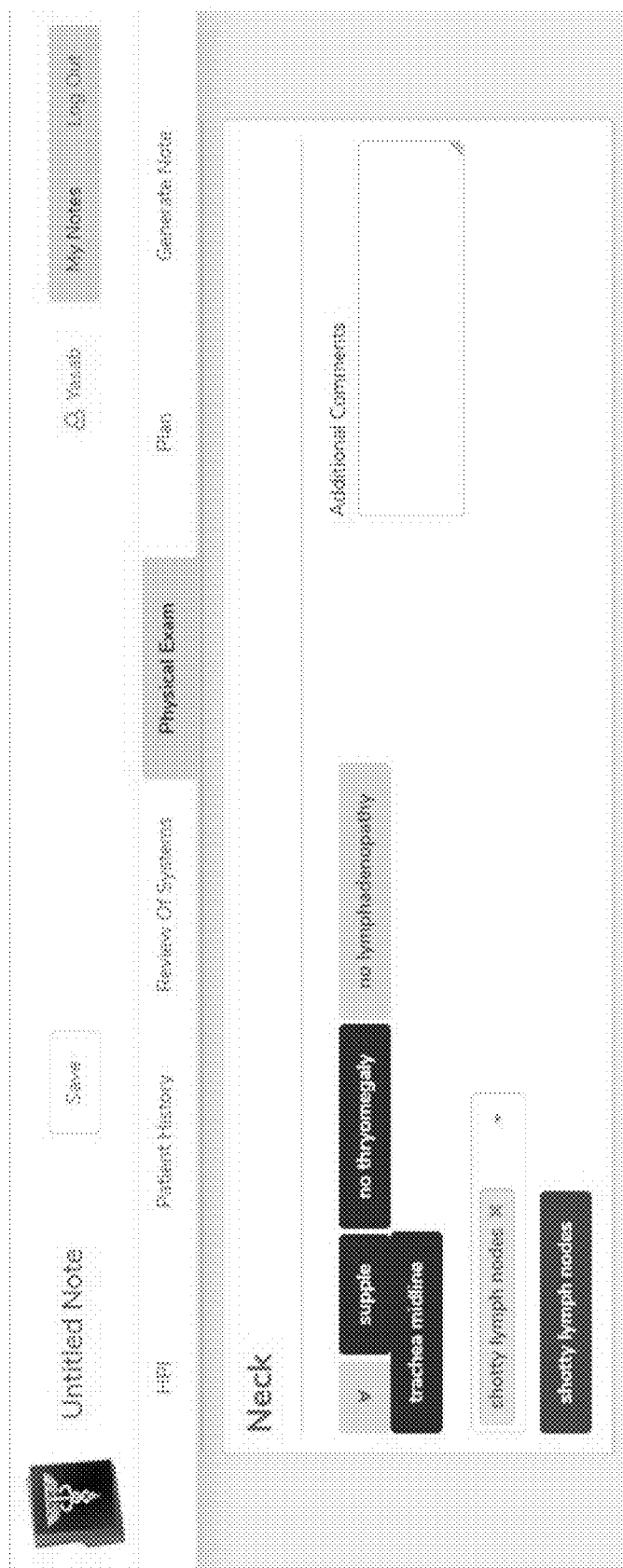

FIG. 41 shows part of a Physical Exam section, specifically the section for the Neck. Here, the user has selected some normal findings and one abnormal finding from the drop-down menu, "shotty lymph nodes."

Figure 42:
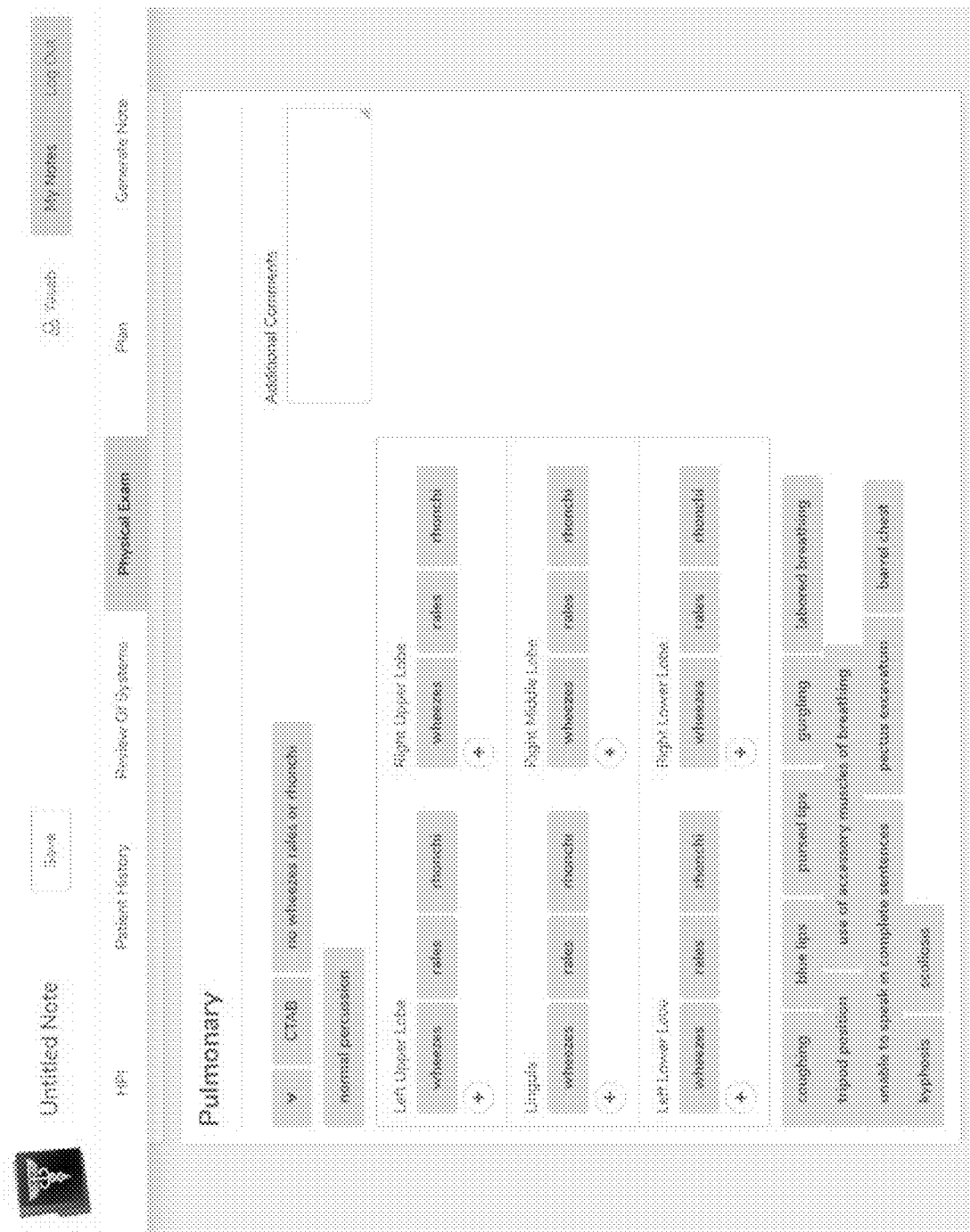

FIG. 42 shows part of a Physical Exam section, specifically the section for the lungs (Pulmonary). The Pulmonary section includes a widget for lung sounds which is organized with the left upper lobe, lingula, and left lower lobe on the left, and the right upper lobe, right middle lobe, and right lower lobe on the right, following the anatomical layout of these lung locations when facing a patient's back. For each lung location the user can select wheezes, rales, or rhonchi as the sound, or additional sounds using the plus button.

Figure 43:
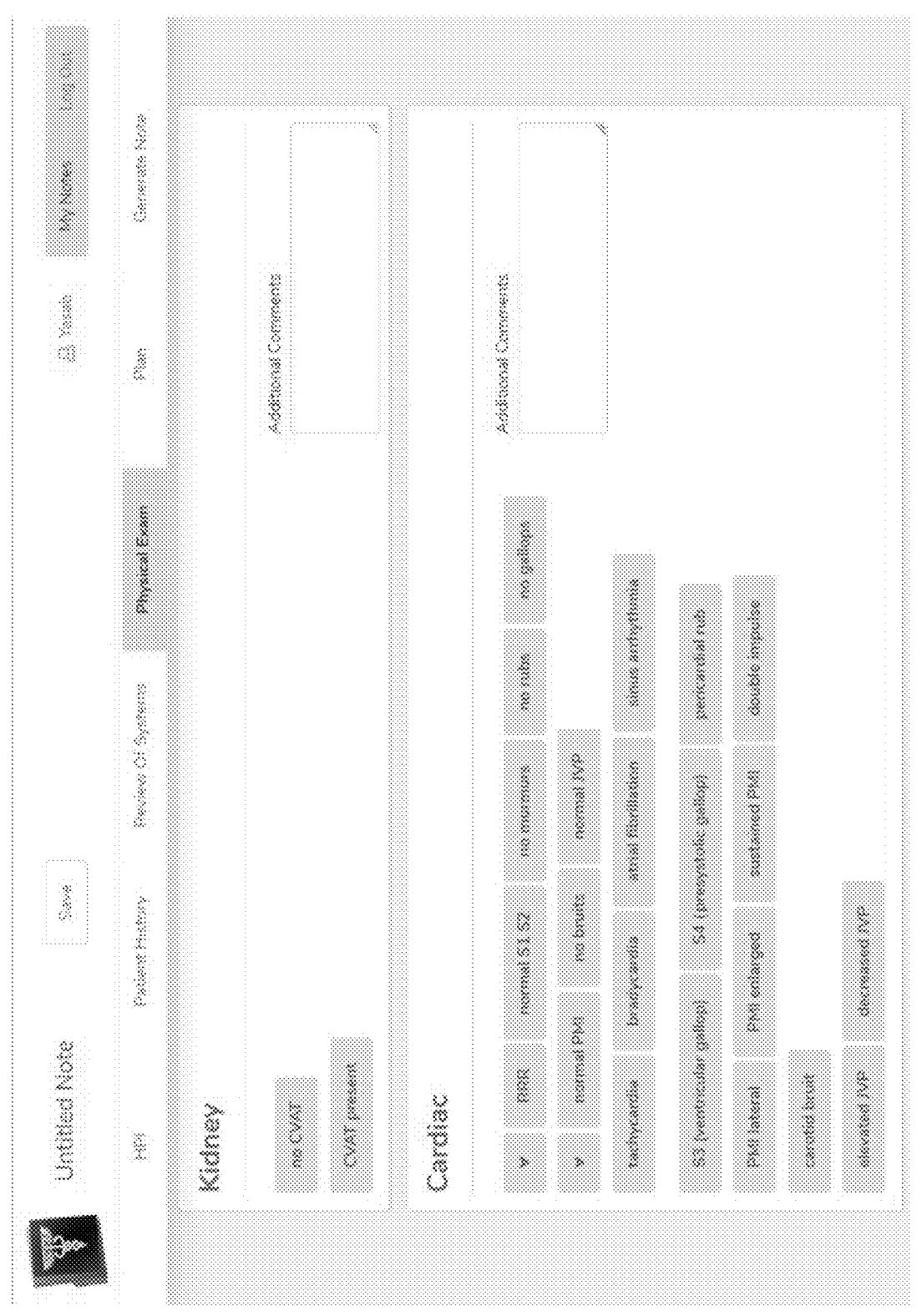

FIG. 43 shows part of a Physical Exam section, specifically the sections for Kidney and Cardiac.

FIG. 44 shows part of a Physical Exam section, specifically examples of the Cardiac Murmurs widget. There are two examples of the widget shown, one where "systolic" is selected and the other where "diastolic" is selected. When "systolic" is selected, the lower section of the widget displays different options than when "diastolic" is selected. The upper section of the widget always shows the same options for describing the heart murmur: crescendo/decrescendo/crescendo-decrescendo, heart best at the RUSB/LUSB/RLSB/LLSB/apex (RUSB=right upper sternal border, LUSB=left upper sternal border, RLSB=right lower sternal border, LLSB=left lower sternal border), intensity in range 1-5, pitch low/medium/high, and quality blowing/harsh/rumbling/whooshing/rasping/musical. The lower section of the widget relates to specific murmurs and changes depending on whether systolic or diastolic is selected. When systolic is selected, various names and properties of systolic murmurs are shown in the lower section of the widget. When diastolic is selected, various names and properties of diastolic murmurs are shown in the lower section of the widget. The names and properties of murmurs are grouped according to medical knowledge. For example, an aortic stenosis murmur is best heard at the right upper sternal border and radiates to the carotid arteries, and so the button for "aortic stenosis" occurs on the same line as "best heard at RUSB" and "radiation to carotids." There is some redundancy built in to the widget's appearance, but there is no redundancy in the underlying state (the underlying data representation), which means that if the user selects "RUSB" in the "Heart best at" part of the upper section, then the button for "best heard at RUSB" will also light up in the lower section. As another example, if the user selects "best heard at LLSB" in the lower section, then "LLSB" will also light up in the upper section. The widget is designed and arranged to prompt the user to remember what murmur properties are related to what specific types of murmurs.

Figure 45:
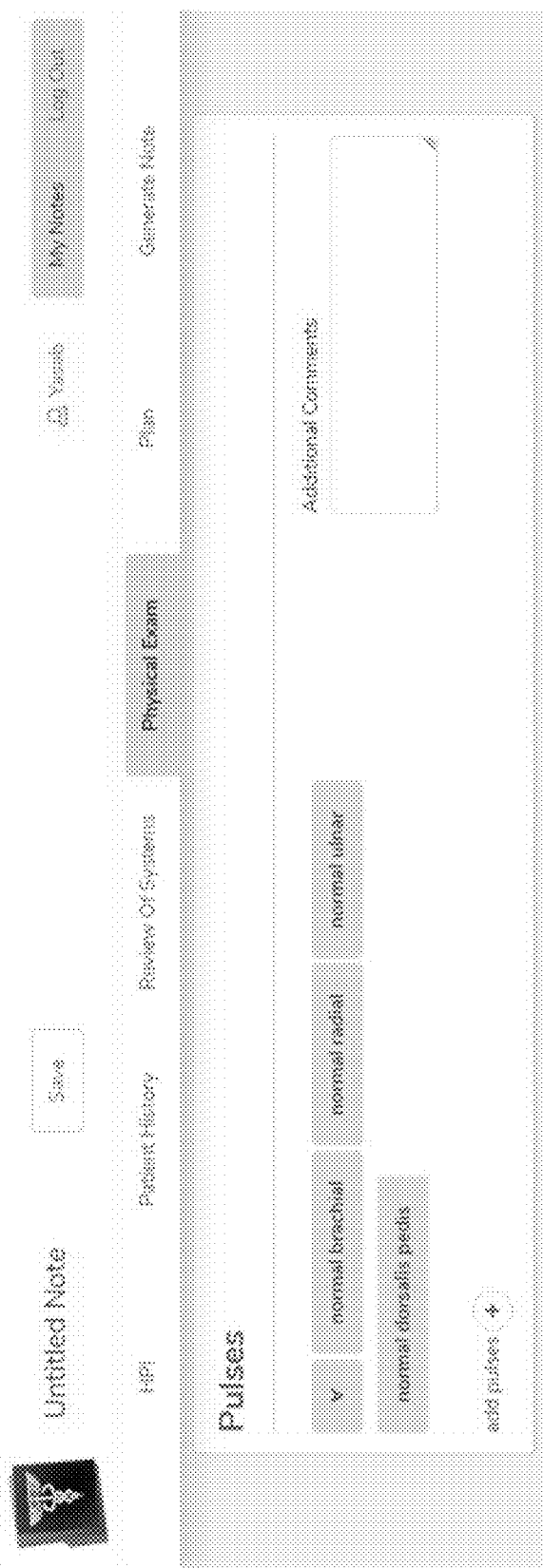

FIG. 45 shows part of a Physical Exam section, specifically the section for Pulses. If the user clicks on "add pulses" they will be shown a pulses widget that enables them to enter abnormal pulses.

Figure 46:
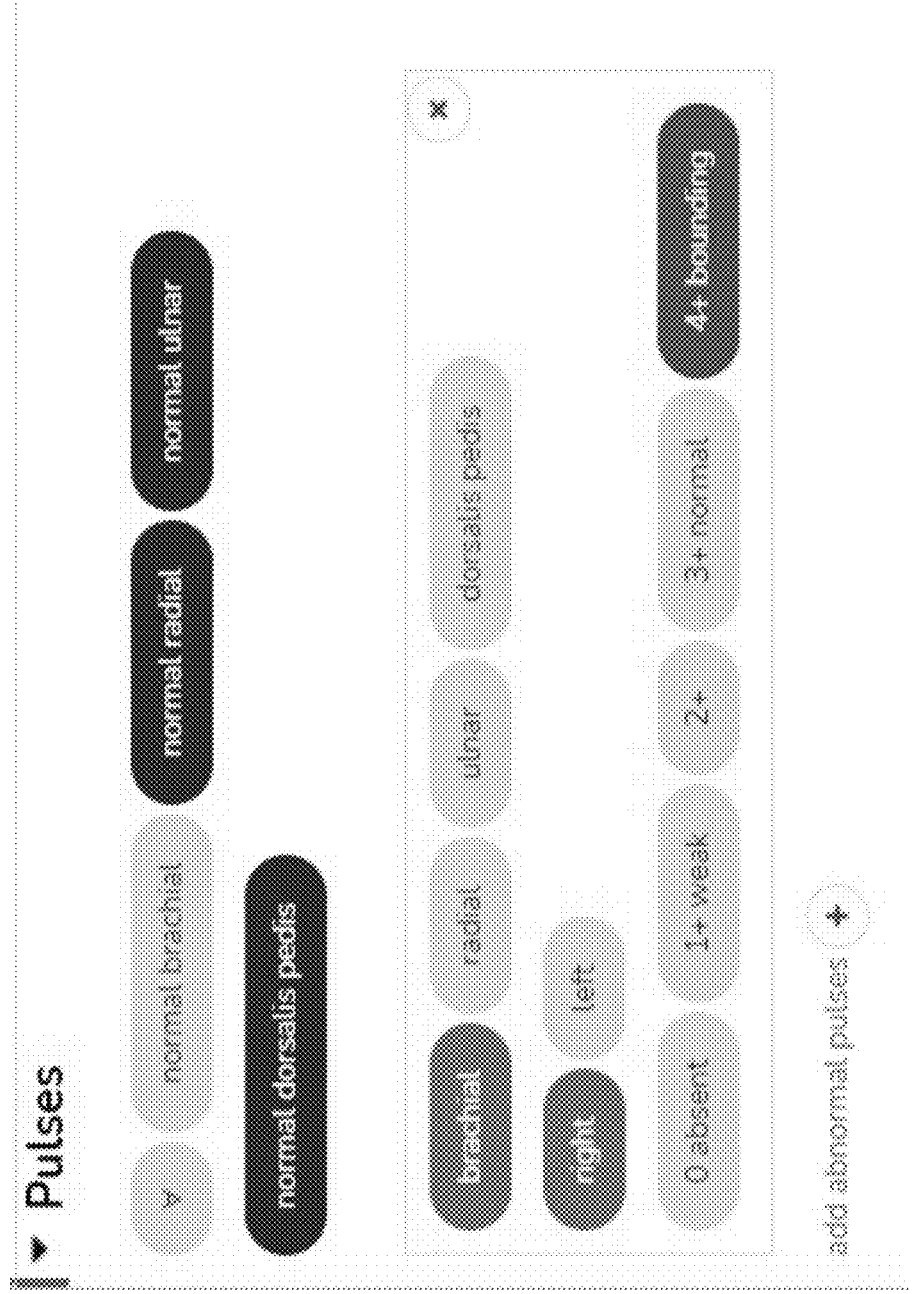

FIG. 46 shows part of a Physical Exam section, specifically the section for Pulses. Here the user has indicated "normal radial," "normal ulnar," and "normal dorsalis pedis" pulses, and they have also clicked on "add pulses" so that the pulses widget is displayed. Within this pulses widget, "brachial," "right," and "4+ bounding" have been selected to indicate that the patient has a 4+ right brachial pulse on physical exam. More instantiations of the pulses widgets can be added (to specify more pulses) by clicking on the "add abnormal pulses" button.

Figure 47:
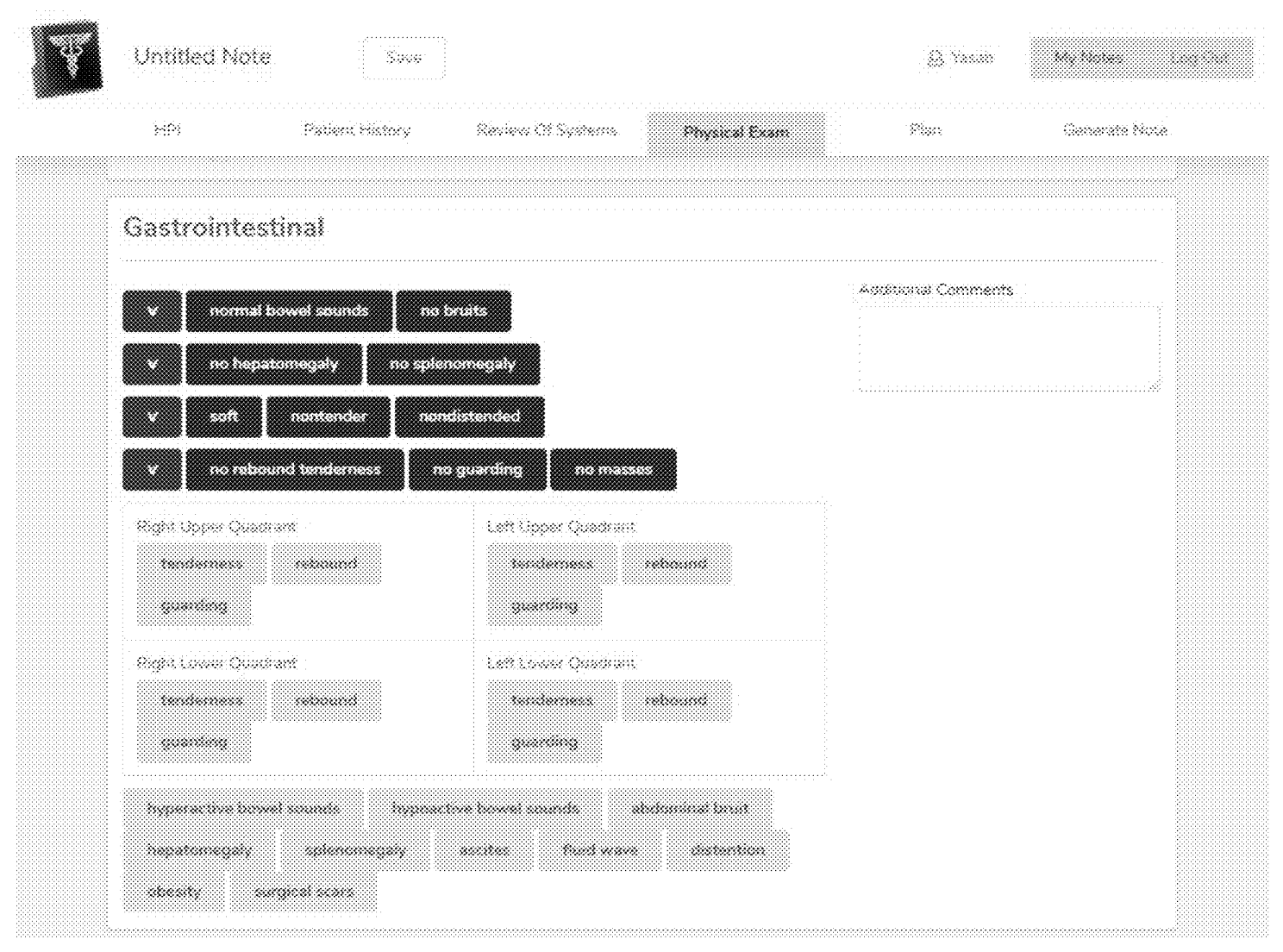

FIG. 47 shows part of a Physical Exam section, specifically the section Gastrointestinal, in which all normal options have been selected using the "for all" buttons, thus requiring only 4 clicks to select all these normal findings. Notice that the normal buttons are green when clicked.

Figure 48:
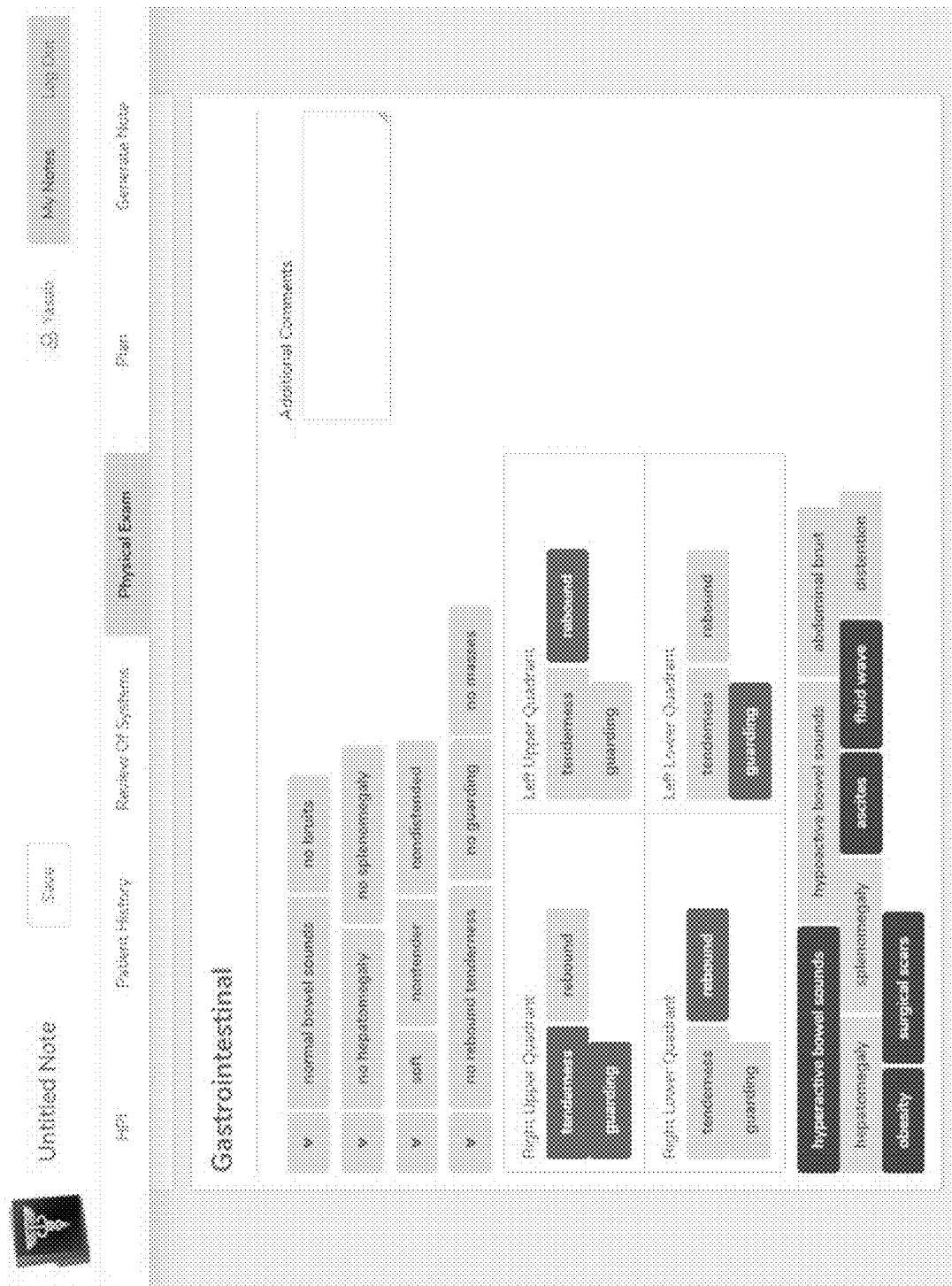

FIG. 48 shows part of a Physical Exam section, specifically the section Gastrointestinal, in which several abnormal options have been selected. Notice that the abnormal buttons are red when clicked. Additionally, the widget for gastrointestinal quadrants has been used to indicate abnormal findings in particular gastrointestinal quadrants. The widget is organized following the quadrants as seen when viewing a patient from the front, with the Right Upper Quadrant shown on the upper left (when viewing a patient from the front the clinician's left is the patient's right), and the Left Lower Quadrant shown on the bottom right. The user can select tenderness, rebound, and/or guarding for each quadrant.

Figure 49:

FIG. 49 shows part of a Physical Exam section, specifically the sections Extremities and Tendon Reflexes. In Tendon Reflexes there is a widget that can be used to specify an abnormal tendon reflex according to the location (biceps, brachioradialis, triceps, patellar, ankle jerk, plantar), side (right, left), and reflex strength (0, 1, 2, 3, 4). The user can add multiple abnormal reflexes by clicking on "add reflexes" repeatedly to pop up multiple copies of the widget.

Figure 50:
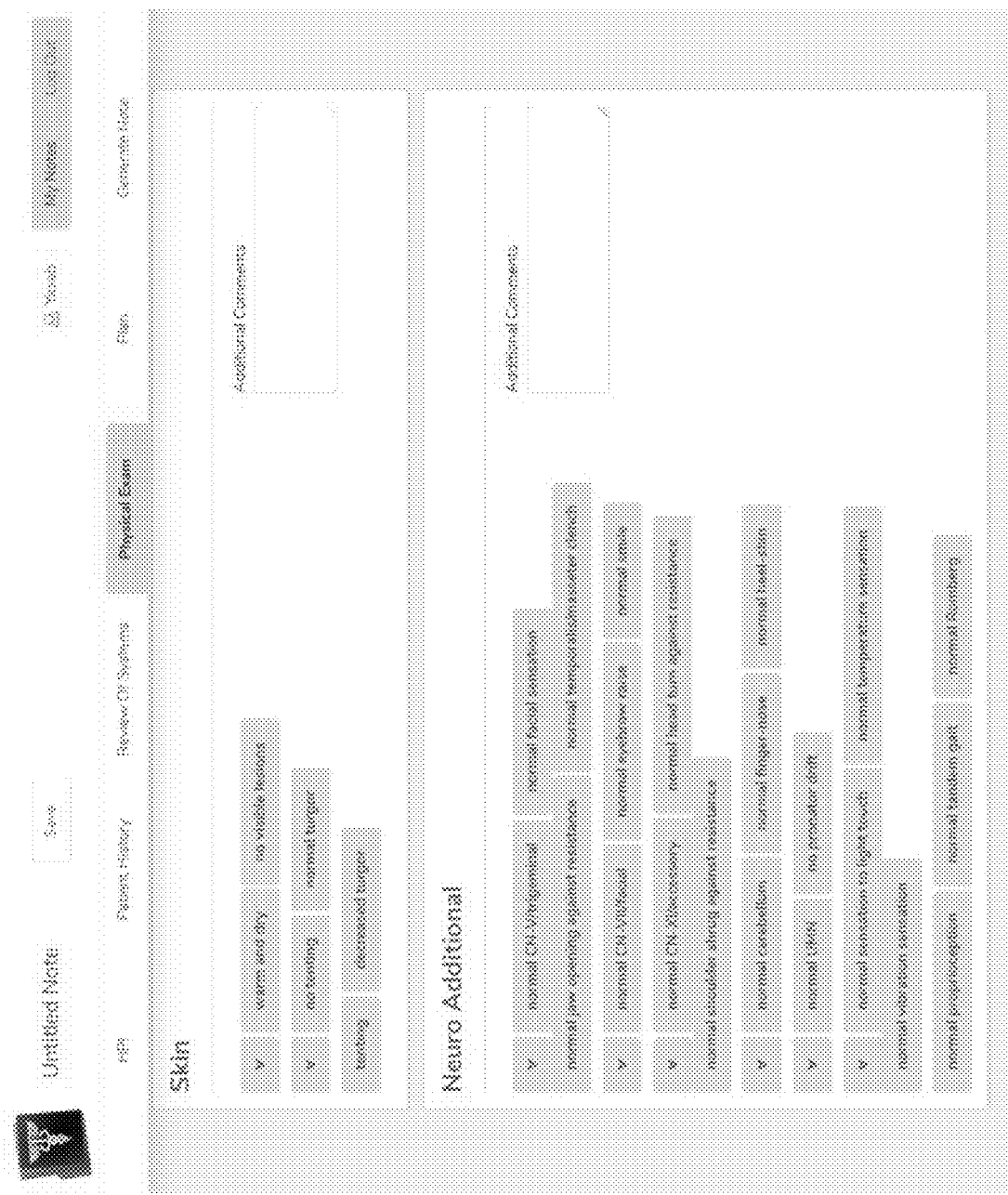

FIG. 50 shows part of a Physical Exam section, specifically the sections Skin and Neuro Additional.

Figure 51:
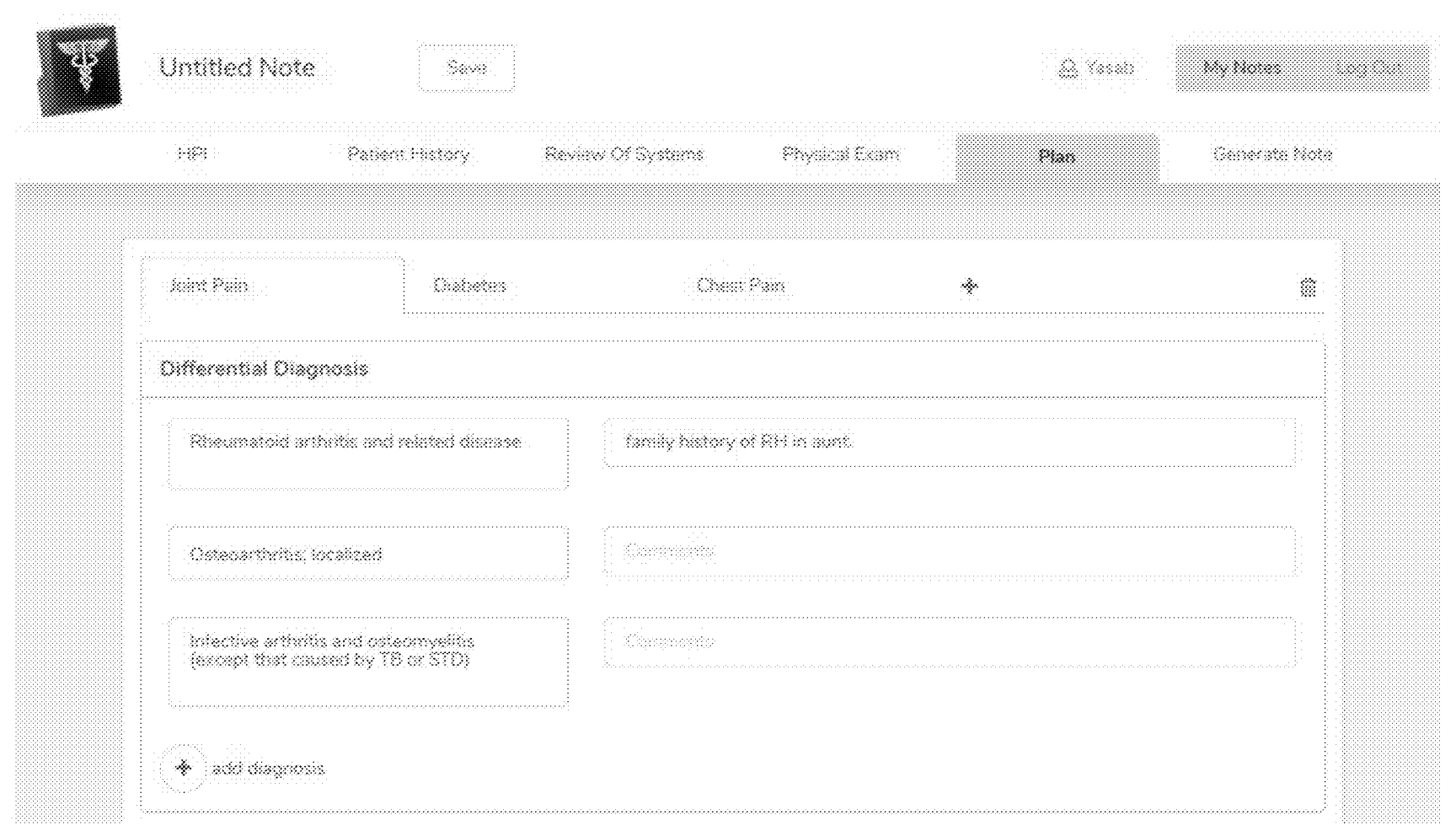

FIG. 51 shows part of a Discussion & Plan section, specifically the Differential Diagnosis. There are tabs for each of the Chief Complaints selected in the History of Present Illness section, in this example Joint Pain, Diabetes, and Chest Pain. For each Chief Complaint separately the user can enter a differential diagnosis. The user can enter as many differential diagnoses as they wish by clicking the "+add diagnosis" button as many times as is needed.

Figure 52:
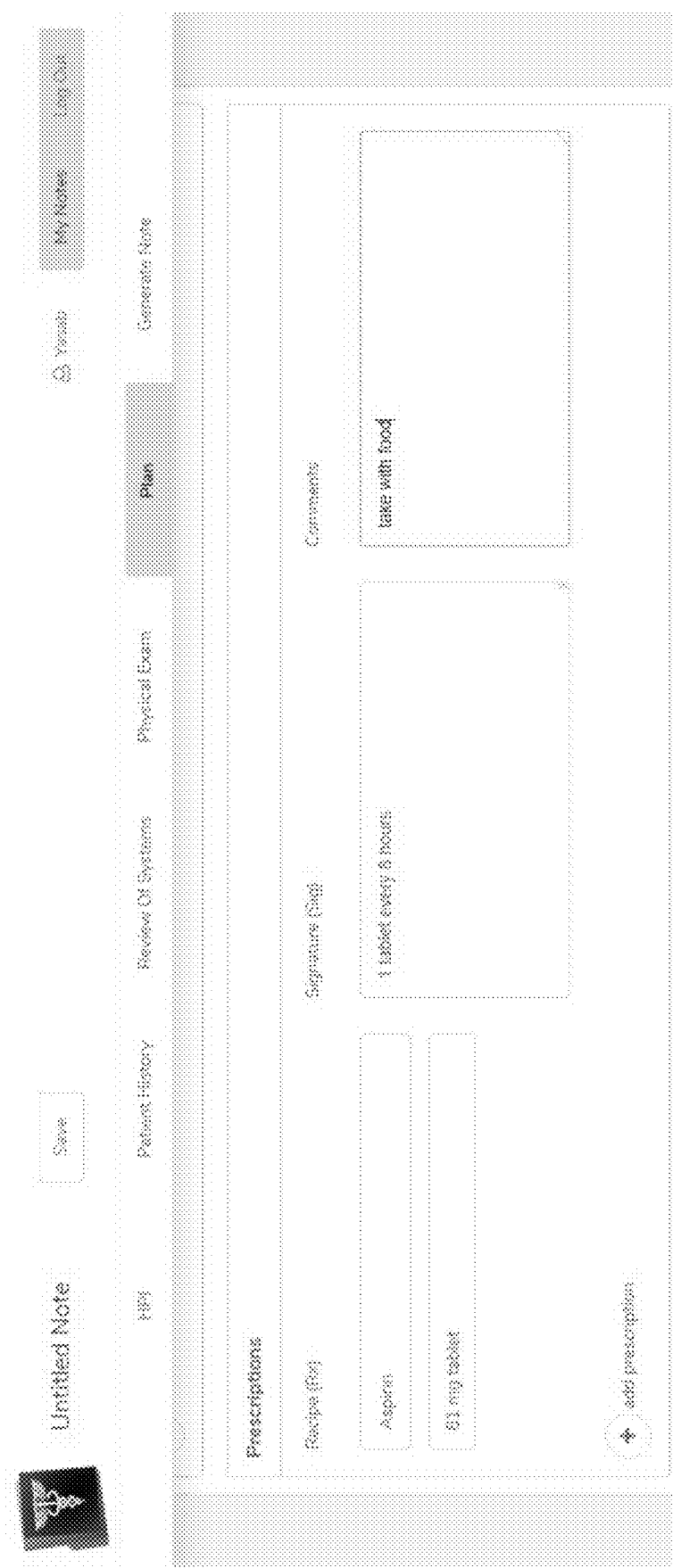

FIG. 52 shows part of a Discussion & Plan section, specifically the Prescriptions. For each Chief Complaint separately the user can enter Prescriptions, if any. In the example the user has entered aspirin 81 mg tablet. The user can enter as many medications as they wish by clicking the "+ add prescription" button.

Figure 53:
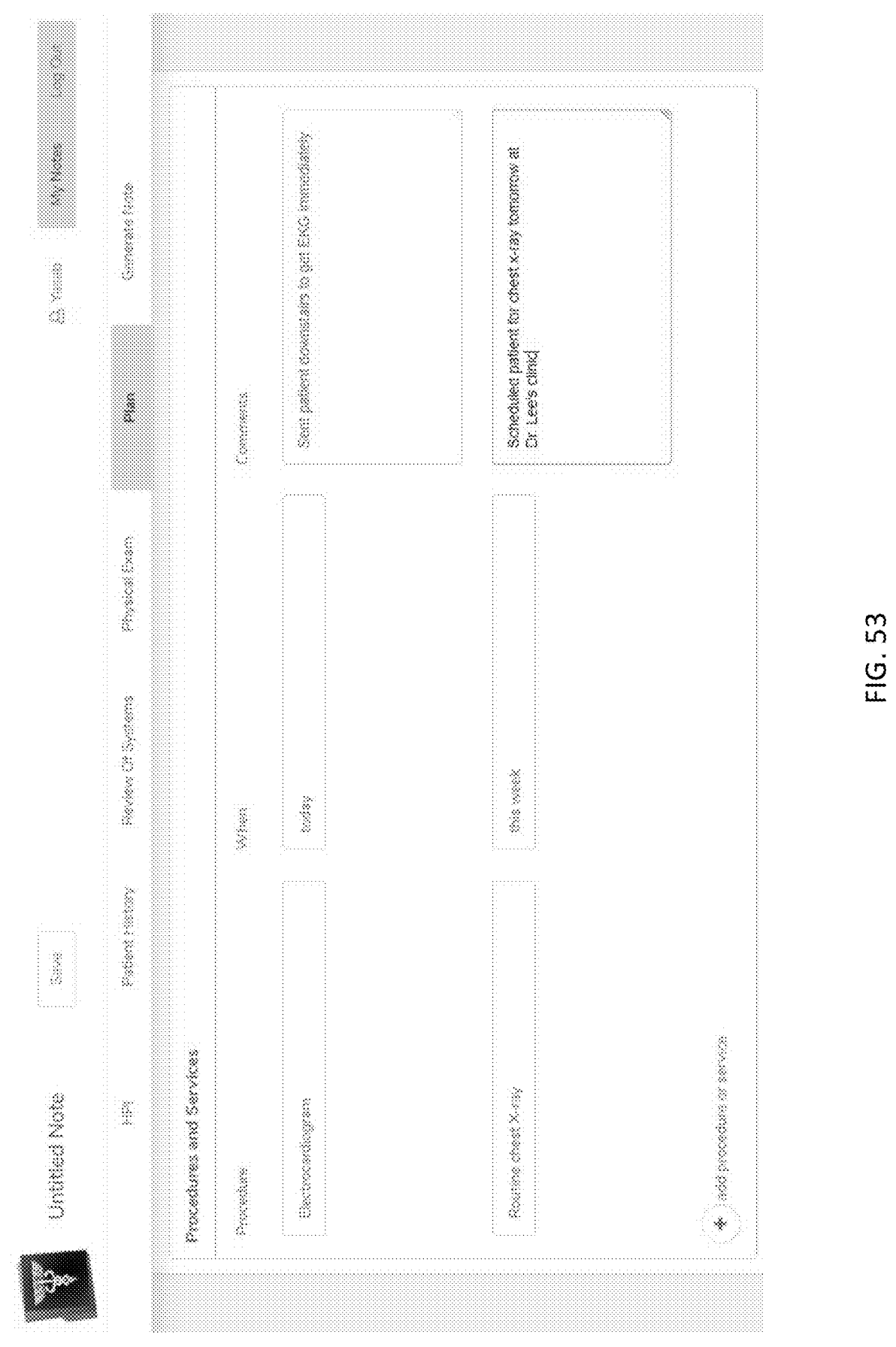

FIG. 53 shows part of a Discussion & Plan section, specifically Procedures and Services. For each Chief Complaint separately the user can enter Procedures and Services. Multiple Procedures and Services can be entered. In this example electrocardiogram and routine chest x-ray have been filled in along with "When" and "Comments." The user can add as many Procedures and Services as they wish by clicking the "+ add procedure or service" button.

Figure 54:
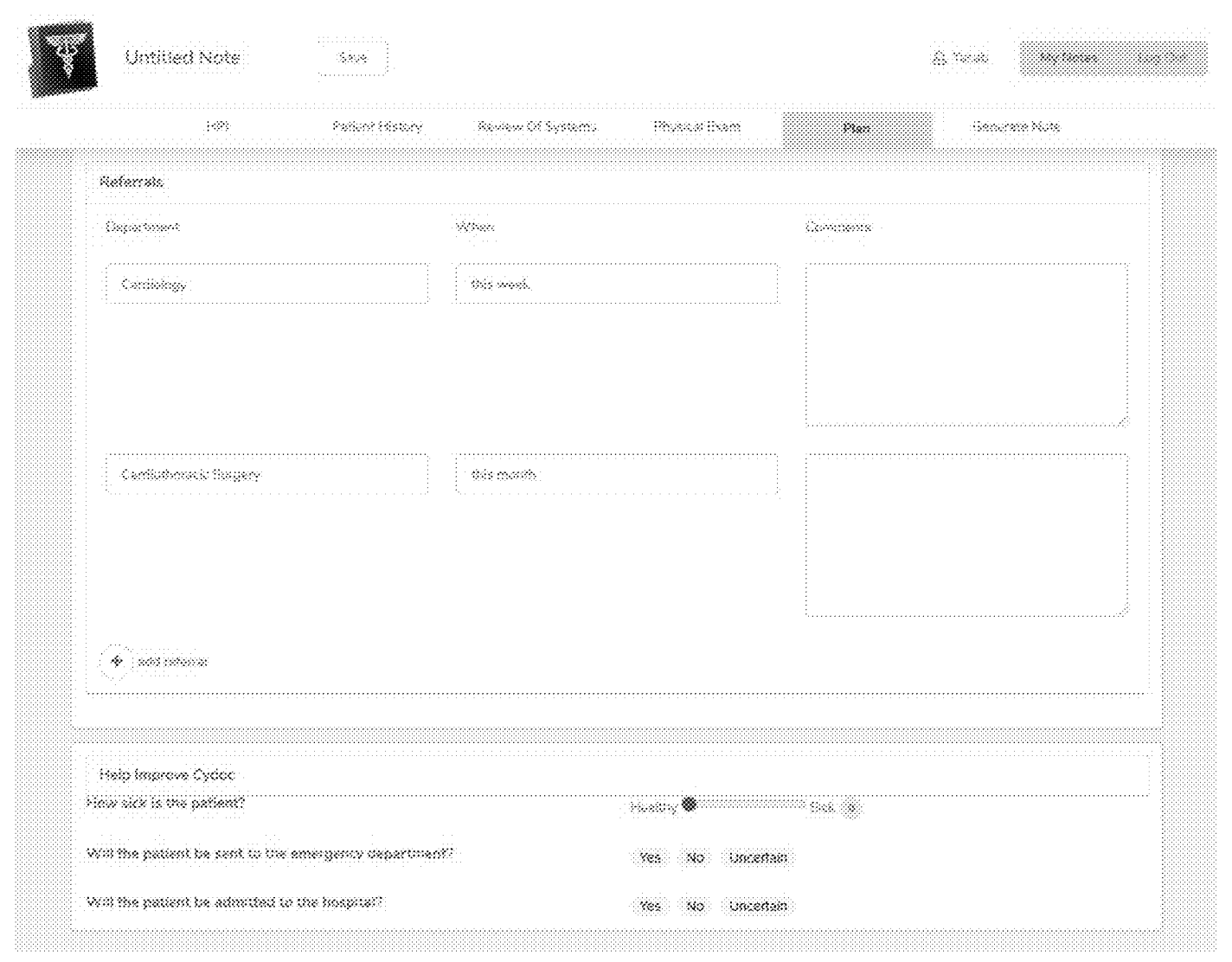

FIG. 54 shows part of a Discussion & Plan section, specifically Referrals and Help Improve Cydoc. In this example, Cardiology and Cardiothoracic Surgery have been entered as referrals. The user can add as many referrals as they wish by clicking the "+ add referral" button. The Help Improve Cydoc section is a section in which questions are posed to the user that will facilitate building artificial intelligence applications on the collected data. The questions included in this example are "How sick is the patient?" to enable building an artificial intelligence model to predict a numerical score for how sick the patient is; "Will the patient be sent to the emergency department?" to enable building an artificial intelligence model to predict whether the patient will need to go to the emergency department; and "Will the patient be admitted to the hospital?" to enable predicting whether the patent will need to be admitted to the hospital.

Figure 55:
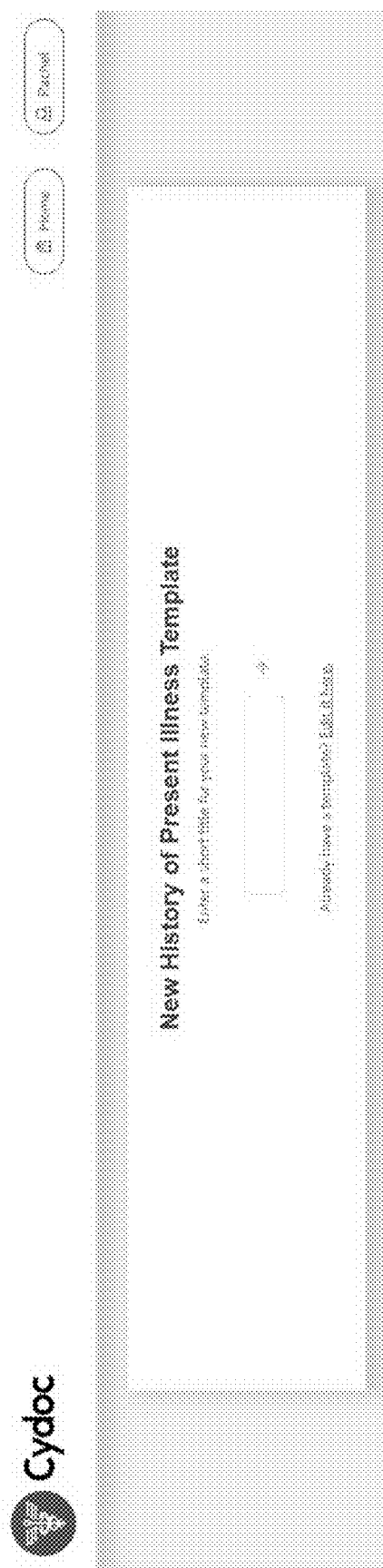

FIG. 55 shows part of a user interface for creating a custom History of Present Illness template (a custom HPI knowledge graph for a particular disease or condition of interest). On this page the user can enter a title for the custom History of Present Illness template.

FIG. 56 shows part of a user interface for creating a custom History of Present Illness template. The user can specify a Body System, in this example Cardiovascular/Hematologic. The user can specify a Disease, in this case "Heart Disease." While in this example the template name is "Heart disease" and disease name is also "Heart Disease", note that they do not have to be the same. For example the template name might be "Heart Disease Inpatient Template" and the disease name "Heart Disease."

Figure 57:
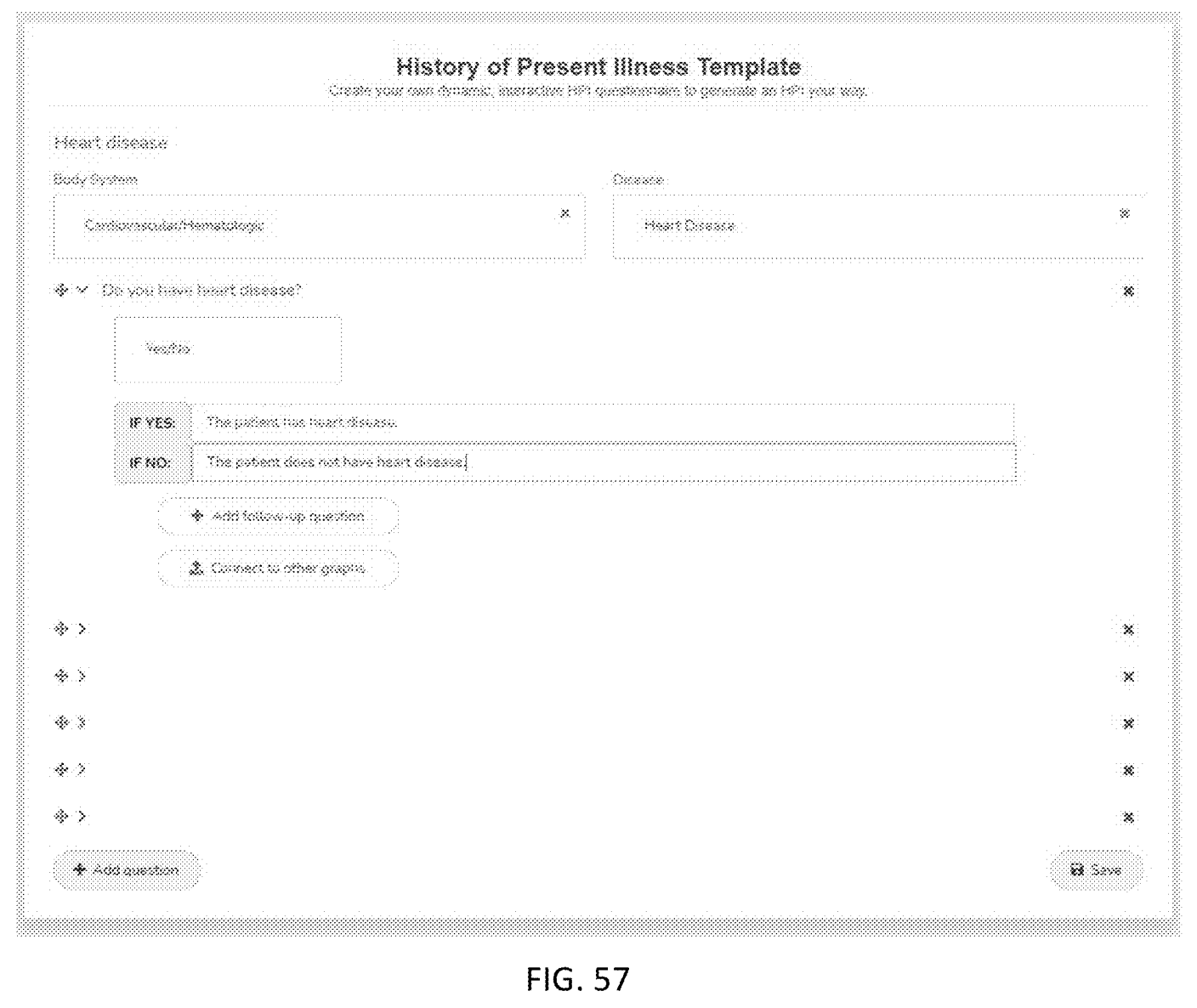

FIG. 57 shows part of a user interface for creating a custom History of Present Illness template. Here the user has written one question: "Do you have heart disease?" They have specified that this is a "Yes/No" question and so two template sentence boxes have appeared: one for "If Yes" and the other for "If No." The template sentence for "If Yes" has been filled in with "The patient has heart disease" in this example, while the template sentence for "If No" has been filled in with "The patient does not have heart disease." When a note is generated based off of this template, the template sentence for "If Yes" will be used when the answer to this question is Yes, while the template sentence for "If No" will be used when the answer to this question is No. Additionally, a button for "+Add follow-up question" can be seen; if this button is clicked there will be an option to add a follow-up question to this question (corresponding to a child node in the underlying knowledge graph data structure). A button for "Connect to other graphs" can also be seen, which enables connecting this question to another pre-existing collection of questions (corresponding to adding an edge between this question node and some other node in an existing knowledge graph). At the bottom of this figure, blank slots for five more questions can be seen, followed by an "+ Add question" button which enables adding yet more question slots.

Figure 58:
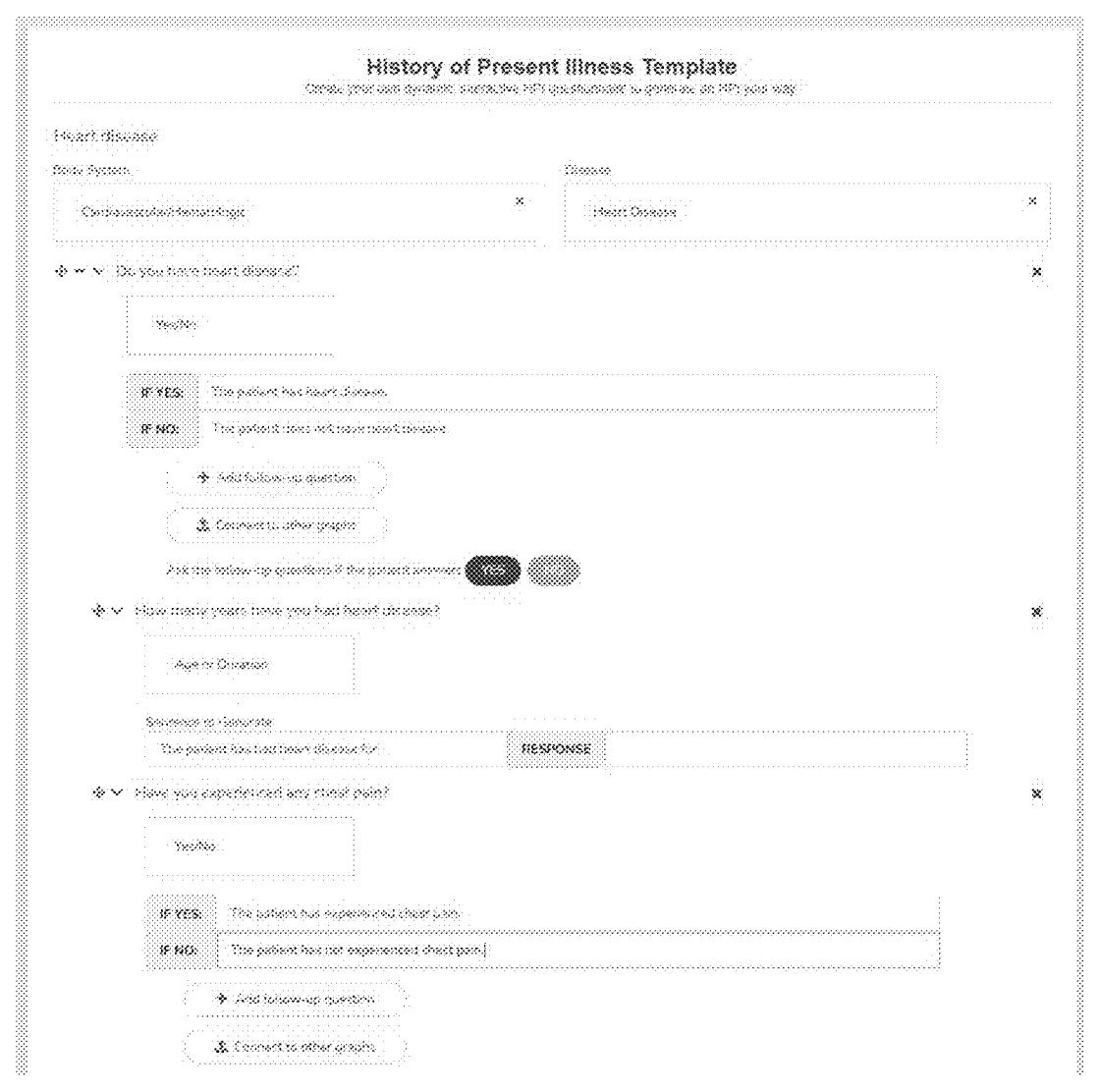

FIG. 58 shows part of a user interface for creating a custom History of Present Illness template. Here the user has written two follow-up questions for the question "Do you have heart disease?" One follow-up question is "How many years have you had heart disease?" and the selected question type is "Age or Duration" which when this template is used will cause the "Age or Duration" interface to appear below the question text so that the user can quickly input an amount of time. The user has written in template sentence (Sentence to Generate) as "The patient has had heart disease for RESPONSE" which means that if the user enters "5 years" when this template is used, the sentence that is generated from this question/answer/template sentence will be "The patient has had heart disease for 5 years." The other follow-up question that has been added is "Have you experienced any chest pain?" and the selected question type is Yes/No. Because this is a Yes/No question it needs two template sentences, one for a Yes response ("The patient has experienced chest pain") and one for a No response ("The patient has not experienced chest pain").

Figure 59:
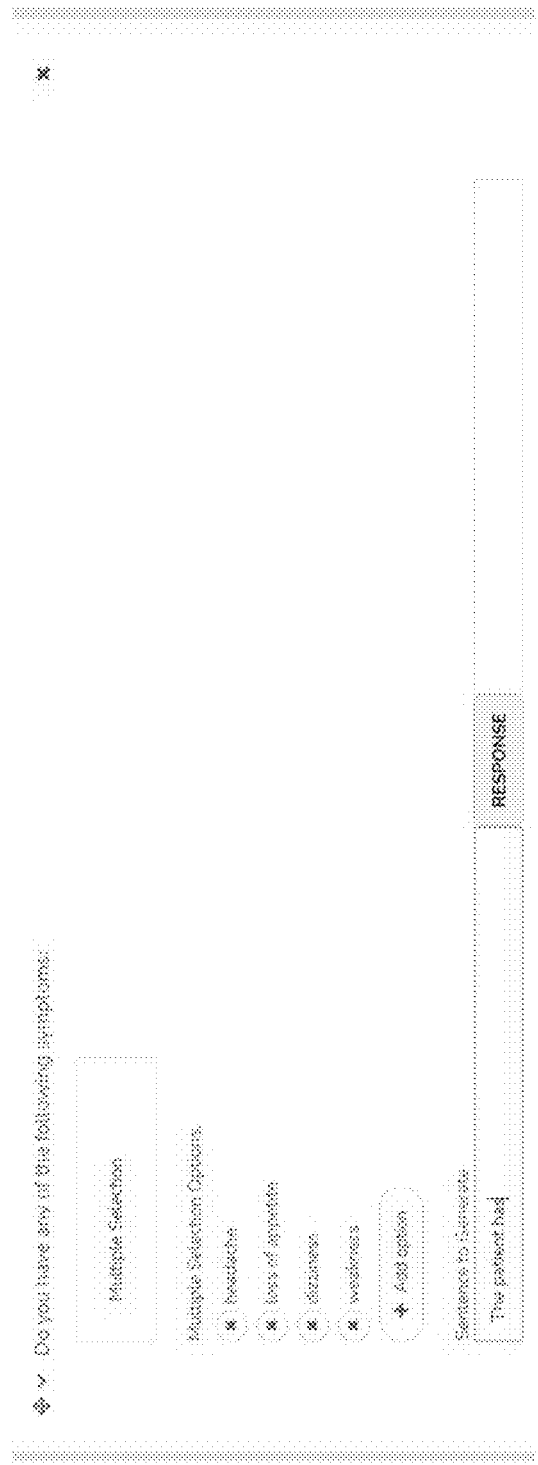

FIG. 59 shows part of a user interface for creating a custom History of Present Illness template. Here the user has written a Multiple Selection question "Do you have any of the following symptoms" with the options headache, loss of appetite, dizziness, and weakness. The "add option" button enables the user to continue adding options. The template sentence in this example is "The patient has RESPONSE" so for example if the user selected "headache, dizziness" when using this template, the generated sentence would be "The patient has headache and dizziness."

Figure 60:
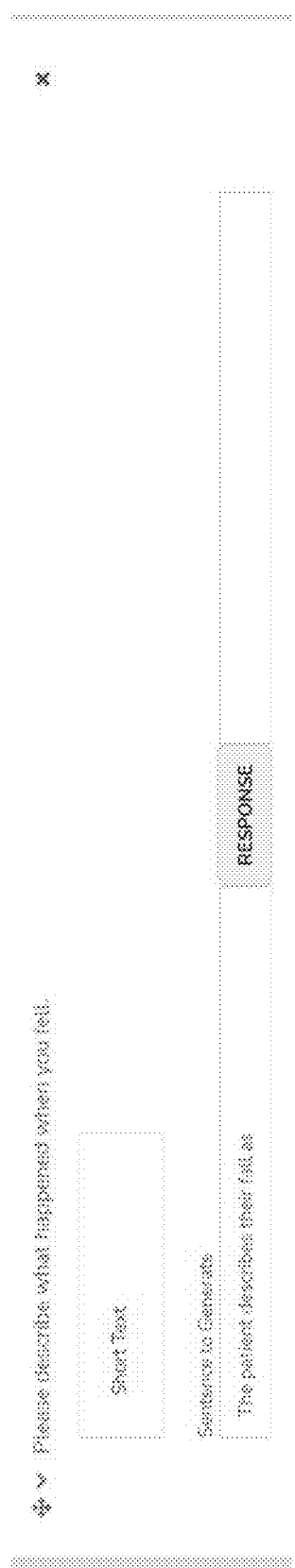

FIG. 60 shows part of a user interface for creating a custom History of Present Illness template. Here the user has written a Short Text response prompt "Please describe what happened when you fell." (Note that the phrase "response prompt" encompasses questions as well as other phrasings that request information.) The template sentence that the user has written here is "The patient describes their fall as RESPONSE."

Figure 61:
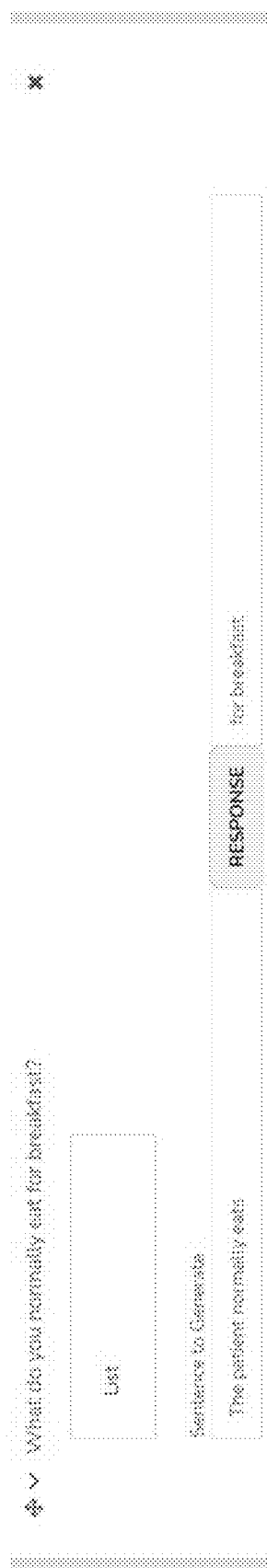

FIG. 61 shows part of a user interface for creating a custom History of Present Illness template. Here the user has written a List question "What do you normally eat for breakfast?" When this template is used to create a note, this List question will be shown with the List interface which enables the user to type into various boxes to create a list.

The template sentence that the user has written here is "The patient normally eats RESPONSE for breakfast."

Figure 62:
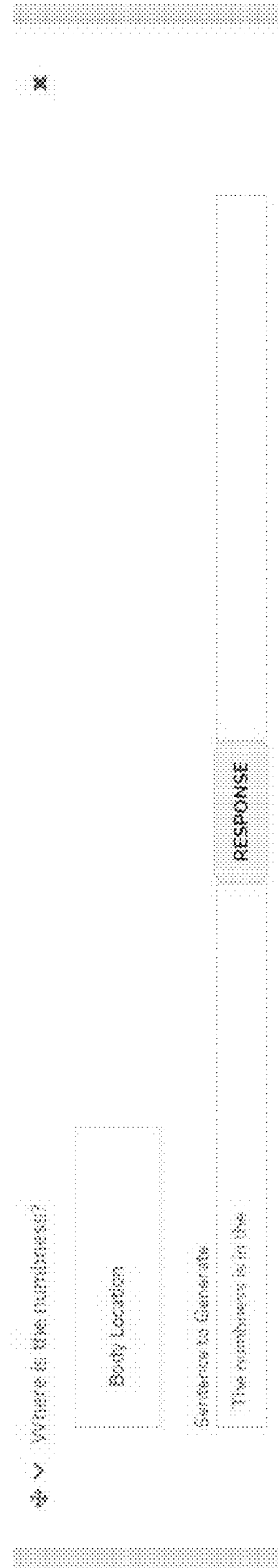

FIG. 62 shows part of a user interface for creating a custom History of Present Illness template. Here the user has written a Body Location question "Where is the numbness?" When this template is used to create a note, this Body Location question will be shown with the Body Location interface which enables to user to click on various body location options to specify the body location. The template sentence that the user has written here is "The numbness is in the RESPONSE." Overall, the user can select from many different question types in the interface when creating a template, including Yes/No, Multiple Selection, Short Text, Age or Duration, Number, List, Body Location, Past Medical History (sync), Family History (sync), Medications (sync), and Past Surgical History (sync). The question types listed here next to "(sync)" are BLANK or POP questions described earlier as special question types that enable synchronization of information between the History of Present Illness section and a corresponding Patient History section. For example, the Past Medical History (sync) option in the Create HPI Template interface creates a MEDS-BLANK question (if no specific medication options are entered), or a MEDS-POP question (if specific medication options are entered). Also note that the user can specify what kind of response should trigger asking child questions, and the user can re-order questions and change the relationships between questions, for example by dragging and dropping questions in the user interface.

FIG. 63 shows a user interface for creating a custom Physical Exam template. On the left, the Template Name area allows the user to type in a template name under which this Physical Exam template will be saved. The interface includes multiple cards, where each card may hold a topically related group of physical exam findings. The top card has the word "Body System" at the top which represents a place where the user can type in the relevant body system or other relevant descriptor for this group of physical exam findings. There are 3 lines shown with a drop-down for Line Type that enable the user to specify a line type, which can be Buttons, Dropdown, or Widget. The "Add Line" button at the bottom of each card enables the user to add more lines, and the "x" on the right enables the user to delete lines. On the bottom card the word "Eyes" has been filled in as the card title. The top row Line Type has been selected as "Buttons." The user has checked the "Select All" box which creates the select all button that will enable selecting all options on this row by clicking the button at the front with the "for all" symbol on it. The user has selected the "Normal" radio button which means that the buttons on this line will be green when clicked and represent normal findings. The user has typed in button text of "nontender" and "nondistended"; they can add more button text options using the plus button, and each piece of button text will be used to generate a separate button in the Physical Exam interface. The second row Line Type has been selected as "Buttons." The user has checked the "Left/Right" box which means that buttons on this row will be "left right buttons" which when clicked have L and R pop-out buttons on the side that enable the user to specify whether the finding is on the right, the left, or both sides. The user has clicked the "Abnormal" radio button which means that the buttons on this line will be red when clicked and represent abnormal findings. The user has typed in button text of "tender" and "distended" which means that in the Physical Exam interface these will show up as one button for "tender" and another button for "distended." On the third line, the Line Type has been selected as "Dropdown" and the user has typed in dropdown text options of "arcus senilis," "astigmatism," and "blepharitis" which means that these options will show up in a dropdown menu. The user can add more options to the Dropdown by clicking the plus button. The user can also specify if the dropdown needs Left/Right functionality; if this is chosen then when the Dropdown is used, clicking an item in the dropdown will cause a "left right button" to show up with that item's text on it so that the user can specify if it shows up on the left, right, or both sides. The final row has a Line Type of "Widget" which means another dropdown appears for selecting the widget. Widget options may include a tendon reflexes widget, pulses widget, cardiac murmurs widget, lung sounds widget, abdomen widget, and/or skin widget. The "Add Card" button at the bottom enables the user to add more cards.

Figure 64:
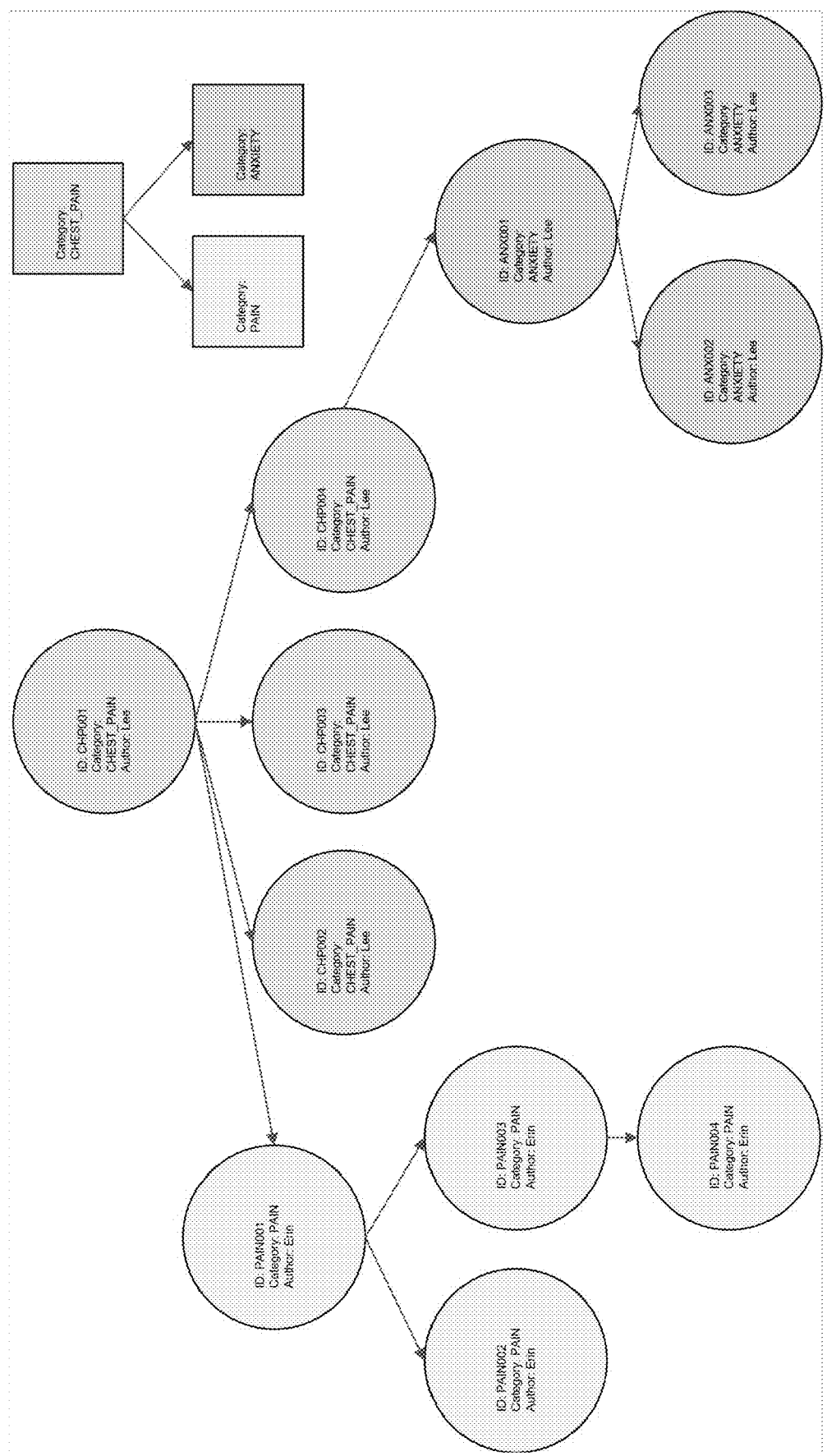

FIG. 64 shows an example illustrating a relationship between response prompt nodes (Question Nodes) and descriptive nodes (Category Nodes). In this example, the Question Nodes are shown as circles and the Category Nodes are shown as squares. The Question Nodes are connected to one another and each Question Node has an attribute ID (specifying the identity of the node), Category (specifying the disease category of the node), and Author (specifying the author of the node). One Category Node has been created for each value taken on by the Category attribute of the Question Nodes, meaning that in this example there are three Category Nodes: CHEST_PAIN, PAIN, and ANXIETY. Furthermore, the Category Nodes have been connected to each other by edges according to the connectivity of the Question Nodes. Because a Question Node with Category CHEST_PAIN has a child node with Category PAIN, the Category Node CHEST_PAIN has a child Category Node PAIN. Because a Question Node with Category CHEST_PAIN has a child node with Category ANXIETY, the Category Node CHEST_PAIN has a child Category Node ANXIETY. Thus, the Category Node connectivity represents a summary of the Question Node Category attribute connectivity. Notice that in this example there are no connections (edges) between the Question Nodes and the Category Nodes.

Figure 65:
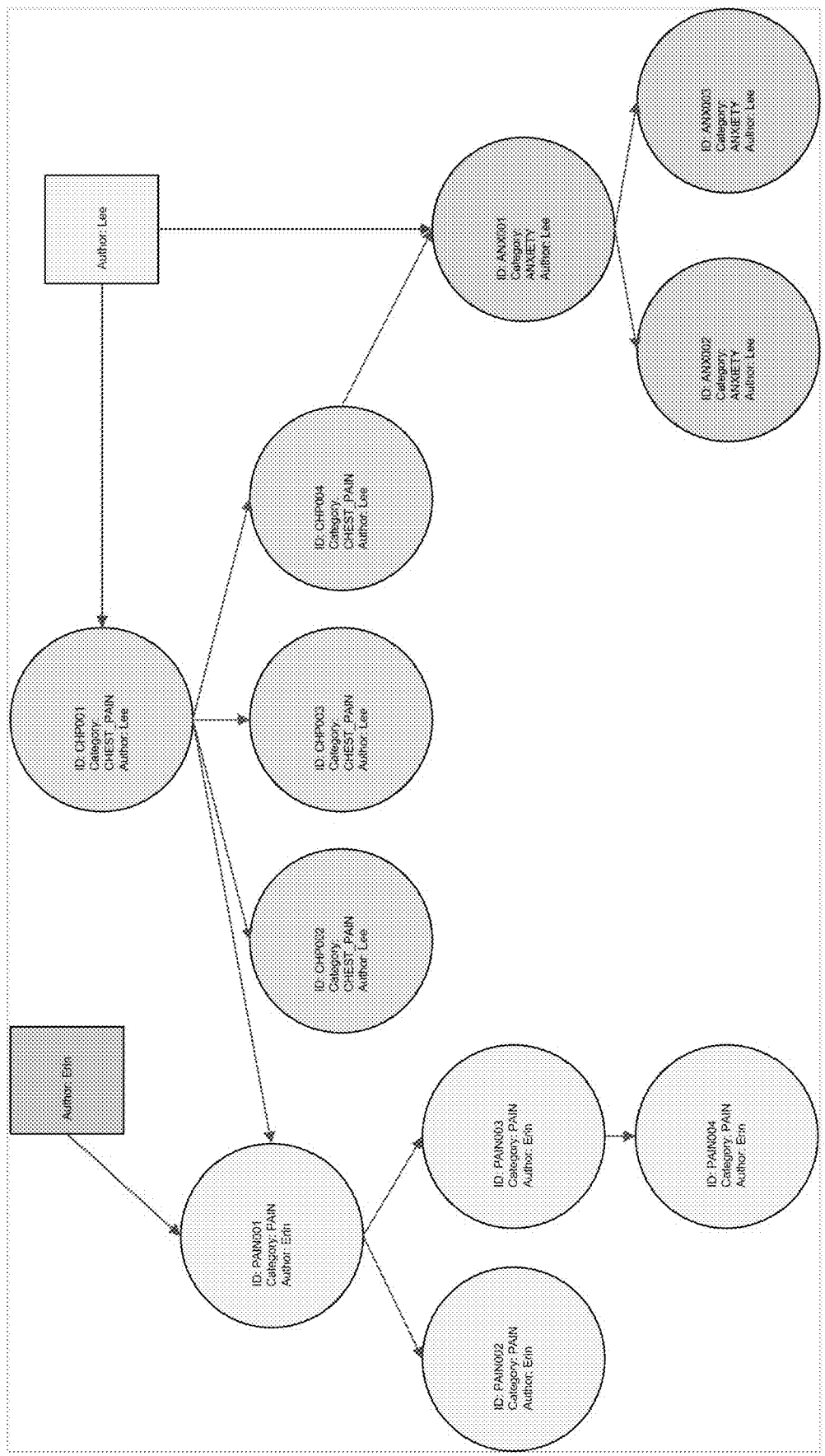

FIG. 65 shows an example illustrating a relationship between response prompt nodes (Question Nodes) and additional nodes describing the node author (Author Nodes or Doctor Nodes). In this example, the Question Nodes are shown as circles and the Doctor Nodes are shown as squares. Each Doctor Node has a connection (edge) to the root node of each Question Node subgraph for which the Author attribute of the Doctor Node matches the Author attribute of the Question Node.

Figure 66:
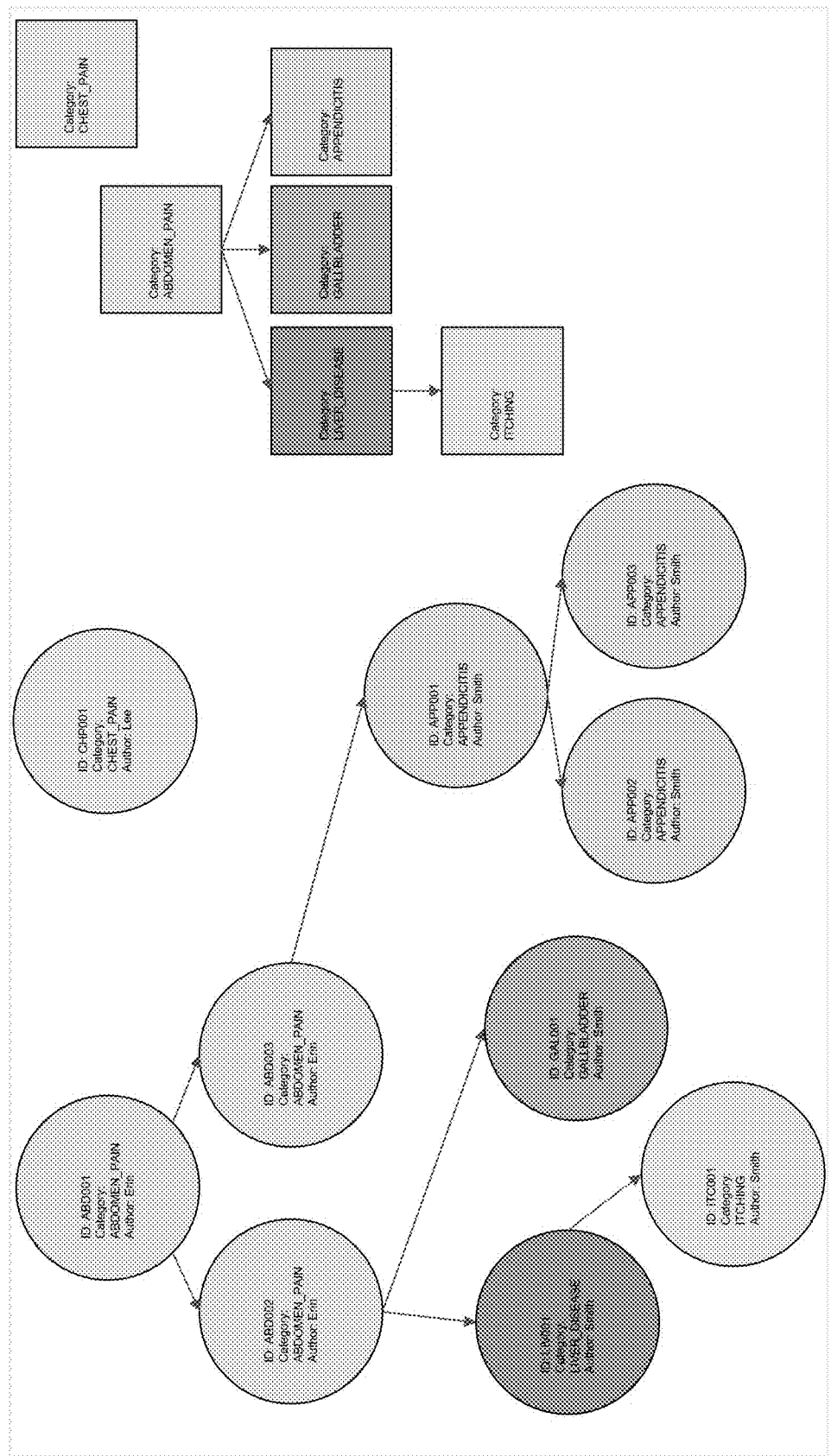

FIG. 66 shows an example illustrating a relationship between response prompt nodes (Question Nodes) shown as circles and descriptive nodes (Category Nodes) shown as squares. Similar to the example in FIG. 64, the connectivity of the Category Nodes is determined by the connectivity of the Question Nodes and the Category attribute of the Question Nodes.

FIG. 67 shows an example illustrating a relationship between response prompt nodes (Question Nodes) shown as circles and additional nodes describing the node author (Author Nodes or Doctor Nodes) shown as squares. Similar to the example in FIG. 65, Doctor Nodes are connected to Question Nodes for which the value of the Author attribute in the Question Node matches the value of the Author attribute in the Doctor Node.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodi-

What is claimed is:

1. A method comprising:
at a computing device comprising at least one processor and memory:
constructing a data structure including a set of nodes comprising an author node, a topic node, and a plurality of response prompt nodes, wherein the author node corresponds to the author of the response prompts, wherein the topic node corresponds to a topic, wherein each of the response prompt nodes corresponds to one of the response prompts, wherein each response prompt node is associated with a display type and one or more template sentences, wherein the nodes are linked by edges, such that the author node links to all of the response prompt nodes, the topic node links to all of the response prompt nodes, and the response prompt nodes are linked to each other in an ordered directed tree, and wherein each edge of the ordered directed tree is assigned a unique integer order, and is traversable based on a response to a response prompt at the respective response prompt node; and
providing a user interface configured to display one or more response prompts from the response prompt nodes according to their respective display types for preparing a narrative of an interaction with a subject, wherein the one or more response prompts include prompts for input of the subject's history of present illness, medication usage, allergies, family health history, past medical history, surgical history, social history, Physical examination findings, review of systems, and discussion and plan, and wherein each response prompt node corresponds to one response prompt, and each response prompt node is associated with a note section attribute that indicates the note section of the response prompt where note sections are defined as history of present illness, medication usage, allergies, family health history, past medical history, surgical history, social history, physical examination findings, review of systems, and discussion and plan
providing a narrative build manager configured to:
receive one or more responses to the displayed one or more response prompts;
use the one or more responses to traverse the edges;
construct text for each response prompt node via insertion of the response into the template sentence, or by using the response to select from a set of template sentences;
concatenate the text into a paragraph by traversing the nodes according to the tree connectivity and ordering of the edges;
employ techniques for improving the quality of the text using rules, wherein the rules include:
rules to change verb tense from first person or second person to third person:
rules to create gender-specific language from gender-neutral language;
rules to replace the phrase "the patient" with "he" or "she" or the patient's name; and
rules to replace colloquial medical terms with formal medical terms;
present, via the user interface, a narrative of interaction with the subject including the paragraph.

2. The method of claim 1, wherein the response prompts each comprise one of a question, statement requesting information, or multiple-choice prompt.

3. The method of claim 1, wherein each template sentence is a grammatically complete sentence, a sentence fragment, or a sentence with a placeholder into which a response to a response prompt may be inserted.

4. The method of claim 1, wherein the response prompts each comprise a request for health-related information about the subject.

5. The method of claim 1, wherein receiving the plurality of response prompts comprises receiving, at the computing device, user input of the response prompts.

6. The method of claim 1, further comprising receiving, at the computing device, a specification for an ordering of and interrelation of the nodes, and
wherein constructing the data structure comprises linking the nodes based on the interrelation of the nodes, and additionally storing the ordering of the nodes within the data structure.

7. The method of claim 1, wherein the narrative comprises text in the form of a plurality of sentences.

8. The method of claim 1, wherein each node is associated with a response prompt type such as yes or no, multiple choice, text, list, number, time, or body location, and each response prompt is displayed via a user interface that is customized according to each response prompt node's response prompt type.

9. The method of claim 1, wherein each node is associated with one or more attributes that define the node's response prompt, response prompt type, related body system, related disease category or abnormality, related note section, child nodes, and/or one or more template sentences.

10. The method of claim 1, wherein the interaction is an interview of the subject.

11. The method of claim 1, wherein the response prompt nodes include a parent node and two or more child nodes that are each linked to the parent node, and wherein the links between the parent node and the child nodes are traversable based on a response to a response prompt at the parent node, and
wherein the narrative build manager is configured to:
receive a response to the response prompt at the parent node;
use the response to the response prompt at the parent node to traverse a link or links to one or more of the child nodes;
receive a response to the response prompt at one or more of the child nodes; and
construct a narrative based on the responses to the response prompts for the parent node and/or one or more of the child nodes.

12. The method of claim 1, further comprising presenting the constructed narrative.

13. The method of claim 12, wherein presenting the constructed narrative comprises displaying the constructed narrative.

14. The method of claim 1, further comprising receiving, via a user interface, user input of the one or more responses.

15. The method of claim 14, wherein any user responses to any response prompts presented within the history of present illness section in a user interface, that are related to the subject's patient history, are stored in the same part of the system's state as the data for independent user interface sections for patient history, to enable synchronization of data between the history of present illness and the independent user interface sections for patient history, where patient history refers to medication usage, allergies, family health history, past medical history, surgical history, and/or social history.

16. The method of claim 14, further comprising storing user input of the one or more responses in association with a unique patient identifier.

17. The method of claim 16, further comprising generation of a unique patient identifier such that it contains a substring generated by random sampling from prespecified numeric ranges such that a training, validation, and test split for patients can be inferred from the patient identifier alone.

18. The method of claim 16, further comprising linking the unique patient identifiers according to familial relationships such as parent-child or sibling-sibling, and storing these links and specified familial relationships in a database.

19. The method of claim 1, further comprising receiving, via a photograph or scan or digitization of a paper form, user input of the one or more responses.

20. The method of claim 19, further comprising transformation of the digital image data of the paper form into structured electronic data using artificial intelligence techniques.

21. The method of claim 1, further comprising associating a rating to the data structure.

22. The method of claim 21, further comprising present the rating to one or more users via a social network.

23. The method of claim 1, further comprising generating a predictive model based in whole or in part on received responses to the one or more response prompts.

24. The method of claim 1, further comprising:
receiving a specification for a predictive model; and
generating predictions based on the received responses to the one or more response prompts.

25. The method of claim 24, wherein the predictive model is optimized for use to predict one or more of diagnosis, future diagnostic workup, treatments, whether the subject requires a referral or a consultation, how ill the subject is on a numeric scale, whether the subject needs admission to a hospital, and/or what additional questions to ask the subject.

26. The method of claim 24, wherein receiving the specification for the predictive model comprises receiving the specification for the predictive model from a user via a user interface.

27. The method of claim 1, further comprising, at the computing device: constructing a plurality of other data structures that each correspond to a different topic, and wherein the plurality of data structures each include an author node, a topic node, and a plurality of response prompt nodes.

28. The method of claim 27, wherein each of the plurality of other data structures are associated with a different author.

29. The method of claim 28, further comprising, at the computing device:
receiving, via the user interface, user specification of an author; and
in response to receiving the user specification of the author, retrieving and/or displaying at least one response prompt node that matches the specified author.

30. The method of claim 27, further comprising, at the computing device:
receiving, via the user interface, user specification of a topic; and
in response to receiving the user specification of the topic, retrieving and/or displaying at least one response prompt node that matches the specified topic.

* * * * *